(12) United States Patent
Kaplan et al.

(10) Patent No.: US 11,247,181 B2
(45) Date of Patent: Feb. 15, 2022

(54) BIOMIMETIC MULTILAYER COMPOSITIONS

(71) Applicants: Trustees of Tufts College, Medford, MA (US); Massachusetts Institute of Technology, Cambridge, MA (US)

(72) Inventors: David L. Kaplan, Concord, MA (US); Markus J. Buehler, Boxford, MA (US); Shengjie Ling, Allston, MA (US)

(73) Assignees: Trustees of Tufts College, Medford, MA (US); Massachusetts Institute of Technology, Cambridge, MA (US)

(*) Notice: Subject to any disclaimer, the term of this patent is extended or adjusted under 35 U.S.C. 154(b) by 42 days.

(21) Appl. No.: 16/344,505

(22) PCT Filed: Oct. 24, 2017

(86) PCT No.: PCT/US2017/058134
§ 371 (c)(1),
(2) Date: Apr. 24, 2019

(87) PCT Pub. No.: WO2018/081159
PCT Pub. Date: May 3, 2018

(65) Prior Publication Data
US 2019/0247803 A1    Aug. 15, 2019

Related U.S. Application Data

(60) Provisional application No. 62/412,124, filed on Oct. 24, 2016.

(51) Int. Cl.
*B01D 69/14* (2006.01)
*D01B 7/00* (2006.01)
(Continued)

(52) U.S. Cl.
CPC ........ *B01D 69/144* (2013.01); *A61L 27/3604* (2013.01); *A61L 27/46* (2013.01);
(Continued)

(58) Field of Classification Search
None
See application file for complete search history.

(56) References Cited

U.S. PATENT DOCUMENTS 5,245,012 A   9/1993 Lombari
7,727,575 B2  6/2010 Kaplan
(Continued)

FOREIGN PATENT DOCUMENTS

WO   1997008315    3/1997
WO   2011130335   10/2011
(Continued)

OTHER PUBLICATIONS

Nogueira et al., "Layer-by-Layer Deposited Chitosan/Silk Fibroin Thin Films with Anisotropic Nanofiber Alignment", Langmuir, vol. 26, 2010, p. 8953-8958. (Year: 2010).*
(Continued)

*Primary Examiner* — Chinessa T. Golden
(74) *Attorney, Agent, or Firm* — Quarles & Brady, LLP

(57) ABSTRACT

The present invention provides, inter alia, compositions including at least one pliable layer comprising a plurality of silk fibroin nanofibrils, and at least one rigid layer comprising a plurality of mineral crystals, wherein each rigid layer is associated with at least one pliable layer, as well as methods for the production and use thereof.

20 Claims, 18 Drawing Sheets

FLAKE SIZE: 6*30*240 nm
VOLUME RATIO IN SOLUTION: 0.00059
DENSITY: 3000 kg/m3
MODULUS: $E=114$ GPa
    $G= 44.5$ Gpa (PURE HAP)
HAP-HAP SURFACE ENERGY:
$\gamma=0.8147$ J/m$^2$ (AVERAGED INTERFACIAL ENERGY FOR HAP IN SOLVENT, FROM LITERATURE)

HAP

FIBER SIZE: 10 (DIAMETER) *1000 (CONTOUR LENGTH) nm
VOLUME RATIO IN SOLUTION: 0.00077
DENSITY: 1300 kg/m$^3$
MODULUS: $E=1.5$ Gpa (SILK FIBER)
SNF-SNF SURFACE ENERGY:
$\gamma=0.217$ J/m$^2$ (AVERAGED INTERFACIAL ENERGY FOR α-HELIX PROTEIN IN SOLVENT, FROM LITERATURE)

SNF

(51) Int. Cl.
| | |
|---|---|
| A61L 27/36 | (2006.01) |
| A61L 27/56 | (2006.01) |
| A61L 27/46 | (2006.01) |
| B01D 67/00 | (2006.01) |
| B01D 69/12 | (2006.01) |
| B01D 71/02 | (2006.01) |
| B01D 71/74 | (2006.01) |
| C02F 1/44 | (2006.01) |
| C02F 101/22 | (2006.01) |

(52) U.S. Cl.
CPC .......... *A61L 27/56* (2013.01); *B01D 67/0079* (2013.01); *B01D 69/12* (2013.01); *B01D 71/02* (2013.01); *B01D 71/74* (2013.01); *C02F 1/44* (2013.01); *D01B 7/00* (2013.01); *A61L 2400/12* (2013.01); *C02F 2101/22* (2013.01); *Y10T 428/24996* (2015.04); *Y10T 428/24998* (2015.04); *Y10T 428/249953* (2015.04); *Y10T 428/249954* (2015.04); *Y10T 428/249964* (2015.04); *Y10T 428/249979* (2015.04); *Y10T 428/249981* (2015.04)

(56) References Cited

U.S. PATENT DOCUMENTS

| | | | |
|---|---|---|---|
| 8,337,938 | B2 | 12/2012 | Knight |
| 8,623,398 | B2 | 1/2014 | Altman |
| 2013/0210301 | A1* | 8/2013 | Hirao ................ C08J 9/283 442/59 |
| 2015/0056294 | A1 | 2/2015 | Kaplan |

FOREIGN PATENT DOCUMENTS

| | | |
|---|---|---|
| WO | 2013152265 | 10/2013 |
| WO | 2018026853 | 2/2018 |

OTHER PUBLICATIONS

Vandezande, P. et al, Solvent resistant nanofiltration: separating on a molecular level. Chem. Soc. Rev. 37, 365-405 (2008).
Vankelecom, IFJ et al. , Nanofiltration membrane materials and preparation, pp. 34-65 in Nanofiltration: Principles and Applications. Elsevier (2005).
Wang, H. et al, Mechanism study on adsorption of acidified multiwalled carbon nanotubes to Pb(II). J. Colloid Interface Sci. 316, 277-283 (2007).
Wang, J.-S. et al., Preparation of ethylenediaminemodified magnetic chitosan complex for adsorption of uranyl ions. Carbohydr. Polym. 84, 1169-1175 (2011).
Wang, Q. et al. Ultrafiltration membranes composed of highly crosslinked cationic polymer gel: The network structure and superior separation performance. Adv. Mater. 23, 2004-2008 (2011).
Wang, X. et al, Mass production of micro/nanostructured porous ZnO plates and their strong structurally enhanced and selective adsorption performance for environmental remediation. J. Mater. Chem. 20, 8582-8590 (2010).
Werber, J. et al., Materials for next-generation desalination and water purification membranes. Nat. Rev. Mater. 16018 (2016).
Yu, J. et al., "Induced pluripotent stem cell lines derived from human somatic cells." science 318.5858 (2007): 1917-1920.
Yu, X. et al, Adsorption of heavy metal ions from aqueous solution by carboxylated cellulose nanocrystals. J. Environ. Sci. 25, 933-943 (2013).
Zhang, H. G. et al, Glutamic acid-mediated synthesis of ultralong hydroxyapatite nanoribbons under hydrothermal conditions. Chem. Lett. 34, 788-789 (2005).
Zhang, Q.G. et al Ultrathin freestanding nanoporous membranes prepared from polystyrene nanoparticles. J. Mater. Chem. 21, 1684-1688 (2011).
Zhang, Q.G. et al, Sub-10 nm wide cellulose nanofibers for ultrathin nanoporous membranes with high organic permeation. Adv. Funct. Mater. 26, 792-800 (2016).
Zhao, G. et al, Few-layered graphene oxide nanosheets as superior sorbents for heavy metal ion pollution management. Environ. Sci. Technol. 45, 10454-10462 (2011).
Zhou, Y. et al, Preparation of a novel core-shell nanostructured gold colloid-silk fibroin bioconjugate by the protein redox technique at room temperature. Chem. Commun. 23, 2518-2519 (2001).
Koley, P. et al, Facile fabrication of silk protein sericin-mediated hierarchical hydroxyapatite-based bio-hybrid architectures: excellent adsorption of toxic heavy metals and hazardous dye from wastewater. Rsc Adv. 6, 86607-86616 (2016).
Kowshik, M. et al, Microbial synthesis of semiconductor PbS nanocrystallites. Adv. Mater. 14, 815-818 (2002).
Krieg, E. et al, A recyclable supramolecular membrane for size-selective separation of nanoparticles. Nat. Nanotechnol. 6, 141-146 (2011).
Lee Y.M. et al., Nanomesh-structured ultrathin membranes harnessing the unidirectional alignment of viruses on a graphene-oxide film. Adv. Mater. 26, 3899-3904 (2014).
Li, C. et al., Amyloid-hydroxyapatite bone biomimetic composites. Adv. Mater. 26, 3207-3212 (2014).
Li, Y. et al. Layer-by-layer assembly for rapid fabrication of thick polymeric films. Chem. Soc. Rev. 41, 5998-6009 (2012).
Li, Y.-H. et al, Adsorption of cadmium(II) from aqueous solution by surface oxidized carbon nanotubes. Carbon 41, 1057-1062 (2003).
Li, Y.-H. et al, Adsorption thermodynamic, kinetic and desorption studies of Pb2+ on carbon nanotubes. Water Res. 39, 605-609 (2005).
Li, Y.-H. et al, Competitive adsorption of Pb2+, Cu2+ and Cd2+ ions from aqueous solutions by multiwalled carbon nanotubes. Carbon 41, 2787-2792 (2003).
Li, Y.-H. et al, Lead adsorption on carbon nanotubes. Chem. Phys. Lett. 357, 263-266 (2002).
Liang H.W. et al., Carbonaceous nanofiber membranes for selective filtration and separation of nanoparticles. Adv. Mater. 22, 4691-4695 (2010).
Liang, P. et al, Multiwalled carbon nanotubes as solid-phase extraction adsorbent for the preconcentration of trace metal ions and their determination by inductively coupled plasma atomic emission spectrometry. J. Anal. At. Spectrom. 19, 1489-1492 (2004).
Lin, T.-J., Accurate force field parameters and pH resolved surface models for hydroxyapatite to understand structure, mechanics, hydration, and biological interfaces. J. Phys. Chem. C 120, 4975-4992 (2016).
Ling et al., Modulating materials by orthogonally oriented ß-strands: composites of amyloid and silk fibroin fibrils. Adv. Mater. 26, 4569-4574 (2014).
Ling, et al., Directed Growth of Silk Nanofibrils on Graphene and Their Hybrid Nanocomposites, ACS Macro Lett., vol. 3, Jan. 14, 2014, pp. 146-152.
Ling, S. et al, Liquid exfoliated natural silk nanofibrils: Applications in optical and electrical devices. Adv. Mater. 28, 7783-7790 (2016).
Ling, S. et al, Synchrotron FTIR microspectroscopy of single natural silk fibers. Biomacromolecules 12, 3344-3349 (2011).
Ling, S. et al, Ultrathin free-standing Bombyx mori silk nanofibril membranes. Nano Lett. 16, 3795-3800 (2016).
Liu, X. et al, Size-Selective Transport of uncharged solutes through multilayer polyelectrolyte membranes. Chem. Mater. 16, 351-357 (2004).
Lu, C. et al, Adsorption of zinc(II) from water with purified carbon nanotubes. Chem. Eng. Sci. 61, 1138-1145 (2006).
Lu, C. et al, Removal of nickel(II) from aqueous solution by carbon nanotubes. J. Chem. Technol. Biotechnol. 81, 1932-1940 (2006).
Lu, Y. et al. Nanofiltration membranes based on rigid star amphiphiles. Chem. Mater. 19, 3194-3204 (2007).
Matsumoto, T. et al, Crystallinity and solubility characteristics of hydroxyapatite adsorbed amino acid. Biomaterials 23, 2241-2247 (2002).
Meier, C. et al, Wet-spinning of amyloid protein nanofibers into multifunctional high-performance biofibers. Biomacromolecules 12, 3453-3459 (2011).

(56) References Cited

OTHER PUBLICATIONS

Mourhatch, R. et al, Network model for the evolution of the pore structure of silicon-carbide membranes during their fabrication. J. Membr. Sci. 356, 138-146 (2010).
Numata, K. et al, Mechanism of enzymatic degradation of beta-sheet crystals. Biomaterials 31, 2926-2933 (2010).
Omenetto, F.G. et al "New opportunities for an ancient material." Science 329.5991 (2010): 528-531.
Pakarinen, J. et al., Behavior of silicasupported manganese oxides in hydrometallurgical separations. Sep. Sci. Technol. 44, 3045-3074 (2009).
Pakarinen, J. et al., Nanoporous manganese oxides as environmental protective materials—Effect of Ca and Mg on metals sorption. J. Hazard. Mater. 180, 234-240 (2010).
Peetermans et al., Stability of freeze-dried rubella virus vaccine (Cendehill strain) at various temperatures, 1 J. Biological Standardization 179 (1973).
Peng, X. et al. Ultrafast permeation of water through protein-based membranes. Nat. Nanotechnol. 4, 353-357 (2009).
Peng, X. S. et al, Mesoporous separation membranes of polymer-coated copper hydroxide nanostrands. Adv. Funct. Mater. 17, 1849-1855 (2007).
Plimpton S., Fast parallel algorithms for short-range molecular dynamics. J. Comput. Phys. 117, 1-19 (1995).
Pu, X L.. et al, g-MPTMS modified nanometer-sized alumina micro-column separation and preconcentration of trace amounts of Hg, Cu, Au and Pd in biological, environmental and geological samples and their determination by inductively coupled plasma mass spectrometry. J. Anal. At. Spectrom. 19, 984-989 (2004).
Qin, Z. et al, Impact tolerance in mussel thread networks by heterogeneous material distribution. Nat. Commun. 4, 2187 (2013).
Qu, X. et al, Nanotechnology for a safe and sustainable water supply: enabling integrated water treatment and reuse. Acc. Chem. Res. 46, 834-843 (2013).
Rajkhowa, R. et al, An investigation into transition metal ion binding properties of silk fibers and particles using radioisotopes. J. Appl. Polym. Sci. 119, 3630-3639 (2011).
Reichert, J. et al., An evaluation of hydroxyapatite-based filters for removal of heavy metal ions from aqueous solutions. J Mater Sci 31, 1231-1241 (1996).
Richardson, J. J. et al., Technology-driven layer-by-layer assembly of nanofilms. Science 348, 2491 (2015).
Sashina, E. S., et al. "Structure and solubility of natural silk fibroin." Russian journal of applied chemistry 79.6 (2006): 869-876.
Shannon M.A. et al., Science and technology for water purification in the coming decades. Nature 452, 301-310 (2008).
Smuleac, V. et al, Layer-by-Layer-assembled microfiltration membranes for biomolecule immobilization and enzymatic catalysis. Langmuir 22, 10118-10124 (2006).
Striemer, C.C. et al, Charge- and size-based separation of macromolecules using ultrathin silicon membranes. Nature 445, 749-753 (2007).
Sun L.W. et al., Ultrafast molecule separation through layered WS2 nanosheet membranes. Acs Nano 8, 6304-6311 (2014).
Sun, L. et al, Laminar MoS2 membranes for molecule separation. Chem. Commun. 49, 10718-10720 (2013).
Takahashi K. et. al., "Induction of pluripotent stem cells from adult human fibroblasts by defined factors." cell 131.5 (2007): 861-872.
Takei, F., et al. "Further evidence for importance of the subunit combination of silk fibroin in its efficient secretion from the posterior silk gland cells." The Journal of cell biology 105.1 (1987): 175-180.
Tanaka, K. et al. "Immunological identification of the major disulfide-linked light component of silk fibroin." The Journal of Biochemistry 114.1 (1993): 1-4.
Tanaka, K., et al. "Determination of the site of disulfide linkage between heavy and light chains of silk fibroin produced by Bombyx mori." Biochimica et Biophysica Acta (BBA)-Protein Structure and Molecular Enzymology 1432.1 (1999): 92-103.

Tao, J. et al., Roles of amorphous calcium phosphate and biological additives in the assembly of hydroxyapatite nanoparticles. J. Phys. Chem. B 111, 13410-13418 (2007).
Afkhami, A. et al, Simultaneous removal of heavy-metal ions in wastewater samples using nano-alumina modified with 2,4-dinitrophenylhydrazine. J. Hazard. Mater. 181, 836-844 (2010).
Aksu Z., Determination of the equilibrium, kinetic and thermodynamic parameters of the batch biosorption of nickel(II) ions onto Chlorella vulgaris. Process Biochem. 38, 89-99 (2002).
Altman, G. H., et al. "Silk-based biomaterials." Biomaterials 24.3 (2003): 401-416.
Balachandra, A. M. et al, Enhancing the anion-transport selectivity of multilayer polyelectrolyte membranes by templating with $Cu^{2+}$. Macromolecules 35, 3171-3178 (2002).
Banerjee, I.A. et al, Cu nanocrystal growth on peptide nanotubes by biomineralization: Size control of Cu nanocrystals by tuning peptide conformation. Proc. Natl. Acad. Sci. U.S.A. 100, 14678-14682 (2003).
Bertaud, J. et al., Amino acid sequence dependence of nanoscale deformation mechanisms in alpha-helical protein filaments. J. Strain Anal. Eng. Des. 44, 517-531 (2009).
Bolisetty, S. et al, Amyloid-carbon hybrid membranes for universal water purification. Nat. Nanotechnol. 11, 365-371 (2016).
Borges, J. et al., Molecular interactions driving the layer-by-layer assembly of multilayers. Chem. Rev. 114, 8883-8942 (2014).
Braeken, L. et al, Flux decline in nanofiltration due to adsorption of dissolved organic compounds: Model prediction of time dependency. J. Phys. Chem. B 110, 2957-2962 (2006).
Brauman, K.A. et al, The nature and value of ecosystem services: an overview highlighting hydrologic services. Annu. Rev. Environ. Resour. 32, 67-98 (2007).
Cao, C.-Y. et al, Ceria hollow nanospheres produced by a template-free microwave-assisted hydrothermal method for heavy metal ion removal and catalysis. J. Phys. Chem. C 114, 9865-9870 (2010).
Chang, J., et al. "Nanomechanical stimulus accelerates and directs the self-assembly of silk-elastin-like nanofibers." Journal of the American Chemical Society 133.6 (2011): 1745-1747.
Chen, C. et al, Adsorption behavior of multiwall carbon nanotube/iron oxide magnetic composites for Ni(II) and Sr(II). J. Hazard. Mater. 164, 923-928 (2009).
Chen, C. et al, Adsorption of Ni(II) from aqueous solution using oxidized multiwall carbon nanotubes. Ind. Eng. Chem. Res. 45, 9144-9149 (2006).
Chen, P.-Y. et al, Biological materials: functional adaptations and bioinspired designs. Prog. Mater Sci. 57, 1492-1704 (2012). (in two parts due to file size).
Chen, Y.-H. et al, Kinetic study on removal of copper(II) using goethite and hematite nano-photocatalysts. J. Colloid Interface Sci. 347, 277-281 (2010).
Chen, Z. et al, Biosorption of nickel and copper onto treated alga (*Undaria pinnatifida*): Application of isotherm and kinetic models. J. Hazard. Mater. 155, 327-333 (2008).
Cheng, C. et al, Fundamentals of selective ion transport through multilayer polyelectrolyte membranes. Langmuir 29, 1885-1892 (2013).
Choi, H. et al, Nanocrystalline TiO2 photocatalytic membranes with a hierarchical mesoporous multilayer structure: synthesis, characterization, and multifunction. Adv. Funct. Mater. 16, 1067-1074 (2006).
Daniel, M.C. et al, Gold nanoparticles: Assembly, supramolecular chemistry, quantum-size-related properties, and applications toward biology, catalysis, and nanotechnology. Chem. Rev. 104, 293-346 (2004).
Deng C. et al., Ultrathin self-assembled anionic polymer membranes for superfast size-selective separation. Nanoscale 5, 11028-11034 (2013).
Eguizabal, A. et al, Nanoporous PBI membranes by track etching for high temperature PEMs. J. Membr. Sci. 454, 243-252 (2014).
Fang, G. et al, Formation of different gold nanostructures by silk nanofibrils. Mater. Sci. Eng. C 64, 376-382 (2016).
Farhat, T.R. et al, Doping-controlled ion diffusion in polyelectrolyte multilayers: mass transport in reluctant exchangers. J. Am. Chem. Soc. 125, 4627-4636 (2003).

(56) References Cited

OTHER PUBLICATIONS

Fei, X. et al, Green synthesis of silk fibroin-silver nanoparticle composites with effective antibacterial and biofilm-disrupting properties. Biomacromolecules 14, 4483-4488 (2013).

Fei, X. et al, Synthesis of hierarchical three-dimensional copper oxide nanostructures through a biomineralization-inspired approach. Nanoscale 5, 7991-7997 (2013).

Fu, F. et al, Removal of heavy metal ions from wastewaters: A review. J. Environ. Manage. 92, 407-418 (2011).

Galazka et al., Thermostability of vaccines, in Global Programme for Vaccines & Immunization (World Health Organization, Geneva, 1998).

Gao, S.J. et al, SWCNT-intercalated GO ultrathin films for ultrafast separation of molecules. J. Mater. Chem. A 3, 6649-6654 (2015).

Glavee, G. N. et al, Borohydride reduction of nickel and copper ions in aqueous and nonaqueous media. Controllable chemistry leading to nanoscale metal and metal boride particles. Langmuir 10, 4726-4730 (1994).

He, J. et al., Diffusion and filtration properties of self-assembled gold nanocrystal membranes. Nano Lett. 11, 2430-2435 (2011).

Hirota, M. et al, Surface carboxylation of porous regenerated cellulose beads by 4-acetamide-TEMPO/NaClO/NaClO2 system. Cellulose 16, 841-851 (2009).

Hokkanen, S. et al, A review on modification methods to cellulosebased adsorbents to improve adsorption capacity. Water Res. 91, 156-173 (2016).

Hokkanen, S. et al, Removal of heavy metals from aqueous solutions by succinic anhydride modified mercerized nanocellulose. Chem. Eng. J. 223, 40-47 (2013).

Hu, J. et al., Removal and recovery of Cr(VI) from wastewater by maghemite nanoparticles. Water Res. 39, 4528-4536 (2005).

Hu, J. et al., Selective removal of heavy metals from industrial wastewater using maghemite nanoparticle: Performance and mechanisms. J. Environ. Eng. 132, 709-715 (2006).

Hu, X.-J. et al, Removal of Cu(II) ions from aqueous solution using sulfonated magnetic graphene oxide composite. Sep. Purif. Technol. 108, 189-195 (2013).

Huang H. et al., Ultrafast viscous water flow through nanostrand-channelled graphene oxide membranes. Nat. Commun. 4, 2979 (2013).

International Agency for Research on Cancer, Agents Classified by the IARC Monographs (vols. 49 and 87) (International Agency for Research on Cancer, 2012); http://monographs.iarc.fr/ENG/Classification/.

International Searching Authority, International Search Report and Written Opinion for PCT/US2017/058134, dated Jan. 2, 2018, 8 pages.

Isobe, N. et al, TEMPO-oxidized cellulose hydrogel as a high-capacity and reusable heavy metal ion adsorbent. J. Hazard. Mater. 260, 195-201 (2013).

Jin, H-J. et al. "Mechanism of silk processing in insects and spiders." Nature 424.6952 (2003): 1057.

Joseph, N. et al, Layer-by-layer preparation of polyelectrolyte multilayer membranes for separation. Polym. Chem. 5, 1817-1831 (2014).

Joshi R.K. et al., Precise and ultrafast molecular sieving through graphene oxide membranes. Science 343, 752-754 (2014).

Jung, J.-M. et al., Liquid crystalline phase behavior of protein fibers in water: Experiments versus theory. Langmuir 26, 504-514 (2010).

Kabbashi, N.A. et al, Kinetic adsorption of application of carbon nanotubes for Pb(II) removal from aqueous solution. J. Environ. Sci. 21, 539-544 (2009).

Karan, S. et al, Ultrafast viscous permeation of organic solvents through diamond-like carbon nanosheets. Science 335, 444-447 (2012).

Karan, S. et al. Ultrathin free-standing membranes from metal hydroxide nanostrands. J. Membr. Sci. 448, 270-291 (2013).

Kikuchi, Y., et al. "Structure of the Bombyx mori fibroin light-chain-encoding gene: upstream sequence elements common to the light and heavy chain." Gene 110.2 (1992): 151-158.

Koivulaa, R. et al, Use of hydrometallurgical wastewater as a precursor for the synthesis of cryptomelane-type manganese dioxide ion exchange material. Sep. Purif. Technol. 70, 53-57 (2009).

\* cited by examiner

BIOMIMETIC MULTILAYER COMPOSITIONS

CROSS-REFERENCE TO RELATED APPLICATIONS

This application represents the national stage entry of PCT/US2017/058134, filed Oct. 24, 2017, which claims the benefit of U.S. Provisional Application 62/412,124 filed Oct. 24, 2016. The contents of these applications are hereby incorporated by reference as set forth in their entirety herein.

STATEMENT REGARDING FEDERALLY SPONSORED RESEARCH

This invention was made with government support under NIH Grant No. U01 EB014976 awarded by the National Institutes of Health, ONR Grant No. N00014-16-1-2333 awarded by the U.S. Navy, AFOSR Grant No. FA9550-11-1-0199 awarded by U.S. Air Force. The U.S. government has certain rights in the invention.

BACKGROUND

Purification, particularly of aqueous solutions, is critical in several industrial processes, as well as for basic life sustaining processes (e.g., water purification for drinking). While a variety of products are available, each has problems with one or more of efficiency, cost, and longevity. In addition, current products often are only suitable for a single type of purification and are often not reusable. What is needed are improved purification compositions and strategies.

SUMMARY

The present specification describes, among other things, technologies including new and optimized biomimetic routes to fabricate biomaterial-based multilayer membranes, for example for purification (e.g., filtration) or aqueous solutions. Surprisingly, the present inventors found that the use of weakly associated nanofibrils and nanocrystals allow for the formation of highly ordered networks useful for, inter alia, purification (e.g., filtration) or aqueous solutions. Accordingly, in various embodiments, provided compositions include little or no chemical interaction, rather, simple physical association is used. In some embodiments, provided compositions may include multilayer membranes with well-organized multilayer structures, e.g., through silk nanofibrils (SNF) self-assembly and in-situ hydroxyapatite (HAP) biomineralization. For example, in some embodiments, provided compositions (e.g., low-cost SNF/HAP membranes) may exhibit universal water purification capability, including for dyes, proteins and nano-colloids. Moreover, in some embodiments, provided compositions (e.g., membranes) can be formed from SNF/HAP dispersions under a short processing time, enabling the fabrication of multi-type purification membranes, such as pressure-derived filtration membranes and syringe ultrafilters. Additionally or alternatively, provided compositions, such as SNF/HAP membranes, can be used to remove metal ions from an aqueous solution, which may not be possible using other nanofiltration membranes. The metal ion contaminants that are removed can also be reused or recycled by simple, green routes, to avoid secondary pollutants. The technologies described herein may have a range of potential applications, such as waste-water treatment, nanotechnology, food industry and life sciences.

In some embodiments, the present invention provides compositions including at least one pliable layer comprising a plurality of silk fibroin nanofibrils, and at least one rigid layer comprising a plurality of mineral crystals, wherein each rigid layer is associated with at least one pliable layer. In some embodiments, a composition may be or comprise a film/membrane, a tube, a powder, a fiber (e.g., electrospun fiber, non-woven fiber), and/or a foam.

In some embodiments, the present invention also provides methods of making provided compositions. In some embodiments, the present invention provides methods including the steps of providing silk fibroin nanofibrils in at least one pliable layer, growing a plurality of mineral crystals on the silk fibroin nanofibrils such that the crystals form at least one rigid layer, and forming an insoluble membrane. In some embodiments, the forming occurs via one or more of vacuum filtration, injection, cylinder extrusion, and compression.

In some embodiments, at least one pliable layer of a provided composition is porous. In some embodiments, the pores have an average diameter between 1 and 20 nm (e.g., 3-15 nm). In some embodiments where there are two or more pliable layers, one layer may be porous where at least one other layer is substantially non-porous. In some embodiments where there are two or more pliable layers, each pliable layer is porous.

In some embodiments, at least one rigid layer is porous. In some embodiments, the pores have an average diameter between 5-100 nm (e.g., 10-50 nm). In some embodiments where there are two or more rigid layers, one layer may be porous where at least one other layer is substantially non-porous. In some embodiments where there are two or more rigid layers, each rigid layer is porous.

Any of a variety of peptide or protein-based nanofibrils may be useful in accordance with certain embodiments. In some embodiments, the pliable layer comprises one or more (e.g., two or more) of silk (e.g., silkworm silk, spider silk, recombinant silk), silk fibroin, silk-elastin, amyloid, collagen, nanochitin, nanocellulose, andsilaffin.

As is described herein, any of a variety of nanofibril dimensions are particularly suited for certain applications (e.g., wherein expected contaminants for removal are of a certain size or size range, for example). In some embodiments, the silk fibroin nanofibrils have an average aspect ratio of between 1:10 and 1:1,000. In some embodiments, nanofibrils are not spherical (e.g., not nanoparticles).

As described herein, the filtration characteristics of various embodiments varies based, inter alia, on the thickness of one of more of the pliable layers in a provided composition. In some embodiments, at least one pliable layer has a thickness between 10 nm and 1,000 um.

As described herein, the filtration characteristics of various embodiments varies based, inter alia, on the thickness of one of more of the rigid layers in a provided composition. In some embodiments, at least one rigid layer has a thickness between 10 nm and 1,000 um.

As described herein, any of a variety of mineral crystals are contemplated as within the scope of the present invention. Selection of particular mineral crystals may depend on the intended use of a particular embodiment. Parameters which would be considered by one of skill in the art in selecting the appropriate mineral crystal for particular rigid layer(s), include, but are not limited to desired size of the crystals, desired load bearing capacity of the crystals or composition, and ability to interest (or not interact) with particular contaminants in a solution. In some embodiments, the mineral crystals are or comprise calcium nanocrystals, titanium nanocrystals (e.g., for medical implants), gold nanocrystals (e.g., modulating heating capacity), silver nanocrystals (e.g., antimicrobial applications), graphene nanocrystals, graphene oxide nanocrystals, silica nanoparticles, or any other reactive inorganic material (e.g., catalysis, self-cleaning). In some embodiments, the calcium nanocrystals are hydroxyapatite crystals or calcium carbonate crystals.

As is described herein, pliable and/or rigid layers of provided compositions may be formed via any appropriate method. For example, in some embodiments, at least one layer of the composition is formed via one or more of vacuum filtration, injection, cylinder extrusion, and compression.

As is described herein, provided compositions comprising 2 or more pliable layers and/or two or more rigid layers are specifically contemplated and highly desirable in certain embodiments. For example, in some embodiments, a composition comprises at least two pliable layers (e.g., at least 3, 4, 5, 6, 7, 8, 9, 10 or more pliable layers). By way for further example, in some embodiments, a composition comprises at least two rigid layers (e.g., at least 3, 4, 5, 6, 7, 8, 9, 10 or more rigid layers).

In some embodiments, a provided composition may be substantially insoluble (e.g., in an aqueous solution). In some embodiments, a provided composition may be at least partially soluble (e.g., in an aqueous solution). In some embodiments, a provided composition may be substantially fully soluble (e.g., in an aqueous solution), for example, in a multi-layer composition to facilitate a desired release profile on of one of one or more active agents.

As is described herein, in some embodiments, provided compositions may be useful for filtering any of a variety of potential contaminant(s) or other undesired component(s) from a solution (e.g., an aqueous solution). For example, in some embodiments, a provided composition may be useful for removing one or more heavy metals from a solution. In some embodiments, has a removal capacity for gold ($Au^{3+}$) of at least 130 mg/g of membrane. In some embodiments, a provided composition has a removal capacity for copper ($Cu^{2+}$) of at least 60 mg/g of membrane. In some embodiments, a provided composition has a removal capacity for nickel ($Ni^{2+}$) of at least 60 mg/g of membrane. In some embodiments, a provided composition has a removal capacity for chromium ($Cr^{3+}$) of at least 120 mg/g of membrane. In some embodiments, removal capacity is assessed at substantially atmospheric pressure.

As used in this application, the terms "about" and "approximately" are used as equivalents. Any citations to publications, patents, or patent applications herein are incorporated by reference in their entirety. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

DESCRIPTION OF THE DRAWING

The foregoing and other objects, aspects, features, and advantages of the present disclosure will become more apparent and better understood by referring to the following description taken in conjunction with the accompanying figures in which:

FIG. 11, panel a, shows a mesostructure of SNF/HAP solution after liquid nitrogen freezing and freeze drying. Panel b shows an enlarged segment of the image in FIG. 9a.

DEFINITIONS

Figure 1:
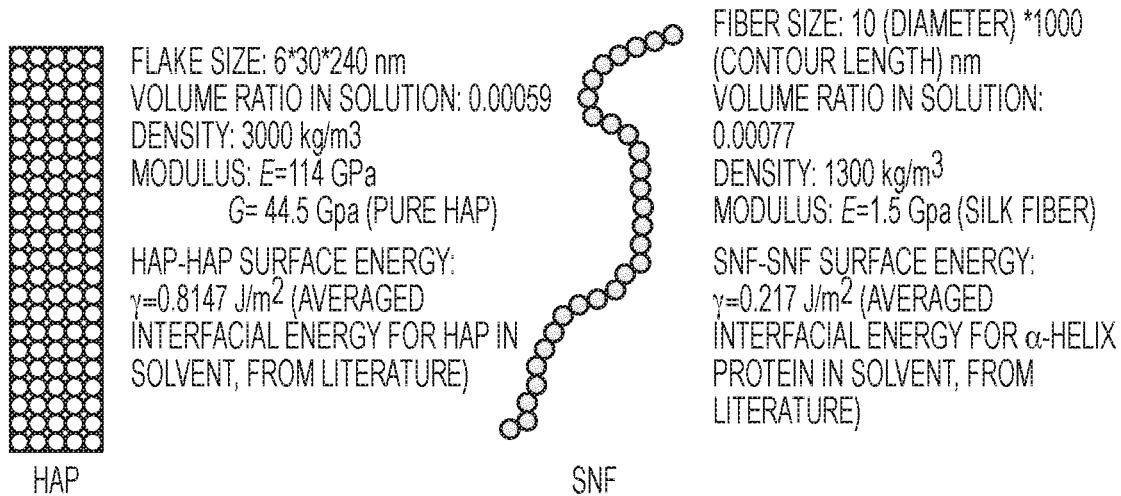
FIG. 1 shows a schematic figure of the coarse-grained computational model for HAP and SNF.

In order for the present disclosure to be more readily understood, certain terms are first defined below. Additional definitions for the following terms and other terms are set forth throughout the specification.

In this application, unless otherwise clear from context, the term "a" may be understood to mean "at least one." As used in this application, the term "or" may be understood to mean "and/or." In this application, the terms "comprising" and "including" may be understood to encompass itemized components or steps whether presented by themselves or together with one or more additional components or steps. Where ranges are provided herein, the endpoints are included. As used in this application, the term "comprise" and variations of the term, such as "comprising" and "comprises," are not intended to exclude other additives, components, integers or steps.

"About": As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Associated": As used herein, the term "associated" typically refers to two or more entities in physical proximity with one another, either directly or indirectly (e.g., via one or more additional entities that serve as a linking agent), to form a structure that is sufficiently stable so that the entities remain in physical proximity under relevant conditions, e.g., physiological conditions. In some embodiments, associated entities are covalently linked to one another. In some embodiments, associated entities are non-covalently linked. In some embodiments, associated entities are linked to one another by specific non-covalent interactions (i.e., by interactions between interacting ligands that discriminate between their interaction partner and other entities present in the context of use, such as, for example. streptavidin/avidin interactions, antibody/antigen interactions, etc.). Alternatively or additionally, a sufficient number of weaker non-covalent interactions can provide sufficient stability for moieties to remain associated. Exemplary non-covalent interactions include, but are not limited to, affinity interactions, metal coordination, physical entrapment, physical adsorption, host-guest interactions, hydrophobic interactions, pi stacking interactions, hydrogen bonding interactions, van der Waals interactions, magnetic interactions, electrostatic interactions, dipole-dipole interactions, etc.

"Comparable": The term "comparable", as used herein, refers to two or more agents, entities, situations, sets of conditions, etc. that may not be identical to one another but that are sufficiently similar to permit comparison there between so that conclusions may reasonably be drawn based on differences or similarities observed. Those of ordinary skill in the art will understand, in context, what degree of identity is required in any given circumstance for two or more such agents, entities, situations, sets of conditions, etc. to be considered comparable.

"Porosity": The term "porosity" as used herein, refers to a measure of void spaces in a material and is a fraction of volume of voids over the total volume, as a percentage between 0 and 100%. A determination of porosity is known to a skilled artisan using standardized techniques, for example mercury porosimetry and gas adsorption (e.g., nitrogen adsorption).

"Protein": As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

"Reference": As used herein describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

"Small molecule": As used herein, the term "small molecule" is used to refer to molecules, whether naturally-occurring or artificially created (e.g., via chemical synthesis), having a relatively low molecular weight and being an organic and/or inorganic compound. Typically, a "small molecule" is monomeric and have a molecular weight of less than about 1500 g/mol. In general, a "small molecule" is a molecule that is less than about 5 kilodaltons (kD) in size. In some embodiments, a small molecule is less than about 4 kD, 3 kD, about 2 kD, or about 1 kD. In some embodiments, the small molecule is less than about 800 daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol. In some embodiments, a small molecule is not a polymer. In some embodiments, a small molecule does not include a polymeric moiety. In some embodiments, a small molecule is not a protein or polypeptide (e.g., is not an oligopeptide or peptide). In some embodiments, a small molecule is not a polynucleotide (e.g., is not an oligonucleotide). In some embodiments, a small molecule is not a polysaccharide. In some embodiments, a small molecule does not comprise a polysaccharide (e.g., is not a glycoprotein, proteoglycan, glycolipid, etc.).

"Solution": As used herein, the term "solution" broadly refers to a homogeneous mixture composed of one phase. Typically, a solution comprises a solute or solutes dissolved in a solvent or solvents. It is characterized in that the properties of the mixture (such as concentration, temperature, and density) can be uniformly distributed through the volume. In the context of the present application, therefore, a "silk fibroin solution" refers to silk fibroin protein in a soluble form, dissolved in a solvent, such as water. In some embodiments, silk fibroin solutions may be prepared from a solid-state silk fibroin material (i.e., silk matrices), such as silk films and other scaffolds. Typically, a solid-state silk fibroin material is reconstituted with an aqueous solution, such as water and a buffer, into a silk fibroin solution. It should be noted that liquid mixtures that are not homogeneous, e.g., colloids, suspensions, emulsions, are not considered solutions.

"Substantially": As used herein, the term "substantially", and grammatical equivalents, refer to the qualitative condition of exhibiting total or near-total extent or degree of a characteristic or property of interest. One of ordinary skill in the art will understand that biological and chemical phenomena rarely, if ever, go to completion and/or proceed to completeness or achieve or avoid an absolute result.

DETAILED DESCRIPTION

The present invention encompasses a surprising recognition that the loose association of particular materials (e.g., polymers and mineral crystals) can allow for compositions with highly useful properties. In some embodiments, provided compositions may be useful for the purification (e.g., filtration) of liquids/solutions. In some embodiments, liquids may be or comprise aqueous liquids. In some embodiments, liquids may be or comprise organic liquids. In some embodiments, provided compositions are able to filter one or more contaminants out of a liquid significantly faster than previous technologies. In some embodiments, provided compositions are able to filter one or more contaminants out of a liquid significantly more efficiently than previous technologies. In some embodiments, provided compositions are able to filter one or more contaminants out of a liquid and allow for the reuse of one or more thereof (something not necessarily possible using existing technologies). As used herein, the term "contaminant" means a substance present in a liquid that is undesired. A contaminant in one situation or liquid may be highly desired in another situation or liquid and, as such, the use of the term contaminant is not meant to refer only to harmful substances or those without a valuable use.

In some embodiments, the present invention provides compositions including at least one pliable layer comprising a plurality of silk fibroin nanofibrils, and at least one rigid layer comprising a plurality of mineral crystals, wherein each rigid layer is associated with at least one pliable layer.

In some embodiments, the present invention also provides methods of making provided compositions. In some embodiments, the present invention provides methods including the steps of providing silk fibroin nanofibrils in at least one pliable layer, growing a plurality of mineral crystals on the silk fibroin nanofibrils such that the crystals form at least one rigid layer, and forming an insoluble membrane.

Pliable Layers

As described herein, provided compositions comprise at least one pliable layer. In some embodiments, provided compositions comprise two or more pliable layers (e.g., 2, 3, 4, 5, 6, 7, 8, 9, 10 or more pliable layers). In accordance with several embodiments, a pliable layer may include pores of a relatively small size, for example, an average diameter between 1-20 nm (e.g., 1-15 nm, 1-10 nm, 1-5 nm, 2-20 nm, 3-15 nm, 5-20 nm, 5-15 nm, 5-10 nm, or 10-20 nm).

Nanofibrils

In some embodiments, a pliable layer may comprise a plurality of nanofibrils. Any of a variety of nanofibril structures are contemplated as within the scope of the present invention. For example, in some embodiments, a nanofibril may have an aspect ratio of between 1:10 and 1:1,000 (e.g., 1:10-1:900, 1:10-1:800, 1:10-1:700, 1:10-1:600, 1:10-1:500, 1:10-1:400, 1:10-1:300, 1:10-1:200, 1:10-1:100, 1:50-1:1,000, 1:50-1:500, 1:100-1:1,000, or 1:100-1:500). In some embodiments, a nanofibril may have an aspect ratio of at least 1:10 (e.g., at least 1:20, 1:30, 1:40, 1:50, 1:60, 1:70, 1:80, 1:90, etc)

In some embodiments, a nanofibril may have a diameter between 1-100 nm (e.g., 1-90 nm, 1-80 nm, 1-70 nm, 1-60 nm, 1-50 nm, 1-40 nm, 1-30 nm, 1-20 nm, 1-10 nm, 2-100 nm, 5-100 nm, 5-90 nm, 5-80 nm, 5-70 nm, 5-60 nm, 5-50 nm, 10-100 nm, 20-100 nm, 30-100 nm, 40-100 nm, or 50-100 nm). In some embodiments, a nanofibril may have a diameter of at least 1 nm (e.g., at least 5 nm, 10 nm, 20 nm, 30 nm, 40 nm, 50 nm, 60 nm, 70 nm, 80 nm, 90 nm, etc). In some embodiments, a nanofibril may have a diameter of at most 100 nm (e.g., at most 90 nm, 80 nm, 70 nm, 60 nm, 50 nm, 40 nm, 30 nm, 20 nm, etc)

In some embodiments, a nanofibril may have a length of between 100 nm-10 um (e.g., 100 nm-5 um, 100 nm-1 um, 100 nm-900 nm, 100 nm-800 nm, 100 nm-700 nm, 100 nm-600 nm, 100 nm-500 nm, 200 nm-10 um, 200 nm-1 um, 200 nm-900 nm, 200 nm-800 nm, 200 nm-700 nm, 200 nm-600 nm, 200 nm-500 nm, 500 nm-10 um, 500 nm-1 um, or 500 nm-900 nm). In some embodiments, a nanofibril may have a length of at least 100 nm (e.g., at least 200 nm, 300 nm, 400 nm, 500 nm, 600 nm, 700 nm, 800 nm, 900 nm, etc). In some embodiments a nanofibril may have a length of at most 10 um (e.g., at most 5 um, 1 um, 900 nm, 800 nm, 700 nm, 600 nm, 500 nm, etc)

According to various embodiments, nanofibrils may be or comprise any of a variety of materials. By way of non-limiting example, in some embodiments, nanofibrils may be or comprise at least one of silk (e.g., silkworm silk, spider silk, recombinant silk), silk fibroin, silk-elastin, amyloid, collagen, nanochitin, nanocellulose, and silaffin.

As described herein, including in the examples below, nanofibrils may be provided in any application-appropriate way. For example, in some embodiments, nanofibrils may be provided/created by incubating degummed silk fibers (e.g., a silk fibroin solution of 1 wt % silk or less) at an elevated temperature (e.g., greater than 40° C., for example 60° C. to 90° C.) for a period of time (e.g., 1 day or more, for example, 7 days). In addition, techniques for forming silk fibroin nanofibrils may be found in PCT Application Publication No. PCT/US17/44960 or PCT/US13/35389, the disclosures of which are hereby incorporated by reference.

In accordance with various embodiments, a pliable layer may be made in a variety of thickness. In some embodiments, the thickness of a pliable layer may be tailored to a particular application. For example, in certain applications, it may be advantageous to use at least one relatively thicker pliable layer (e.g., 100 nm or greater) in order to provide desired mechanical and/or functional characteristics. By way of additional example, in certain applications, it may be advantageous to use at least one relatively thinner pliable layer (e.g., less than 100 nm). In some embodiments, a pliable layer may have a thickness between 10 nm and 100 um.

Silk Fibroin

In some embodiments, a nanofibril is or comprises a silk polypeptide, such as a silk fibroin polypeptide. In nature, silk is produced as protein fiber, typically made by specialized glands of animals, and often used in nest construction. Organisms that produce silk include the Hymenoptera (bees, wasps, and ants and other types of arthropods, most notably various arachnids such as spiders (e.g., spider silk), also produce silk. Silk fibers generated by insects and spiders represent the strongest natural fibers known and rival even synthetic high performance fibers.

The first reported examples of silk being used as a textile date to ancient China (see Elisseeff, "The Silk Roads: Highways of Culture and Commerce," Berghahn Books/UNESCO, New York (2000); see also Vainker, "Chinese Silk: A Cultural History," Rutgers University Press, Piscataway, N.J. (2004)); it has been highly prized in that industry ever since. Indeed, silk has been extensively investigated for its potential in textile, biomedical, photonic and electronic applications. Glossy and smooth, silk is favored by not only fashion designers but also tissue engineers because it is mechanically tough but degrades harmlessly inside the body, offering new opportunities as a highly robust and biocompatible material substrate (see Altman et al., Biomaterials, 24: 401 (2003); see also Sashina et al., Russ. J. Appl. Chem., 79: 869 (2006)). Thus, even among biocompatible polymers (and particularly among biocompatible polypeptides, including natural polypeptides), silk and silk polypeptides are of particular interest and utility.

Silk fibroin is a polypeptide, like collagen, but with a unique feature: it is produced from the extrusion of an amino-acidic solution by a living complex organism (while collagen is produced in the extracellular space by self-assembly of cell-produced monomers). Silk is naturally produced by various species, including, without limitation: *Antheraea mylitta; Antheraea pernyi; Antheraea yamamai; Galleria mellonella; Bombyx mori; Bombyx mandarina; Galleria mellonella; Nephila clavipes; Nephila senegalensis; Gasteracantha mammosa; Argiope aurantia; Araneus diadematus; Latrodectus geometricus; Araneus bicentenarius; Tetragnatha versicolor; Araneus ventricosus; Dolomedes tenebrosus; Euagrus chisoseus; Plectreurys tristis; Argiope trifasciata*; and *Nephila madagascariensis*. Embodiments of the present disclosure may utilize silk proteins from any such organism. In some embodiments, the present disclosure utilizes silk or silk proteins from a silkworm, such as *Bombyx mori* (e.g., from cocoons or glands thereof). In some embodiments, the present disclosure utilizes silks or silk proteins from a spider, such as *Nephila clavipes* (e.g., from nests/webs or glands thereof).

In general, silk polypeptides for use in accordance with the present disclosure may be or include natural silk polypeptides, or fragments or variants thereof. In some embodiments, such silk polypeptides may be utilized as natural silk, or may be prepared from natural silk or from organisms that produce it. Alternatively, silk polypeptides utilized in the present disclosure may be prepared through an artificial process, for example, involving genetic engineering of cells or organisms (e.g., genetically engineered bacteria, yeast, mammalian cells, non-human organisms, including animals, or transgenic plants) to produce a silk polypeptide, and/or by chemical synthesis.

In some particular embodiments, silk polypeptides are obtained from cocoons produced by a silkworm, in certain embodiments by the silkworm *Bombyx mori*; such cocoons are of particular interest as a source of silk polypeptide because they offer low-cost, bulk-scale production of silk polypeptides. Moreover, isolation methodologies have been developed that permit preparation of cocoon silk, and particularly of *Bombyx mori* cocoon silk in a variety of forms suitable for various commercial applications.

Silkworm cocoon silk contains two structural proteins, the fibroin heavy chain (~350 kDa) and the fibroin light chain (~25 kDa), which are associated with a family of non-structural proteins termed sericins, that glue the fibroin chains together in forming the cocoon. The heavy and light fibroin chains are linked by a disulfide bond at the C-terminus of the two subunits (see Takei, et al. J. Cell Biol., 105: 175, 1987; see also Tanaka, et al J. Biochem. 114: 1, 1993; Tanaka, et al Biochim. Biophys. Acta., 1432: 92, 1999; Kikuchi, et al Gene, 110: 151, 1992). The sericins are a high molecular weight, soluble glycoprotein constituent of silk which gives the stickiness to the material. These glycoproteins are hydrophilic and can be easily removed from cocoons by boiling in water. This process is often referred to as "degumming." In some embodiments, silk polypeptide compositions utilized in accordance with the present disclosure are substantially free of sericins (e.g., contain no detectable sericin or contain sericin at a level that one of ordinary skill in the pertinent art will consider negligible for a particular use).

To give but one particular example, in some embodiments, silk polypeptide compositions for use in accordance with the present disclosure are prepared by processing cocoons spun by silkworm, *Bombyx mori* so that sericins are removed and silk polypeptides are solubilized. In some such embodiments, cocoons are boiled (e.g., for a specified length of time, often approximately 30 minutes) in an aqueous solution (e.g., of 0.02 M $Na_2CO_3$), then rinsed thoroughly with water to extract the glue-like sericin proteins. Extracted silk is then dissolved in a solvent, for example, LiBr (such as 9.3 M). A resulting silk fibroin solution can then be further processed for a variety of applications as described elsewhere herein.

In some embodiments, silk polypeptide compositions for use in the practice of the present disclosure comprise silk fibroin heavy chain polypeptides and/or silk fibroin light chain polypeptides; in some such embodiments, such compositions are substantially free of any other polypeptide. In some embodiments that utilize both a silk fibroin heavy chain polypeptide and a silk fibroin light chain polypeptide, the heavy and light chain polypeptides are linked to one another via at least one disulfide bond. In some embodiments, where the silk fibroin heavy and light chain polypeptides are present, they are linked via one, two, three or more disulfide bonds.

Exemplary natural silk polypeptides that may be useful in accordance with the present disclosure may be found in International Patent Publication Number WO 2011/130335, International Patent Publication Number WO 97/08315 and/or U.S. Pat. No. 5,245,012, the entire contents of each of which are incorporated herein by reference.

Silk fibroin polypeptides are characterized by a structure that typically reflects a modular arrangement of large hydrophobic blocks staggered by hydrophilic, acidic spacers, and, typically, flanked by shorter (~100 amino acid), often highly conserved, terminal domains (at one or both of the N and C termini). In many embodiments, the hydrophobic blocks comprise or consist of alanine and/or glycine residues; in some embodiments alternating glycine and alanine; in some embodiments alanine alone. In many embodiments, the hydrophilic spacers comprise or consist of amino acids with bulky side-groups. Naturally occurring silk fibroin polypeptides often have high molecular weight (200 to 350 kDa or higher) with transcripts of 10,000 base pairs and higher and >3000 amino acids (reviewed in Omenetto and Kaplan (2010) Science 329: 528-531).

In some embodiments, a fibroin polypeptide contains multiple hydrophobic blocks, e.g., 3, 4, 5, 6, 7, 8, 9, 10, 11, 12, 13, 14, 15, 16, 17, 18, 19 and 20 hydrophobic blocks within the polypeptide. In some embodiments, a fibroin polypeptide contains between 4-17 hydrophobic blocks. In some embodiments, a fibroin polypeptide comprises at least one hydrophilic spacer sequence ("hydrophilic block") that is about 4-50 amino acids in length.

It is generally believed that features of silk fibroin polypeptide structure contribute to the material properties and/or functional attributes of the polypeptide. For example, sequence motifs such as poly-alanine (polyA) and polyalanine-glycine (poly-AG) are inclined to be beta-sheet-forming; the presence of one or more hydrophobic blocks as described herein therefore may contribute to a silk polypeptide's ability to adopt a beta-sheet conformation, and/or the conditions under which such beta-sheet adoption occurs.

In some embodiments, the silk fiber can be an unprocessed silk fiber, e.g., raw silk or raw silk fiber. The term "raw silk" or "raw silk fiber" refers to silk fiber that has not been treated to remove sericin, and thus encompasses, for example, silk fibers taken directly from a cocoon. Thus, by unprocessed silk fiber is meant silk fibroin, obtained directly from the silk gland. When silk fibroin, obtained directly from the silk gland, is allowed to dry, the structure is referred to as silk I in the solid state. Thus, an unprocessed silk fiber comprises silk fibroin mostly in the silk I conformation (a helix dominated structure). A regenerated or processed silk fiber on the other hand comprises silk fibroin having a substantial silk II (a β-sheet dominated structure).

Inducing a conformational change in silk fibroin can facilitate formation of a solid-state silk fibroin and/or make the silk fibroin at least partially insoluble. Further, inducing formation of beta-sheet conformation structure in silk fibroin can prevent silk fibroin from contracting into a compact structure and/or forming an entanglement. In some embodiments, a conformational change in the silk fibroin can alter the crystallinity of the silk fibroin in the silk particles, such as increasing crystallinity of the silk fibroin, e.g., silk II beta-sheet crystallinity. In some embodiments, the conformation of the silk fibroin in a provided composition can be altered after formation.

In some embodiments, provided compositions as disclosed herein may possess some degree of silk II beta-sheet crystallinity. In some embodiments, provided nanofibrils may comprise at least 10% beta-sheet (e.g., at least 20%, 30%, 40%, 50%, 60%, 70%, 80%, 90%, 95% or more). In some embodiments, provided nanofibrils may comprise a beta-sheet content of between 40-80% (e.g., between 50-70%).

In some embodiments, physical properties of silk fibroin can be modulated when selecting and/or altering a degree of crystallinity of silk fibroin. In some physical properties of silk fibroin include, for example, mechanical strength, degradability, and/or solubility. In some embodiments, inducing a conformational change in silk fibroin can alter the rate of release of an active agent from the silk matrix.

In some embodiments, a conformational change can be induced by any methods known in the art, including, but not limited to, alcohol immersion (e.g., ethanol, methanol), water annealing, water vapor annealing, heat annealing, shear stress (e.g., by vortexing), ultrasound (e.g., by sonication), pH reduction (e.g., pH titration), and/or exposing the silk particles to an electric field and any combinations thereof.

In accordance with various embodiments, any of a variety of silk concentrations may be used in making a provided layer or composition. For example, in some embodiments, a pliable layer may comprise between 0.01-5 wt % silk fibroin (e.g., 0.1-5 wt %, 0.01-1 wt %, 0.1-1 wt %). In some embodiments, a pliable layer may comprise less than 1 wt % silk fibroin.

Silk-Elastin

In some embodiments, a nanofibril may be or comprise a silk-elastin nanofibril. More information about silk-elastin nanofibrils, including methods for making them, may be found in Chang et al., J. Am. Chem. Soc. 2011 Feb. 16; 133(6): 1745-1747, the disclosure of which is hereby incorporated by reference in its entirety.

Rigid Layers

As described herein, provided compositions comprise at least one rigid layer. In some embodiments, provided compositions comprise two or more rigid layers (e.g., 2, 3, 4, 5, 6, 7, 8, 9, 10 or more rigid layers). In accordance with several embodiments, a rigid layer may include pores of a relatively large size, as compared to the pliable layer, for example. In some embodiments, a rigid layer may include pores having an average diameter of between 10-500 nm (e.g., 10-400 nm, 10-300 nm, 10-200 nm, 10-100 nm, 10-50 nm, 20-500 nm, 20-400 nm, 20-300 nm, 20-200 nm, 20-100 nm, 30-500 nm, 40-500 nm, 50-500 nm, 60-500 nm, 70-500 nm, 80-500 nm, 90-500 nm, or 100-500 nm).

Mineral Crystals

In some embodiments, a rigid layer may comprise a plurality of mineral crystals. In accordance with various embodiments, any of a variety of mineral crystals may be used. Any of a variety of mineral crystal structures are contemplated as within the scope of the present invention. For example, in some embodiments, mineral crystals may be or comprise calcium-containing crystals (e.g., calcium nanocrystals), titanium or titanium-containing nanocrystals (e.g., for medical implants), gold or gold-containing nanocrystals (e.g., modulating heating capacity), silver or silver-containing nanocrystals (e.g., antimicrobial applications), graphene or graphene-containing nanocrystals, graphene oxide or graphene oxide-containing nanocrystals, silica or silica-containing nanoparticles, molybdenum disulfide-containing nanocrystals, tungsten disulfide-containing nanocrystals, montmorillonoid-containing nanocrystals, or any other reactive inorganic material (e.g., catalysis, self-cleaning). In some embodiments, where mineral crystals comprise calcium nanocrystals, calcium nanocrystals may be or comprise hydroxyapatite crystals or calcium carbonate crystals. In some embodiments, mineral crystals may be or comprise silica nanoparticles.

The dimensions of minerals crystal may also vary in accordance with a desired application of provided compositions. For example, in some embodiments, a mineral crystal may have a size (e.g., a width or diameter) between 1-1,000 nm (e.g., between 1-900 nm, 1-800 nm, 1-700 nm, 1-600 nm, 1-500 nm, 1-400 nm, 1-300 nm, 1-200 nm, 1-100 nm, 5-1,000 nm, 10-1,000 nm, 50-1,000 nm, 100-1,000 nm, 200-1,000 nm, 100-500 nm). In some embodiments, a mineral crystal may have a length of between 100 nm-10 um.

In accordance with various embodiments, mineral crystals may be formed through any application-appropriate process. For example, in some embodiments, mineral crystals may be formed through one or more of biomineralization (or a mimetic technique), thermal deposition, liquid exfoliation, extraction from organic sources (e.g., extraction from seashells followed by grinding), and/or water evaporation.

Association/Formation of Pliable and Rigid Layers

As discussed herein, in some embodiments, provided compositions comprise an association between the pliable layer(s) and rigid layer(s). In some embodiments, provided compositions comprise an association that comprises substantially no (or no) covalent bonding. In some embodiments, provided compositions comprise an association that comprises substantially no (or no) chemical interaction or crosslinking. In some embodiments, provided compositions include only a weak nanofibril/nanocrystal interaction (e.g., physical association such as wrapping, enveloping, or embedding of at least some of the mineral crystals in the nanofibrils).

Provided compositions (and the pliable and rigid layers therein) may be formed via any applicable process. For example, in some embodiments, a layer or composition may be formed by one or more of vacuum filtration, injection, spin coating, deposition, cylinder extrusion, and compression.

Provided Compositions

In accordance with various embodiments, certain provided compositions may be completely or substantially insoluble, for example, in an aqueous solution and/or an organic solution. In other embodiments, certain provided compositions may be partially or substantially soluble. By way of non-limiting example, in some embodiments, provided compositions (e.g., calcium-containing compositions) may dissolve in a low pH aqueous solution (e.g., less than 2). By way of additional example, in some embodiments, provided compositions (e.g., silk nanofibril-containing compositions) may dissolve in an organic solvent (e.g., 1,1,1,3,3,3-hexa-fluoro-2-propanol, also referred to as HFIP).

As is shown in the Examples below, in some embodiments, provided composition are useful in filtering out one or more contaminants from a liquid/solution. In some embodiments, a provided composition may be designed to filter out specific contaminants, for example, contaminants too large to pass through the relatively small pores of a pliable layer, or contaminants that are able to (or unable to) interact with the nanofibrils (e.g., silk fibroin nanofibrils) or mineral crystals (e.g., calcium-containing nanocrystals) of a particular embodiment. While any of a variety of contaminants may be purified or filtered out of a liquid by provided compositions, in some embodiments, a contaminant may be one or more of dye(s), heavy metal(s), a protein(s) or peptide(s), nanoparticles, small molecules, colloidal suspensions, and highly charged molecules.

In some embodiments, provided compositions may be useful in filtering one or more heavy metals out of a solution (e.g., an aqueous solution). In some embodiments, has a removal capacity for gold ($Au^{3+}$) of at least 130 mg/g of membrane. In some embodiments, a provided composition has a removal capacity for copper ($Cu^{2+}$) of at least 60 mg/g of membrane. In some embodiments, a provided composition has a removal capacity for nickel ($Ni^{2+}$) of at least 60 mg/g of membrane. In some embodiments, a provided composition has a removal capacity for chromium ($Cr^{3+}$) of at least 120 mg/g of membrane.

In some embodiments, provided compositions may exhibit a significantly higher flow rate (e.g., water flux) than previously existing technologies, for example, per unit of weight or surface area of the composition. In some embodiments, provided compositions may exhibit a flow rate or water flux of between 1,000 L $h^{-1}$ $m^{-2}$ $bar^{-1}$ to 15,000 L $h^{-1}$ $m^{-2}$ $bar^{-1}$ (e.g., 1,000 L $h^{-1}$ $m^{-2}$ $bar^{-1}$ to 10,000 L $h^{-1}$ $m^{-2}$ $bar^{-1}$, 1,000 L $h^{-1}$ $m^{-2}$ $bar^{-1}$ to 5,000 L $h^{-1}$ $m^{-2}$ $bar^{-1}$ or 5,000 L $h^{-1}$ $m^{-2}$ $bar^{-1}$ to 15,000 L $h^{-1}$ $m^{-2}$ $bar^{-1}$).

In accordance with various embodiments, provided compositions may take any application-appropriate form. For example, by way of specific example, in some embodiments, a composition may be or comprise one or more of a film, a membrane, a hydrogel, a tube, and/or a foam.

Previously, compositions (e.g., membranes) for fluid, e.g., water, treatment have been developed in recent years to address global challenges of water pollution, because they are energy- and waste-efficient to remove molecular-level contaminants. A variety of new materials (e.g., polymers, biopolymers, inorganic nanomaterials) and novel fabrication methods (e.g., block copolymer self-assembly, template synthesis, track-etching technique, chemical vapour deposition, and layer-by-layer assembly) have been developed to improve the purification efficiency of membranes. However, prior to the present invention, it remained challenging to prepare purification membranes, e.g., low-cost water purification membranes, while retaining mechanical strength and high purification performance.

Multilayer filtration compositions (e.g., membranes) have several advantages, including enhanced throughput, high filter efficiency, high molecular loading capacity and low pressure drop. Nature has utilized multilayer architectures for water purification for millions of years in environments consist of vegetation, gravel, sand and soil layers. When rainfall lands in forests, deserts and wetlands, the water soaks into the ground through the vegetation layer, where large soil particles are trapped by the gravel layer and the rainfall is further cleansed through fine layers of sand and soil (soil horizons). Layer-by-layer assembly is a method for building multilayer structures, but this approach comes with several drawbacks, such as limited material selectivity, a time-consuming and tedious process, and the relatively weak mechanical properties of the resultant membranes. A variety of laminar inorganic nanosheets, such as graphene oxide, molybdenum disulfide, and tungsten disulphide can be utilized for layered purification membranes. However, these membranes may not have nano-sized porous structures without complex and expensive processing. Water can only permeate from gaps and interlayer spaces between nanosheets, thus their permeation rate leaves significant room for improvement.

Besides laminar inorganic nanomaterials, biomaterials (e.g. cellulose, chitin and proteins) can been used for making filtration membranes. Liquid exfoliated silk nanofibrils (SNFs) can be used to make filtration membrane with high water flux and efficient separation performance for dyes, proteins and nanoparticles. However, a pristine SNF membrane, as with other biomaterial-based filtration systems, may have small and untunable pore sizes (e.g., 8-12 nm diameters in liquid exfoliated SNF membrane). Thus, water (and/or solvent) permeation rates may decline dramatically with increase of membrane thickness, and the molecular loading capacity for purification may also be limited. This problem can be mitigated, to some extent by combining different protein fibrils within the same membrane. For example, SNFs and amyloid fibrils can be integrated into a homogenous membrane, and amyloids from mature hybrid membranes can be enzymatically etched, resulting in tunable nanoporous structures. However, the stability and mechanical properties of the resultant membranes may require improvement for certain applications, e.g., the membranes with a high percentage of amyloids as well as those that have been enzymatic etched. Biomaterials can be useful to develop novel water treatment membranes, in part due to their advantages of cost-saving, environmental friendliness, and biocompatibility. However, it remains a challenge to efficiently and accurately produce multilayer porous structures of biomaterials to achieve optimized separation performance, mechanical resilience and stability.

As is described herein, among other things, the present invention provides technologies related to multilayer nanoporous membranes, for example technologies to produce multilayer nanoporous membranes designed via integration of computational simulation and experimental data. An example methodology uses soft/pliable and hard/rigid nano-building blocks for constructing multilayer nanoporous structures. In some embodiments, a soft nano-building block is or comprises one or more soft layers with a smaller pore size (e.g., several nanometers in diameter) that may serve as size-selectivity layers to effectively filter out objects, such as molecular level contaminants. In some embodiments, a hard nano-building block is or comprises one or more hard layer with a large pore size (e.g., 10-50 nanometers in diameter) and high porosity that may allow fluid (e.g., water) to pass through quickly, and may provide structural support to the soft layer. In addition, an alternating arrangement of these two layers can further improve permeability of these membranes. Many natural systems, such as nacre, enamel, or bone, use proteins and calcium-based minerals to build their sophisticated multilayer architectures with enhanced physical properties. and can be used as starting building blocks to generate composite membranes.

In some embodiments, provided compositions may further comprise a coating. In some embodiments, a coating covers or substantially covers at least one layer of a composition. In some embodiments, a coating covers all or substantially all of a provided composition. In some embodiments, a coating can be or comprise a hydrophilic coating, a hydrophobic coating, a soluble coating, an insoluble coating, a porous coating and/or a non-porous coating.

Active Agents

In accordance with certain embodiments, one or more active agents may be included in provided compositions. For example, in some embodiments, silk fibroin solutions used to make, inter alia, silk fibroin nanofibrils, may contain at least one active agent. The silk fibroin solution may be contacted with an active agent prior to forming a silk fibroin article, e.g. a pliable layer, or loaded into or onto the article after it is formed. For loading after formation, silk assembly may be used to control hydrophilic/hydrophobic partitioning (see, for example, Jin et al., Nature. 2003 Aug. 28; 424 (6952):1057-61) and the adsorption of phase separation of the active agent. In some embodiments, a composition or layer can also be loaded by entrapping the active agent in the silk by inducing the transition to the beta sheet (e.g. methanol, shear, salts, electric) and adding layers on this with each layer entrapping the next active agent. This layer-by-layer approach allows onion like structures with selective loading in each layer.

In some embodiments, any of a variety of different active agents that can be used in conjunction with the compositions of the present invention. The array of potential active agents compatible with various embodiments is vast, and includes small molecules, proteins, peptides and nucleic acids (e.g., single or double stranded DNA, RNA, or peptide nucleic acids [PNAs]).

An active agent can include a wide variety of different compounds, including chemical compounds and mixtures of chemical compounds, e.g., small organic or inorganic molecules; saccharines; oligosaccharides; polysaccharides; biological macromolecules, e.g., peptides, proteins, and peptide analogs and derivatives; peptidomimetics; antibodies and antigen binding fragments thereof; nucleic acids; nucleic acid analogs and derivatives; an extract made from biological materials such as bacteria, plants, fungi, or animal cells; animal tissues; naturally occurring or synthetic compositions; and any combinations thereof. In some embodiments, an active agent is a small molecule.

As used herein, the term "small molecule" can refer to compounds that are "natural product-like," however, the term "small molecule" is not limited to "natural product-like" compounds. Rather, a small molecule is typically characterized in that it contains several carbon-carbon bonds, and has a molecular weight of less than 5000 Daltons (5 kDa), preferably less than 3 kDa, still more preferably less than 2 kDa, and most preferably less than 1 kDa. In some cases it is preferred that a small molecule have a molecular weight equal to or less than 700 Daltons.

Exemplary active agents include, but are not limited to, those found in Harrison's Principles of Internal Medicine, $13^{th}$ Edition, Eds. T. R. Harrison et al. McGraw-Hill N.Y., NY; Physicians' Desk Reference, $50^{th}$ Edition, 1997, Oradell New Jersey, Medical Economics Co.; Pharmacological Basis of Therapeutics, $8^{th}$ Edition, Goodman and Gilman, 1990; United States Pharmacopeia, The National Formulary, USP XII NF XVII, 1990, the complete contents of all of which are incorporated herein by reference.

Active agents include the herein disclosed categories and specific examples. It is not intended that the category be limited by the specific examples. Those of ordinary skill in the art will recognize also numerous other compounds that fall within the categories and that are useful according to the present disclosure. Examples include a radiosensitizer, a steroid, a xanthine, a beta-2-agonist bronchodilator, an anti-inflammatory agent, an analgesic agent, a calcium antagonist, an angiotensin-converting enzyme inhibitors, a beta-blocker, a centrally active alpha-agonist, an alpha-1-antagonist, an anticholinergic/antispasmodic agent, a vasopressin analogue, an antiarrhythmic agent, an antiparkinsonian agent, an antiangina/antihypertensive agent, an anticoagulant agent, an antiplatelet agent, a sedative, an ansiolytic agent, a peptidic agent, a biopolymeric agent, an antineoplastic agent, a laxative, an antidiarrheal agent, an antimicrobial agent, an antifungal agent, a vaccine, a protein, or a nucleic acid. In a further aspect, an active agent can be coumarin, albumin, steroids such as betamethasone, dexamethasone, methylprednisolone, prednisolone, prednisone, triamcinolone, budesonide, hydrocortisone, and pharmaceutically acceptable hydrocortisone derivatives; xanthines such as theophylline and doxophylline; beta-2-agonist bronchodilators such as salbutamol, fenterol, clenbuterol, bambuterol, salmeterol, fenoterol; antiinflammatory agents, including antiasthmatic anti-inflammatory agents, antiarthritis antiinflammatory agents, and nonsteroidal antiinflammatory agents, examples of which include but are not limited to sulfides, mesalamine, budesonide, salazopyrin, diclofenac, pharmaceutically acceptable diclofenac salts, nimesulide, naproxene, acetaminophen, ibuprofen, ketoprofen and piroxicam; analgesic agents such as salicylates; calcium channel blockers such as nifedipine, amlodipine, and nicardipine; angiotensin-converting enzyme inhibitors such as captopril, benazepril hydrochloride, fosinopril sodium, trandolapril, ramipril, lisinopril, enalapril, quinapril hydrochloride, and moexipril hydrochloride; beta-blockers (i.e., beta adrenergic blocking agents) such as sotalol hydrochloride, timolol maleate, esmolol hydrochloride, carteolol, propanolol hydrochloride, betaxolol hydrochloride, penbutolol sulfate, metoprolol tartrate, metoprolol succinate, acebutolol hydrochloride, atenolol, pindolol, and bisoprolol fumarate; centrally active alpha-2-agonists such as clonidine; alpha-1-antagonists such as doxazosin and prazosin; anticholinergic/antispasmodic agents such as dicyclomine hydrochloride, scopolamine hydrobromide, glycopyrrolate, clidinium bromide, flavoxate, and oxybutynin; vasopressin analogues such as vasopressin and desmopressin; antiarrhythmic agents such as quinidine, lidocaine, tocainide hydrochloride, mexiletine hydrochloride, digoxin, verapamil hydrochloride, propafenone hydrochloride, flecainide acetate, procainamide hydrochloride, moricizine hydrochloride, and disopyramide phosphate; antiparkinsonian agents, such as dopamine, L-Dopa/Carbidopa, selegiline, dihydroergocryptine, pergolide, lisuride, apomorphine, and bromocryptine; antiangina agents and antihypertensive agents such as isosorbide mononitrate, isosorbide dinitrate, propranolol, atenolol and verapamil; anticoagulant and antiplatelet agents such as Coumadin, warfarin, acetylsalicylic acid, and ticlopidine; sedatives such as benzodiazapines and barbiturates; ansiolytic agents such as lorazepam, bromazepam, and diazepam; peptidic and biopolymeric agents such as calcitonin, leuprolide and other LHRH agonists, hirudin, cyclosporin, insulin, somatostatin, protirelin, interferon, desmopressin, somatotropin, thymopentin, pidotimod, erythropoietin, interleukins, melatonin, granulocyte/macrophage-CSF, and heparin; antineoplastic agents such as etoposide, etoposide phosphate, cyclophosphamide, methotrexate, 5-fluorouracil, vincristine, doxorubicin, cisplatin, hydroxyurea, leucovorin calcium, tamoxifen, flutamide, asparaginase, altretamine, mitotane, and procarbazine hydrochloride; laxatives such as senna concentrate, casanthranol, bisacodyl, and sodium picosulphate; antidiarrheal agents such as difenoxine hydrochloride, loperamide hydrochloride, furazolidone, diphenoxylate hdyrochloride, and microorganisms; vaccines such as bacterial and viral vaccines; antimicrobial agents such as penicillins, cephalosporins, and macrolides, antifungal agents such as imidazolic and triazolic derivatives; and nucleic acids such as DNA sequences encoding for biological proteins, and antisense oligonucleotides.

Anti-cancer agents include alkylating agents, platinum agents, antimetabolites, topoisomerase inhibitors, antitumor antibiotics, antimitotic agents, aromatase inhibitors, thymidylate synthase inhibitors, DNA antagonists, farnesyl-transferase inhibitors, pump inhibitors, histone acetyltransferase inhibitors, metalloproteinase inhibitors, ribonucleoside reductase inhibitors, TNF alpha agonists/antagonists, endothelinA receptor antagonists, retinoic acid receptor agonists, immuno-modulators, hormonal and anti-hormonal agents, photodynamic agents, and tyrosine kinase inhibitors.

Antibiotics include aminoglycosides (e.g., gentamicin, tobramycin, netilmicin, streptomycin, amikacin, neomycin), bacitracin, corbapenems (e.g., imipenem/cislastatin), cephalosporins, colistin, methenamine, monobactams (e.g., aztreonam), penicillins (e.g., penicillin G, penicillinV, methicillin, natcillin, oxacillin, cloxacillin, dicloxacillin, ampicillin, amoxicillin, carbenicillin, ticarcillin, piperacillin, mezlocillin, azlocillin), polymyxin B, quinolones, and vancomycin; and bacteriostatic agents such as chloramphenicol, clindanyan, macrolides (e.g., erythromycin, azithromycin, clarithromycin), lincomyan, nitrofurantoin, sulfonamides, tetracyclines (e.g., tetracycline, doxycycline, minocycline, demeclocyline), and trimethoprim. Also included are metronidazole, fluoroquinolones, and ritampin.

Enzyme inhibitors are substances which inhibit an enzymatic reaction. Examples of enzyme inhibitors include edrophonium chloride, N-methylphysostigmine, neostigmine bromide, physostigmine sulfate, tacrine, tacrine, 1-hydroxy maleate, iodotubercidin, p-bromotetramiisole, 10-(alpha-diethylaminopropionyl)-phenothiazine hydrochloride, calmidazolium chloride, hemicholinium-3,3,5-dinitrocatechol, diacylglycerol kinase inhibitor I, diacylglycerol kinase inhibitor II, 3-phenylpropargylamine, N°-monomethyl-Larginine acetate, carbidopa, 3-hydroxybenzylhydrazine, hydralazine, clorgyline, deprenyl, hydroxylamine, iproniazid phosphate, 6-MeO-tetrahydro-9H-pyrido-indole, nialamide, pargyline, quinacrine, semicarbazide, tranylcypromine, N,N-diethylaminoethyl-2,2-diphenylvalerate hydrochloride, 3-isobutyl-1-methylxanthne, papaverine, indomethacind, 2-cyclooctyl-2-hydroxyethylamine hydrochloride, 2,3-dichloro-a-methylbenzylamine (DCMB), 8,9-dichloro-2,3,4,5-tetrahydro-1H-2-benzazepine hydrochloride, p-amino glutethimide, p-aminoglutethimide tartrate, 3-iodotyrosine, alpha-methyltyrosine, acetazolamide, dichlorphenamide, 6-hydroxy-2-benzothiazolesulfonamide, and allopurinol.

Antihistamines include pyrilamine, chlorpheniramine, and tetrahydrazoline, among others.

Anti-inflammatory agents include corticosteroids, non-steroidal anti-inflammatory drugs (e.g., aspirin, phenylbutazone, indomethacin, sulindac, tolmetin, ibuprofen, piroxicam, and fenamates), acetaminophen, phenacetin, gold salts, chloroquine, D-Penicillamine, methotrexate colchicine, allopurinol, probenecid, and sulfinpyrazone.

Muscle relaxants include mephenesin, methocarbomal, cyclobenzaprine hydrochloride, trihexylphenidyl hydrochloride, levodopa/carbidopa, and biperiden.

Anti-spasmodics include atropine, scopolamine, oxyphenonium, and papaverine.

Analgesics include aspirin, phenylbutazone, idomethacin, sulindac, tolmetic, ibuprofen, piroxicam, fenamates, acetaminophen, phenacetin, morphine sulfate, codeine sulfate, meperidine, nalorphine, opioids (e.g., codeine sulfate, fentanyl citrate, hydrocodone bitartrate, loperamide, morphine sulfate, noscapine, norcodeine, normorphine, thebaine, norbinaltorphimine, buprenorphine, chlomaltrexamine, funaltrexamione, nalbuphine, nalorphine, naloxone, naloxonazine, naltrexone, and naltrindole), procaine, lidocain, tetracaine and dibucaine.

Ophthalmic agents include sodium fluorescein, rose bengal, methacholine, adrenaline, cocaine, atropine, alpha-chymotrypsin, hyaluronidase, betaxalol, pilocarpine, timolol, timolol salts, and combinations thereof.

Prostaglandins are art recognized and are a class of naturally occurring chemically related long-chain hydroxy fatty acids that have a variety of biological effects.

Anti-depressants are substances capable of preventing or relieving depression. Examples of anti-depressants include imipramine, amitriptyline, nortriptyline, protriptyline, desipramine, amoxapine, doxepin, maprotiline, tranylcypromine, phenelzine, and isocarboxazide.

Trophic factors are factors whose continued presence improves the viability or longevity of a cell. trophic factors include, without limitation, platelet-derived growth factor (PDGP), neutrophil-activating protein, monocyte chemoattractant protein, macrophage-inflammatory protein, platelet factor, platelet basic protein, and melanoma growth stimulating activity; epidermal growth factor, transforming growth factor (alpha), fibroblast growth factor, platelet-derived endothelial cell growth factor, insulin-like growth factor, glial derived growth neurotrophic factor, ciliary neurotrophic factor, nerve growth factor, bone growth/cartilage-inducing factor (alpha and beta), bone morphogenetic proteins, interleukins (e.g., interleukin inhibitors or interleukin receptors, including interleukin 1 through interleukin 10), interferons (e.g., interferon alpha, beta and gamma), hematopoietic factors, including erythropoietin, granulocyte colony stimulating factor, macrophage colony stimulating factor and granulocyte-macrophage colony stimulating factor; tumor necrosis factors, and transforming growth factors (beta), including beta-1, beta-2, beta-3, inhibin, and activin.

Hormones include estrogens (e.g., estradiol, estrone, estriol, diethylstibestrol, quinestrol, chlorotrianisene, ethinyl estradiol, mestranol), anti-estrogens (e.g., clomiphene, tamoxifen), progestins (e.g., medroxyprogesterone, norethindrone, hydroxyprogesterone, norgestrel), antiprogestin (mifepristone), androgens (e.g, testosterone cypionate, fluoxymesterone, danazol, testolactone), anti-androgens (e.g., cyproterone acetate, flutamide), thyroid hormones (e.g., triiodothyronne, thyroxine, propylthiouracil, methimazole, and iodixode), and pituitary hormones (e.g., corticotropin, sumutotropin, oxytocin, and vasopressin). Hormones are commonly employed in hormone replacement therapy and/or for purposes of birth control. Steroid hormones, such as prednisone, are also used as immunosuppressants and anti-inflammatories.

In some embodiments, the active agent is an agent that stimulates tissue formation, and/or healing and regrowth of natural tissues, and any combinations thereof. Agents that increase formation of new tissues and/or stimulates healing or regrowth of native tissue at the site of injection can include, but are not limited to, fibroblast growth factor (FGF), transforming growth factor-beta (TGF-β, platelet-derived growth factor (PDGF), epidermal growth factors (EGFs), connective tissue activated peptides (CTAPs), osteogenic factors including bone morphogenic proteins, heparin, angiotensin II (A-II) and fragments thereof, insulin-like growth factors, tumor necrosis factors, interleukins, colony stimulating factors, erythropoietin, nerve growth factors, interferons, biologically active analogs, fragments, and derivatives of such growth factors, and any combinations thereof.

In some embodiments, the active agent may be a wound healing agent. As used herein, a "wound healing agent" is a compound or composition that actively promotes wound healing process. Exemplary wound healing agents include, but are not limited to dexpanthenol; growth factors; enzymes, hormones; povidon-iodide; fatty acids; anti-inflammatory agents; antibiotics; antimicrobials; antiseptics; cytokines; thrombin; angalgesics; opioids; aminoxyls; furoxans; nitrosothiols; nitrates and anthocyanins; nucleosides, such as adenosine; and nucleotides, such as adenosine diphosphate (ADP) and adenosine triphosphate (ATP); neutotransmitter/neuromodulators, such as acetylcholine and 5-hydroxytryptamine (serotonin/5-HT); histamine and catecholamines, such as adrenalin and noradrenalin; lipid molecules, such as sphingosine-1-phosphate and lysophosphatidic acid; amino acids, such as arginine and lysine; peptides such as the bradykinins, substance P and calcium gene-related peptide (CGRP); nitric oxide; and any combinations thereof.

In certain embodiments, the active agents described herein are immunogens. In one embodiment, the immunogen is a vaccine. Most vaccines are sensitive to environmental conditions under which they are stored and/or transported. For example, freezing may increase reactogenicity (e.g., capability of causing an immunological reaction) and/or loss of potency for some vaccines (e.g., HepB, and DTaP/IPV/HIB), or cause hairline cracks in the container, leading to contamination. Further, some vaccines (e.g., BCG, Varicella, and MMR) are sensitive to heat. Many vaccines (e.g., BCG, MMR, Varicella, Meningococcal C Conjugate, and most DTaP-containing vaccines) are light-sensitive. See, e.g., Galazka et al., *Thermostability of vaccines*, in Global Programme for Vaccines & Immunization (World Health Organization, Geneva, 1998); Peetermans et al., *Stability of freeze-dried rubella virus vaccine (Cendehill strain) at various temperatures,* 1 J. Biological Standardization 179 (1973). Thus, the compositions and methods described herein also provide for stabilization of vaccines regardless of the cold chain and/or other environmental conditions.

In some embodiments, the active agent is a cell, e.g., a biological cell. Cells useful for incorporation into the composition can come from any source, e.g., mammalian, insect, plant, etc. In some embodiments, the cell can be a human, rat or mouse cell. In general, cells to be used with the compositions described herein can be any types of cells. In general, the cells should be viable when encapsulated within compositions. In some embodiments, cells that can be used with the composition include, but are not limited to, mammalian cells (e.g. human cells, primate cells, mammalian cells, rodent cells, etc.), avian cells, fish cells, insect cells, plant cells, fungal cells, bacterial cells, and hybrid cells. In some embodiments, exemplary cells that can be can be used with the compositions include platelets, activated platelets, stem cells, totipotent cells, pluripotent cells, and/or embryonic stem cells. In some embodiments, exemplary cells that can be encapsulated within compositions include, but are not limited to, primary cells and/or cell lines from any tissue. For example, cardiomyocytes, myocytes, hepatocytes, keratinocytes, melanocytes, neurons, astrocytes, embryonic stem cells, adult stem cells, hematopoietic stem cells, hematopoietic cells (e.g. monocytes, neutrophils, macrophages, etc.), ameloblasts, fibroblasts, chondrocytes, osteoblasts, osteoclasts, neurons, sperm cells, egg cells, liver cells, epithelial cells from lung, epithelial cells from gut, epithelial cells from intestine, liver, epithelial cells from skin, etc, and/or hybrids thereof, can be included in the silk/platelet compositions disclosed herein. Those skilled in the art will recognize that the cells listed herein represent an exemplary, not comprehensive, list of cells. Cells can be obtained from donors (allogenic) or from recipients (autologous). Cells can be obtained, as a non-limiting example, by biopsy or other surgical means known to those skilled in the art.

In some embodiments, the cell can be a genetically modified cell (e.g., a chimeric antigen receptor-expressing cell). A cell can be genetically modified to express and secrete a desired compound, e.g. a bioactive agent, a growth factor, differentiation factor, cytokines, and the like. Methods of genetically modifying cells for expressing and secreting compounds of interest are known in the art and easily adaptable by one of skill in the art. Differentiated cells that have been reprogrammed into stem cells can also be used. For example, human skin cells reprogrammed into embryonic stem cells by the transduction of Oct3/4, Sox2, c-Myc and Klf4 (Junying Yu, et. al., *Science,* 2007, 318, 1917-1920 and Takahashi K. et. al., *Cell,* 2007, 131, 1-12).

Additionally, provided compositions may be used to deliver any type of molecular compound, such as, pharmacological materials, vitamins, sedatives, steroids, hypnotics, antibiotics, chemotherapeutic agents, prostaglandins, and radiopharmaceuticals. In some embodiments, provided compositions are suitable for delivery of the above materials and others including but not limited to proteins, peptides, nucleotides, carbohydrates, simple sugars, cells, genes, anti-thrombotics, anti-metabolics, growth factor inhibitor, growth promoters, anticoagulants, antimitotics, fibrinolytics, anti-inflammatory steroids, and monoclonal antibodies.

In some embodiments, active agents may be integrated into provided compositions in any application-appropriate way. For example, in some embodiments, an active agent may be embedded in one or more layers of a provided composition. In some embodiments, an active agent may be encapsulated or substantially encapsulated by one or more layers of a provided composition. In some embodiments, an active agent may be applied to a provided composition, for example, as a coating or component thereof. In some embodiments, an active agent may be adsorbed onto one or more layers of a provided composition.

In accordance with certain embodiments, a provided composition may comprise more than one active agent. In some embodiments, provided compositions may comprise two or more (e.g., 3, 4, 5, 6, 7, 8, 9, 10, or more) active agents. In some embodiments, each pliable layer comprises the same active agent(s). In some embodiments, at least two pliable layers comprise different active agent(s), including none in one pliable layer. In some embodiments, each pliable layer comprises substantially the same amount of an active agent. In some embodiments, at least two pliable layers comprise different concentrations of active agent(s), including none in one pliable layer.). In some embodiments, at least two rigid layers comprise different active agent(s), including none in one rigid layer. In some embodiments, each rigid layer comprises substantially the same amount of an active agent. In some embodiments, at least two rigid layers comprise different concentrations of active agent(s), including none in one rigid layer.

The amount of active agent in a particular layer or composition may vary from pictograms to milligrams. In some embodiments, provided compositions may include at least 1 ug/mg (e.g., 2, 3, 4, 5, 6, 7, 8, 9, 10 or more ug/mg) of at least one active agent.

Computational Model

The technologies described herein may include one or more computational models for material assembly or deposition. A method for designing a biomimetic multilayer membrane may include a computational model of, e.g., a membrane layer or membrane material. Coarse-grained models of protein nanofibrils (NFs) and calcium-based minerals nanoplates (NPs) were developed, for example in order to identify the conditions where these two components can form porous multilayer structures. Each NF and NP can be modelled by an elastic network with carefully chosen elastic constants to reflect the elastic properties of the materials and mass concentrated at junction beads to reflect the material densities.

Numerical values of the physical parameters of the NF and AP can be obtained from atomistic simulations, while the features including chemical concentrations and particle geometries can obtained from experimental measurements, for example using Scanning Electron Microscopy (SEM). After computational simulation, a simulation result of the multilayer material may be formed in silico and can be compared to experimental observation in SEM Example Elastic network models can be built on mechanics and geometry features of the unit building blocks. The following provides an exemplary, non-limiting, method for designing particular embodiments. For example, each SNF flake and HAP thread may be modeled by an elastic network with carefully chosen elastic constants to match the materials' elastic properties and mass concentrated at the junction beads to match the material densities. FIG. 1 shows a schematic figure of the coarse-grained computational model for HAP and SNF. A SNF fiber can be modeled by a series of mass beads connected by a series of harmonic springs, and a HAP flake can be modeled by mass beads connected by a rectangular spring network (FIG. 1). For SNF the total energy function is given by $$E = E_T + E_B + E_{non-bond} \quad (5)$$

Where $E_T$ is the tensile deformation energy for fiber stretching, $E_B$ for bending and $E_{non-bond}$ for non-bonded interaction with other SNF beads and HAP beads. Each energy term is defined by $$E_T = \Sigma \varphi_T(r), \; \varphi_T(r) = k(r-r_0)^2 \quad (6)$$

$$k = E_{SNF} A/(2r_0) = E_{SNF} \pi d^2/(8r_0) \quad (7)$$

Where d is the silk fiber diameter, $r_0$ is the equilibrium distance between two neighbouring beads, $E_{SNF}=1.5$ GPa is the average secant modulus of silkworm silk under tensile loading. The bending energy was given by $$E_B = \Sigma \varphi_B(\theta), \; \varphi_B(\theta) = K_B(\theta - \theta_0)^2 \quad (8)$$

$$K_B = \frac{E_{SNF} I_t}{2r_0} = \frac{E_{SNR} \pi d^4}{128 r_0} \quad (9)$$

The mass of the bead is given by $$m_{SNF} = \pi d^2 r_0 \rho/4 \quad (10)$$

where $\rho=1300$ kg/m$^3$ is the density of silk fiber.

For HAP, each bond stiffness is given by $$k = E_{HAP} t^2/(2t) = E_{HAP} t/2 \quad (11)$$

Where $E_{HAP}=114$ GPa is Young's modulus of HAP and t=6 nm is the average thickness of HAP flakes. For angular spring that connect two neighboring bond with 180° angle, its stiffness is defined by the bending stiffness of the HAP flake $$K_{B1} = \frac{E_{HAP} I_t}{2r_0} = \frac{E_{HAP} t^3}{24} \quad (12)$$

For angular spring that connect two neighboring bond with 90° angle, its stiffness is defined by the shear stiffness of the HAP flake $$K_{B2} = \frac{1}{8} G_{HAP} t^3 \quad (13)$$

The mass of HAP bead was given by $$m = t^3 \rho \quad (14)$$

Where $\rho=3\times10^3$ kg/m$^3$ is the density of HAP. For interfacial interactions between two molecules $$E_{non-bound} = \Sigma \varphi_{non-bound}(r), \quad (15)$$

$$\varphi_{non-bound}(r) = 4\epsilon\left[\left(\frac{\sigma}{r}\right)^{12} - \left(\frac{\sigma}{r}\right)^6\right] \quad (16)$$

For interaction between a pair of non-bonded SNF-SNF beads $E_{SNF-SNF}=\gamma_{NF-SNF} dr_0$, $\gamma=0.217$ J/m$^2$ (protein adhesion energy), from literature (C. Deng et al., Ultrathin self-assembled anionic polymer membranes for superfast size-selective separation. Nanoscale 5, 11028-11034 (2013)).), $\sigma=2^{-1/6}d$ For interaction between a pair of non-bonded HAP-HAP beads $E_{HAP-HAP}=\gamma t^2$, $\gamma=1.180$ (Cleavage energy)−0.3653 (Water immersion energy)=0.8147 J/m², from literature (6), $\sigma=2^{-1/6}t$ For interaction between a pair of non-bonded SNF-HAP beads $E=\gamma_{HAP-SNF} dr_0$, $\sigma=2^{-1/6}d$ HAP-SNF surface energy $\gamma_{HAP-SNF}$ may not be readily ascertainable as it depends on the molecular structure and the hierarchy structure of the interface in contact. The effect of its numerical value may affect forming of the layered structure.

Figure 2:
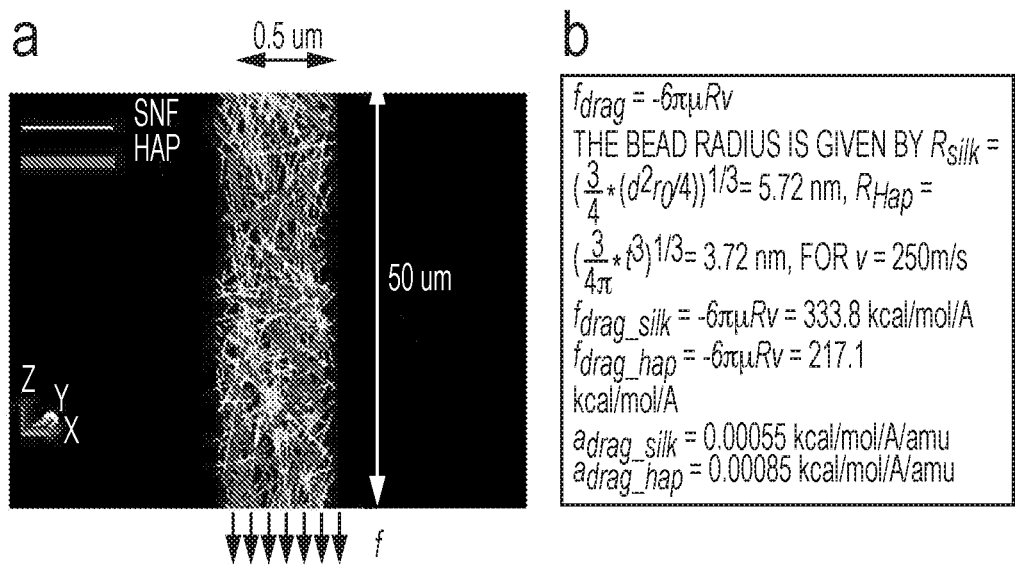
FIG. 2, panel a, shows simulation setups for example SNF/HAP assembly and deposition modeling. Panel b shows exemplary parameters for SNF/HAP assembly and deposition modeling.

The initial geometry of the example simulation box may be generated in Matlab script. For example, the box size may be 0.5×0.5×50 µm³ with 50 µm along the axis of the flow direction and periodic boundary conditions may be applied to the other two directions. A collection of SNFs are generated to have a length distribution with mean value of 1 µm and standard deviation of 0.4 µm. HAPs are generated to have a uniform size as 6×30×240 nm³. The ratio of numbers of SNF and HAP molecules are computed according to their volume ratio in solution as applicable in experiments. The volume ratio of both HAP and SNF are increased by 16 times to account for the effect of getting concentrated at the bottom of bottle and overcame the limitation of size and time of simulations. FIG. 2 shows simulation setups (FIG. 2, panel a) and related parameters (FIG. 2, panel b) for example SNF/HAP assembly and deposition modeling. Each SNF and HAP is initially randomly placed and oriented in the simulation box as shown in FIG. 2, panel a. A substrate modeled by LJ9-3 potential at the bottom of the simulation box (z=0) is used to simulate the substrate that supports the SNF-HAP deposition. The initial geometry of an example simulation box is shown in FIG. 2, panel a.

Fluid (e.g., water) flow may be modeled implicitly, for example, by applying the drag force on all the coarse-grained beads. The simulation setups and related parameters are summarized in FIG. 2, panel b. HAP and SNF beads are subjected to a gravity field that accounts for the drag force from the water flow. The drag force is given by Stokes' law as $$f_{drag} = -6\pi\mu R v \qquad (17)$$

Where the effective bead radius is given by $$R_{silk} = \left(\frac{3}{4}*(d^2 r_0/4)\right)^{1/3} = 5.72 \text{ nm},$$

$$R_{Hap} = \left(\frac{3}{4\pi}*t^3\right)^{1/3} = 3.72 \text{ nm},$$

$\mu=8.6\times10^{-4}$ Pa·s is the fluid viscosity constant of water at room temperature and v=250 m/s is the flow velocity used in example simulations. Its large numerical value is used to overcome the limitation of simulation time scale. The numerical values of the physical parameters of the example model are summarized in Table 1.

TABLE 1

| Parameter and units | Numerical value for SNF | Numerical value for HAP |
|---|---|---|
| Equilibrium bead distance $r_0$, t (in nm) | 10 | 6 |
| Molecule geometry in other dimensions d (in nm) | 10 | 30 × 240 |

TABLE 1-continued

| Parameter and units | Numerical value for SNF | Numerical value for HAP |
|---|---|---|
| Tensile stiffness parameters k (in kcal/mol/A²) | 8.50 | 492 |
| Equilibrium angle $\theta_0$ (in rad) | π | π, π/2 |
| Bending stiffness parameter $K_B$ (in kcal/mol) | 5300 | 1.5 × 10⁵, 1.73 × 10⁵ |
| SNF-SNF bead non-bonded interaction energy (in kcal/mol) | 3125 | |
| SNF-SNF bead non-bonded interaction equilibrium distance (in nm) | 8.9 | |
| HAP-HAP bead non-bonded interaction energy (in kcal/mol) | | 4223 |
| HAP-HAP bead non-bonded interaction equilibrium distance (in nm) | | 5.3 |
| SNF-HAP bead non-bonded interaction energy (in kcal/mol) | $\gamma_{HAP-SNF} dr_0$ | |
| SNF-HAP bead non-bonded interaction equilibrium distance (in nm) | 8.9 | |
| Mass of each mesoscale particle m (in amu) | 614650 | 390100 |
| Drag force factor $\frac{f_{drag}}{m}$ (in kcal/mol/A/amu) | 0.00055 | 0.00085 |

Figure 3:
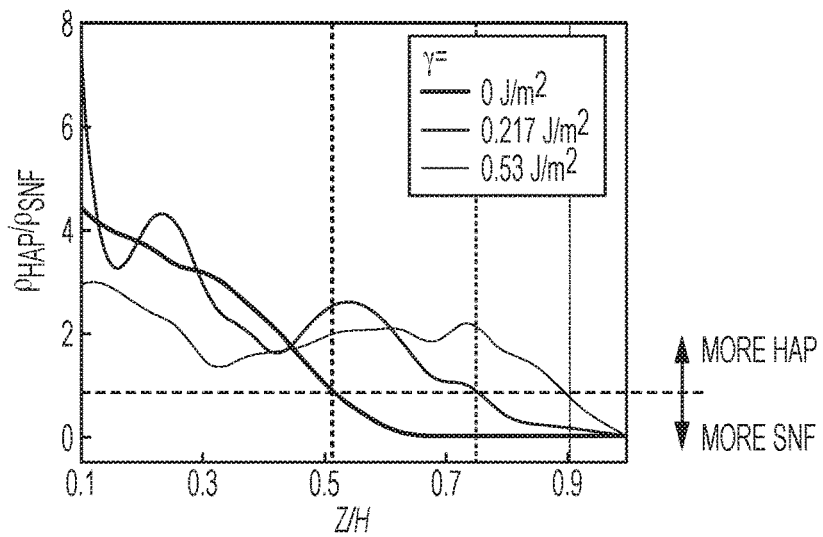
FIG. 3 shows exemplary distributions of the mass ratio between HAP and SNF as functions of the coordinate along the membrane thickness direction for 3 membranes.

The numerical value of $\gamma_{HAP-SNF}$ was varied from 0 to 0.53 J/m² in the example simulations, This interfacial energy may highly affect the geometry of the multilayer membrane as it deposited on the substrate. FIG. 3 shows distributions of the mass ratio between HAP and SNF as functions of the coordinate along the membrane thickness direction for the 3 membranes assembled with different $\gamma_{HAP-SNF}$ values. The dash line suggests the transition from more HAP to more SNF region, for which the stronger HAP/SNF interaction may lead to a more homogenously mixed material. For a weak HAP/SNF interaction, the transition from more HAP to more SNF region may take place closer to the middle of the membrane. For a strong HAP/SNF interaction, the transition from more HAP to more SNF region may take place closer to the top surface, as the two materials are more homogeneous mixed before forming the membrane.

Various simulations can be run to account for the variation of the stiffness and density for the broad range of protein nanofibers (NFs) and calcium based minerals nano plates (NPs). An example range of mineral densities (from 1×10³ to 3×10³ kg/m³) and stiffnesses of NFs (from 0.3 to 15 GPa) and NPs (from 114 to 570 GPa) may be found for the physical properties of these models (Table 2).

TABLE 2

| Model # | $E_{NF}$ (GPa) | $E_{NP}$ (GPa) | $\rho_{NF}$ (kg/m³) | $\rho_{NP}$ (kg/m³) |
|---|---|---|---|---|
| 1 | 0.75 | 114 | 1300 | 3000 |
| 2 | 1.5 | 570 | 1300 | 3000 |
| 3 | 0.3 | 114 | 1300 | 3000 |
| 4 | 15 | 114 | 1300 | 3000 |
| 5 | 1.5 | 114 | 1300 | 1000 |

Figure 4:
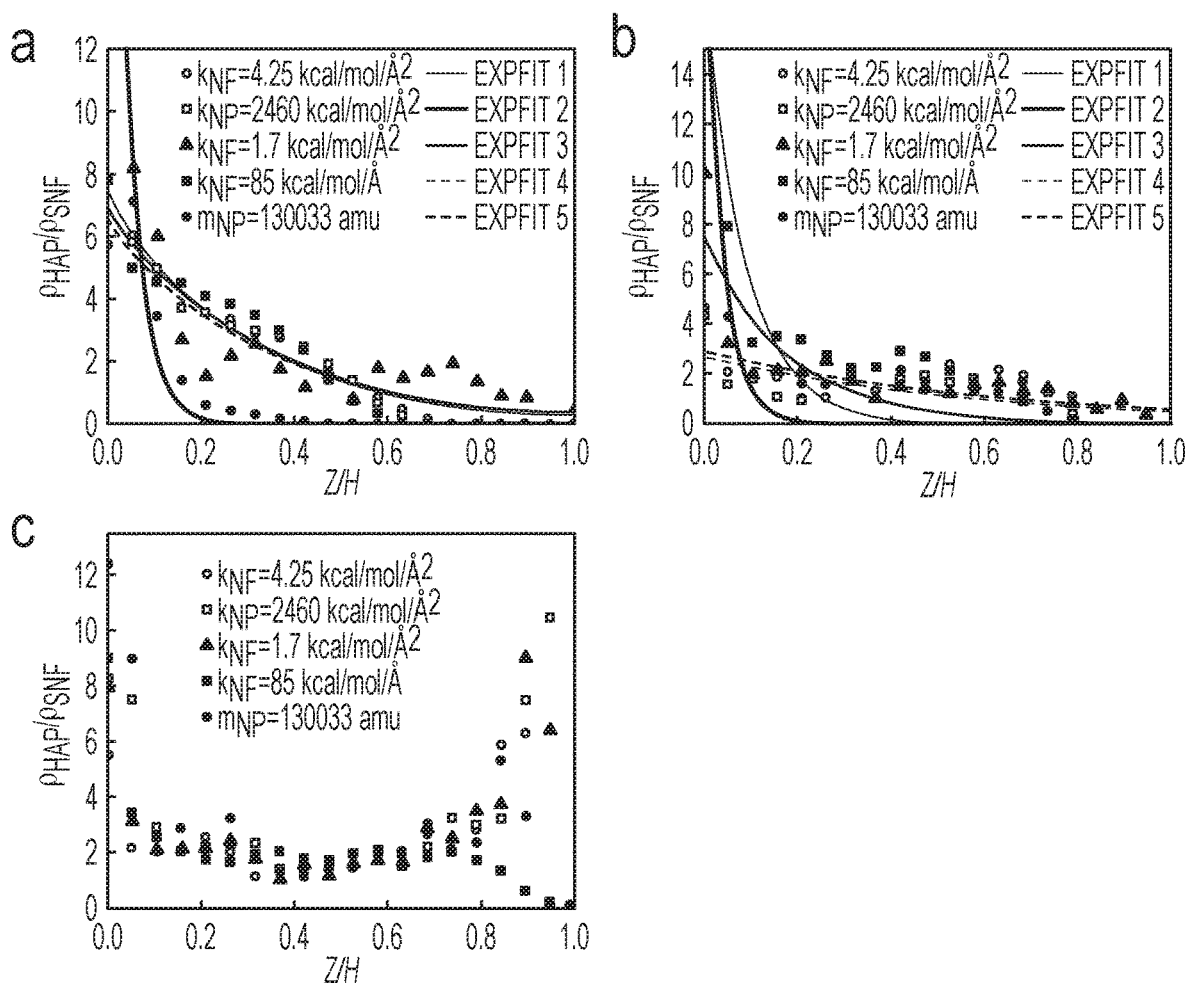
FIG. 4, panel a, shows a graph illustrating distributions of mass ratio between NP and NF as functions of the coordinate along the membrane thickness direction for 15 membranes assembled with $\gamma_{HAP-SNF}$=0 J/m$^2$. Panel b shows a graph illustrating distributions of mass ratio between NP and NF as functions of the coordinate along the membrane thickness direction for 15 membranes assembled with $\gamma_{HAP-SNF}$=0.217 J/m$^2$. Panel c shows a graph illustrating distributions of mass ratio between NP and NF as functions of the coordinate along the membrane thickness direction for 15 membranes assembled with $\gamma_{HAP-SNF}$=0.53 J/m$^2$.

The membrane deposition process is repeated for these 5 different models by applying $\gamma_{HAP-SNF}$=0, 0.217 and 0.53 J/m² (15 individual extra simulations). FIG. 4 shows graphs illustrating distributions of mass ratio between NP and NF as functions of the coordinate along the membrane thickness direction for 15 membranes assembled with different $\gamma_{HAP-SNF}$ values ($\gamma_{HAP-SNF}$=0, 0.217 and 0.53 J/m² for FIG. 4, panels a, b, and c, respectively). The exponential fitted curves in FIG. 4, panel a and FIG. 4, panel b suggest that the mass ratio decays from a high value to 0 as away from the substrate, agreeing with the simulation results of a multilayer structures. The value of $\gamma_{HAP-SNF}$ may play a predominant role to govern the membrane assembly, as $\gamma_{HAP\text{-}SNF}$<0.217 can lead to a multilayer structure as the mass ratio between HP and NF exponentially decays from a high value to 0 as away from the substrate. However, for high $\gamma_{HAP\text{-}SNF}$, NPs and NFs are well mixed to form a more homogeneous hybrid membrane material.

Figure 5:
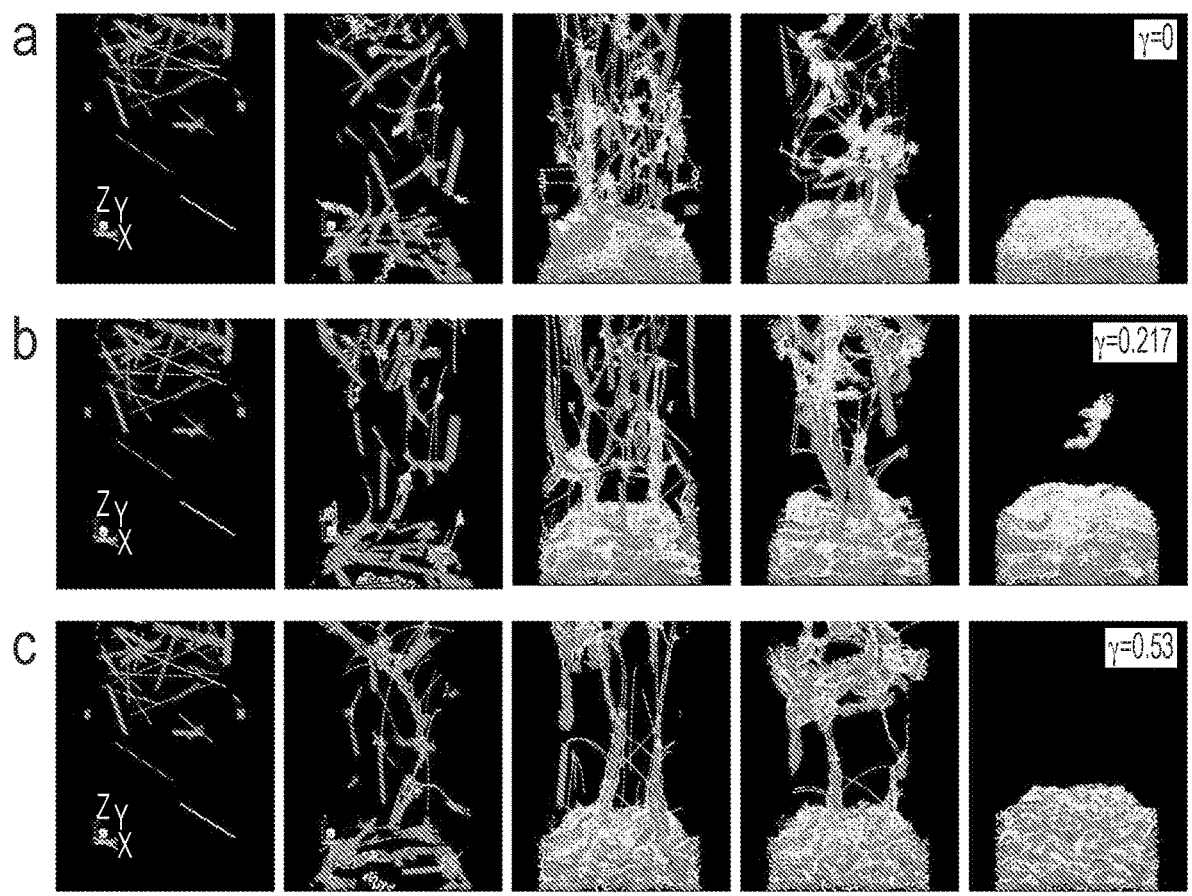
FIG. 5, row a, shows a coarse-grained computational MD simulation result for SNF/HAP assembly and deposition with γ set as 0 J/m$^2$. Row b shows a coarse-grained computational MD simulation result for SNF/HAP assembly and deposition with γ set as 0.217 J/m$^2$. Row c shows a coarse-grained computational MD simulation result for SNF/HAP assembly and deposition with γ set as 0.53 J/m$^2$.

Using the collection of these models, molecular dynamics (MD) simulations can be run to simulate their assembly during the deposition process in fluid (e.g., water) flow. By way of specific example, FIG. 5 shows coarse-grained computational MD simulations for SNF/HAP assembly and deposition. HAP-SNF surface energy $\gamma$ (J/m$^2$) depends on the molecular structure and the hierarchy structure of the interface in contact. This may be important for forming a layered structure. In an example SNF/HAP model, HAP and SNF particles are randomly distributed initially and then subjected to a gravity field that accounts for the drag force from the water flow. FIG. 5 shows a comparison of an example assembly process of NFs and NPs, with snapshots of an HAP/SNF assembly process during deposition with $\gamma$ set as 0 (FIG. 5, panel a), 0.217 (FIG. 5, panel b) and 0.53 J/m$^2$ (FIG. 5, panel c), respectively. By tuning the material stiffness, density and interfacial interactions between the subunits, the NFs and NPs can either assemble to form a multilayer structure with a clear boundary between two material phases or a homogeneous mixture of the two materials. Without wishing to be bound by theory, for a wide range of mineral density (as the material density of protein is almost fixed) and stiffness of NFs and NPs, the interfacial energy ($\gamma$) between NF and NP can play a dominating role to govern the assembly. Computational simulations for weak NF/NP interaction indicate that NFs are assembled into a continuous network during the deposition process and their deposition rates are smaller than those of NP flakes that lack such a self-assembly process. In strong NF/NP interactions, NF and NP flakes appear well mixed by self-assembly before being deposited on the substrate. Accordingly, a NF/NP interaction weaker than both NF/NF interaction and NP/NP interaction (e.g., $\gamma$<0.217 J/m$^2$, the average surface energy measured for protein filament assembly) may be necessary to form layered structures.). Suitable combinations of materials to form multilayer structures may be determined using the method described herein. Many protein/mineral combinations have strong interfacial interactions and may not suitable for use as raw materials for forming these multilayer structures. In one example implementation, on the basis of the simulations, different material combinations may be evaluated. In some specific implementations, silk nanofibrils (SNFs) and hydroxyapatite (HAP) may selected as base materials for manufacturing a multilayer nanoporous membrane.

Membrane Production

Figure 6:
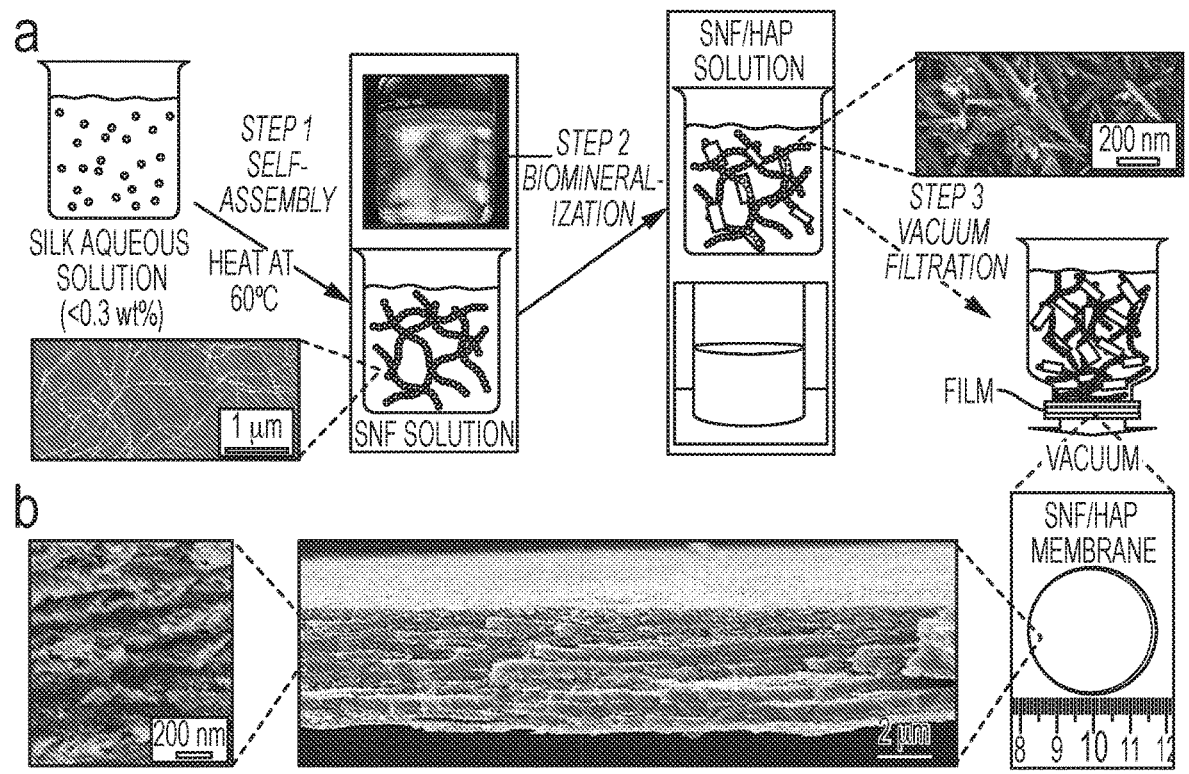
FIG. 6, panel a, shows a schematic of a preparation process of SNF/HAP membranes. Panel b shows SEM images of multilayer structures of example membranes.

The technologies described herein may include one or more methods of manufacturing suitable protein and/or mineral materials/layers (e.g., pliable or rigid layers). In one example implementation, on the basis of the simulations, different material combinations may be evaluated. In some specific implementations, silk nanofibrils (SNFs) and hydroxyapatite (HAP) can be used as a starting materials. An example process to produce SNFs, controlling the self-assembly of silk protein is shown in FIG. 6. FIG. 6, panel a shows a schematic of a preparation process of SNF/HAP membranes. Silk is assembled to SNFs in aqueous solution. The bottom picture in the first row is an atomic force microscopy (AFM) image of SNFs; the top picture in the second row is the SNF solution under polarized light, indicating the presence of a nematic phase of SNFs. Subsequently, SNFs are used as templates to induce the growth of HAP nanocrystals. The bottom picture in the third row is a photograph of SNF/HAP solution; the top picture in the fourth row is an scanning electron microscopy (SEM) image of biomineralized HAP nanocrystals. Subsequently, SNF/HAP dispersions are assembled into membranes via vacuum filtration. FIG. 6, panel b shows SEM images of multilayer structures of example membranes. The first picture is the high resolution cross-section SEM of a SNF/HAP membrane. The clear SNF and HAP rich layer can be observed. The second picture is the cross-sectional SEM image of SNF/HAP membrane, which shows nacre-like highly ordered multilayer structures. The third picture is a SNF/HAP membrane with thickness of 4 μm. A membrane can be directly moved from the supporting substrate after filtration of the SNF/HAP dispersion in a process that may take about 9 s. False color is used in AFM and SEM images.

Figure 7:
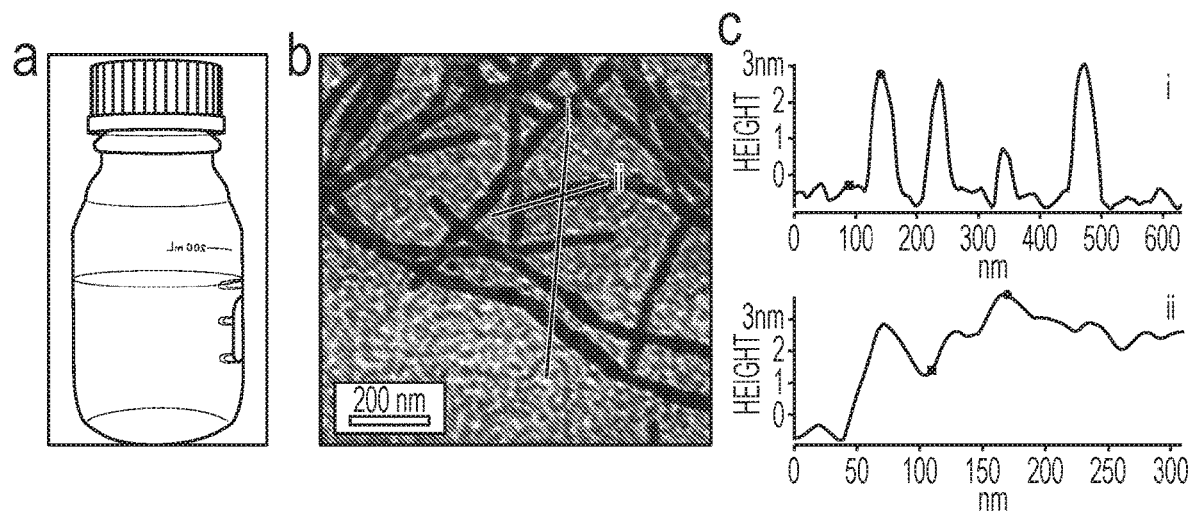
FIG. 7, panel a, shows a photograph of silk nanofibril (SNF) solution (~0.1 wt %). Panel b shows an AFM phase image of sample SNFs. Panel c shows graphs illustrating height profiles collected along the indicated colored lines.

In an example process, aqueous silk fibroin (~0.1 wt %) solution is assembled into elongated SNFs at 60° C. and incubated for 1 week without requirements of other processes. FIG. 7, panel a shows a photograph of silk nanofibril (SNF) solution (~0.1 wt %). The resulting solution is transparent, with strong birefringent under polarized light (FIG. 7, panel a), indicating the presence of a nematic phase of SNFs. The structural features of the SNFs can be determined by atomic force microscopy (AFM). FIG. 7, panel b shows an AFM phase image of sample SNFs. FIG. 7, panel c shows graphs illustrating height profiles collected along the indicated colored lines. Careful examination of the image b and height profile (ii) reveals that the SF nanofibrils have a necklace-like morphology. In an example, the SNFs exhibited a necklace-like morphology, with a height of 3-4 nm and a contour length up to 5 μm (FIG. 7, panels b and c). The center-to-center distance of the beads is about 25 nm.

In some implementations, SNFs can be used as templates to grow HAP nanocrystals with needle-like structure through in situ biomineralization. Example HAP nanocrystals, with a length of 100-300 nm and a width of 20-30 nm, may show a uniform needle-like morphology and can be stabilized by connected SNF networks, thus such HAP nanocrystals may be finely dispersed and highly stable in the SNF solution (FIG. 7, panel a).

Figure 8:
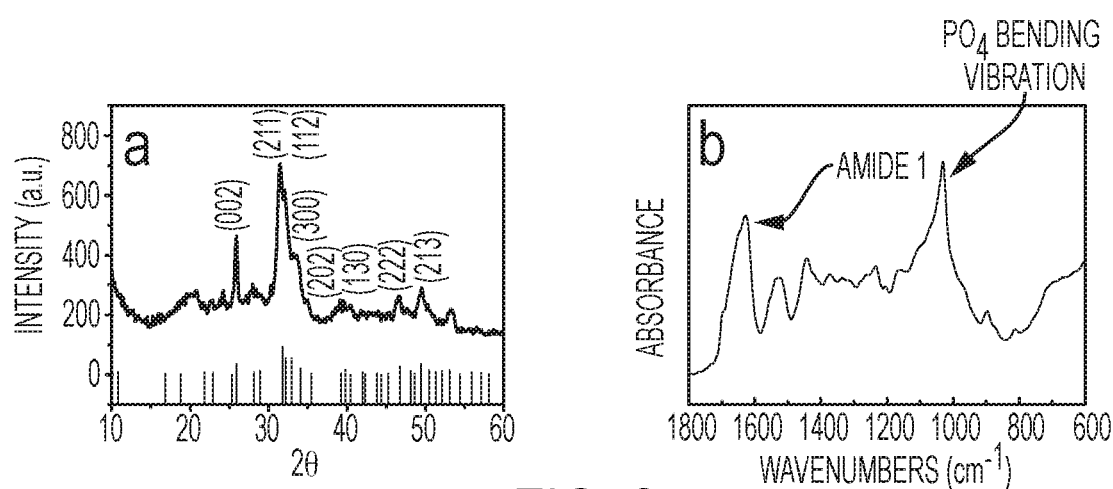
FIG. 8, panel a, shows a graph illustrating an XRD profile of a biomineralized hydroxylapatite (HAP) nanocrystal. Panel b shows a graph illustrating an FTIR spectrum of a SNF/HAP (60/40) membrane.

In an example, biomineralization is carried out in 0.1 wt % aqueous SNF solution. The biomineralized HAP can be confirmed by X-ray diffraction (XRD) and Fourier transform infrared spectroscopy (FTIR) characterization. FIG. 8, panel a shows a graph illustrating an XRD profile of a biomineralized hydroxylapatite (HAP) nanocrystal. The expected standard diffraction peaks according to the Joint Committee on Powder Diffraction Standards (JCPDS) for HAP are shown as discrete bars (JCPDS No. 09-0432). FIG. 8, panel b shows a graph illustrating an FTIR spectrum of a SNF/HAP (60/40) membrane. The XRD profile of biomineralized HAP shows the same peaks as the standard diffraction peaks of a HAP crystal (FIG. 8, panel a). In FTIR spectra (FIG. 8, panel b), two bands in the 1700-1500 cm$^{-1}$ range are amide I and amide II of SNFs. The secondary structures of SNF can be determined via assessment of the amide I bands (1700-1600 cm$^{-1}$). The spectra in the amide I bands show a similar shape to that of degummed silk fibers; a sharp peak at 1620 m$^{-1}$ and a shoulder at 1695 cm$^{-1}$, which were assigned to β-sheets and β-turns of the hairpin-folded antiparallel β-sheet structure, respectively. These results may indicate that example SNFs are mainly composed of β-sheet. The 1200-900 cm$^{-1}$ region with the peak at 1037 cm$^{-1}$ is observed due to PO$_4$ bending vibration of HAP crystal.

Figure 9:
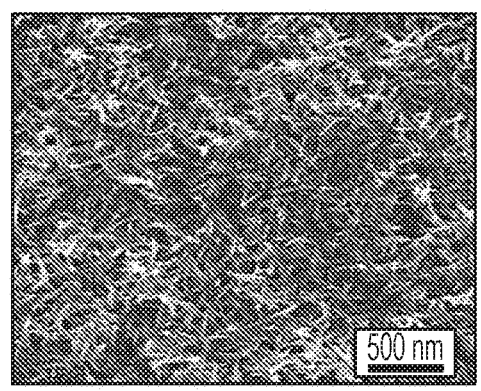
FIG. 9 shows a sample SEM image of a biomineralized HAP nanocrystal.
Figure 10:
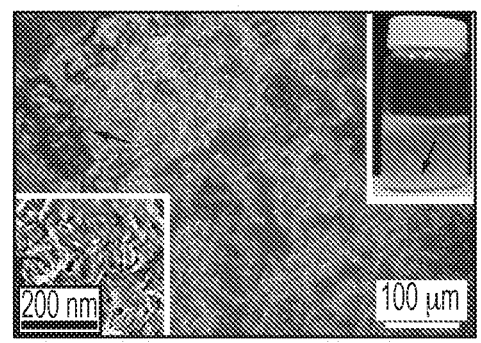
FIG. 10 shows images of bio-mineralized HAP.

The morphology of SNF-biomineralized HAP is determined by scanning electron microscopy (SEM). FIG. 9 shows a sample SEM image of a biomineralized HAP nanocrystal. All example HAP nanocrystals have similar shape and size and no aggregates can be observed (FIG. 9). This may be in contrast to the flower-like HAP aggregates in silk solution from control experiments. FIG. 10 shows images of bio-mineralized HAP. In this example, silk fibroin solution (0.1 wt %) induced the growth of HAP at 37° C. for 1 week. The largest (central) image is the optical microscopy image of bio-mineralized HAP. The white arrow indicates large aggregates of HAP crystals. The left bottom picture is an SEM image of HAP flower-like aggregates. The right top image is a photograph of silk fibroin solution after biomineralization of HAP. The white arrow shows that the HAP aggregates were precipitated to the bottom of the bottle.

Figure 11:
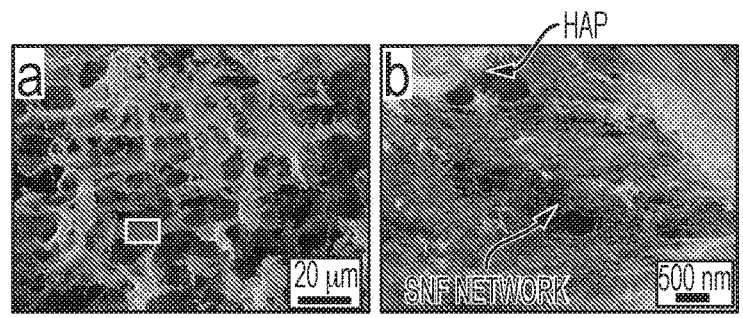

Example SNF/HAP solution can be frozen with liquid nitrogen, followed by freeze drying. FIG. 11 show a mesostructure of SNF/HAP solution after liquid nitrogen freezing and freeze drying. FIG. 11, panel b shows a partial enlarged image of the image in FIG. 11, panel a. The SEM images of the resulting powders reveal that SNFs can form uniformly connected networks (FIG. 11, panel a) and that the synthetic HAP nanocrystals can be held and stabilized by porous SNF networks (FIG. 11, panel b).

The Example SNF/HAP dispersion can be assembled into water insoluble macroscopic membranes, e.g., via vacuum filtration. The thickness of the membranes may be adjustable, for example by controlling the volume of the SNF/HAP dispersion during processing.

Figure 12:
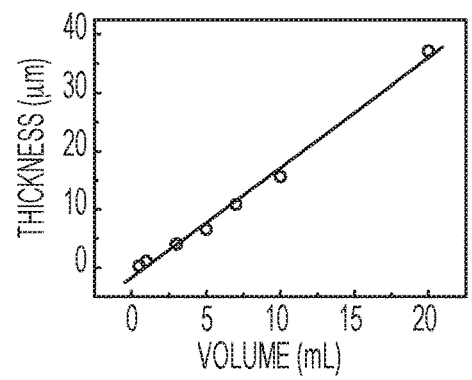
FIG. 12 shows a graph illustrating a linear relationship between the volume of SNF/HAP solution (0.2 wt %) and the resultant membrane thickness.

Example membranes can be formed by vacuum filtration. In some specific implementations, 3 mL of SNF/HAP dispersion can generate a membrane that is approximately 4 μm thick using a filtration mold that is 3.5 cm in diameter. The volume of the dispersion (with a concentration of ~0.2 wt %) can be linearly correlated to membrane thickness. FIG. 12 shows a graph illustrating a linear relationship between the volume of SNF/HAP solution (0.2 wt %) and the resultant membrane thickness.

Figure 13:
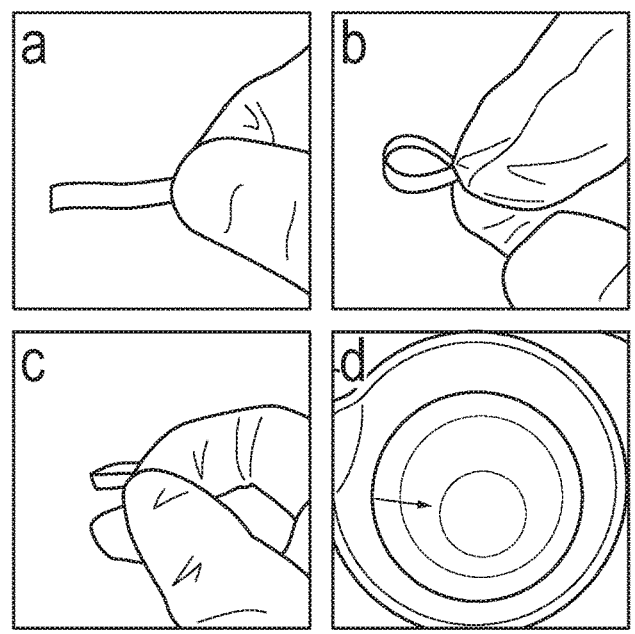
FIG. 13, panel a, shows a photograph of an example membrane after cutting. Panel b shows a photograph of an example membrane during bending. Panel c shows a photograph of an example membrane twisting. Panel d shows a photograph of an example membrane after being immersed in water for 1 month.
Figure 14:
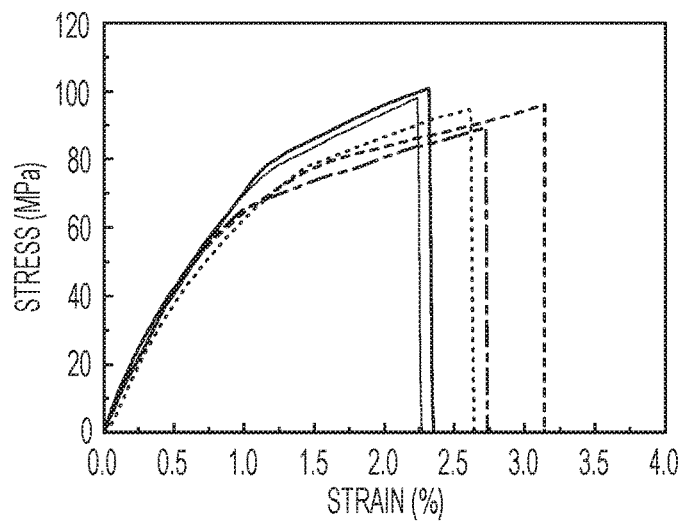
FIG. 14 shows a graph illustrating stress-strain curves of an example SNF/HAP membrane.

Example SNF/HAP membranes with thickness larger than 4 μm can be easily moved from the substrate and can even undergo cutting, bending and twisting without damage FIG. 13 shows photographs of SNF/HAP membranes after moving from substrate with a thickness of 4 μm. FIG. 13 shows a membrane after cutting (FIG. 13, panel a), during bending (FIG. 13, panel b) and twisting (FIG. 13, panel c). Moreover, the membranes can be stable in water without dissolution for more than one month at room temperature (FIG. 13, panel d). This property may ensure durability of membranes during the standby and purification processes. Tensile tests carried out to measure the mechanical properties of the materials. FIG. 14 shows a graph illustrating stress-strain curves of an example SNF/HAP membrane with thickness of 37 μm. out at ~25° C. and 50% relative humidity with tensile speed of 1 mm/min$^{-1}$.

Example, 37-μm-thick membranes may have a modulus of 7.7±0.2 GPa, around 3 times higher than that of pristine self-assembled SNF (2.25±0.25 GPa) and liquid exfoliated SNF membrane (3.5±0.3 GPa). As for toughness, the SNF/HAP membranes may have values of 1.7±0.3 MJ/m$^3$, 10-100 times higher than that of SNF membranes (0.09 to 0.2 MJ/m$^3$). This property ensures the durability of SNF/HAP membranes during the standby and high pressure purification processes.

Figure 15:
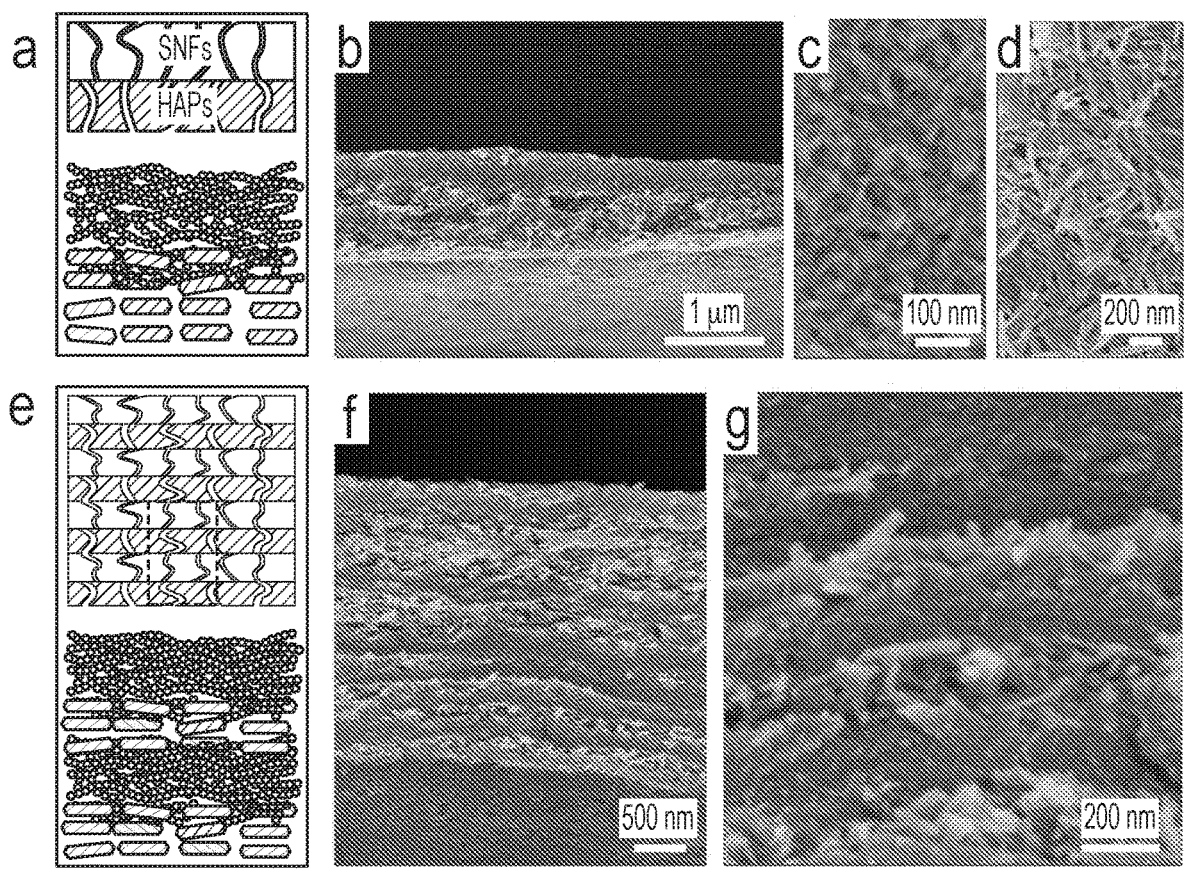
FIG. 15, panel a, shows a schematic representation of example double layer structures. Panel b shows a cross-sectional SEM image of a double layer membrane. Panel c shows a top view of an SEM images of an example SNF-rich layer of a membrane. Panel d shows a top view of an SEM images of an example HAP-rich layer of a membrane. Panel e shows a schematic representation of example multilayer structures. Panel f shows a cross-sectional SEM image of an example multilayer membrane. Panel g shows a high resolution cross-sectional SEM image of an example multilayer membrane.

The technologies described herein may include multilayered protein and/or mineral materials. Example SNF/HAP membranes show highly ordered multilayer structures with alternated HAP and SNF layers, each layer having an approximate thickness of 200 nm (a 4-μm-thick membrane as an example, FIG. 6, panel b). The number of layers may be tunable, for example by changing consumption of dispersion. FIG. 15 depicts images of multilayer structures of SNF/HAP membranes. FIG. 15, panels a-d show the double-layer structure of the SNF/HAP membranes formed through vacuum filtration of 1 mL of dispersion. FIG. 15, panel a shows a schematic representation of example double layer structures. The top layer is the SNF-rich layer with small pore sizes. The bottom layer is the HAP layer with larger pore sizes. FIG. 15, panel b shows a cross-sectional SEM image of a double layer membrane. FIG. 15, panel c and FIG. 15, panel d are top view SEM images of SNF-rich and HAP-rich layer, respectively. FIG. 15, panels e-g show a multilayer structure of a SNF/HAP membrane generated from 3 mL SNF/HAP dispersion using a 3.5 cm diameter mold. FIG. 15, panel e shows a schematic representation of exemplary multilayer structures. FIG. 15, panel f shows a cross-sectional SEM image of an example multilayer membrane. FIG. 15, panel g shows a high resolution cross-sectional SEM image of an example multilayer membrane. False color is used in SEM images. In an example implementation, 1 mL of ~0.2 wt % dispersion of SNF/HAP is used to generate a double-layer membrane, with HAP settling in the bottom layer and the SNFs remaining on the top (FIG. 15, panel a, FIG. 15, panel b). Each layer has a similar thickness of approximately 500 nm. Both layers have uniform dispersions of SNFs and HAPs, respectively, but they show distinct pore sizes (FIG. 15, panels c and d). The SNF layer has a narrow pore size distribution with a diameter of 8±2 nm (could serve as size-selectivity layer). In contrast, the HAP layer has a larger pore size distribution with a diameter of 28±5 nm (can enhance the water permeation). By progressively adding the volume of the SNF/HAP dispersion, the number of layers can be increased and can reach tens of layers (FIG. 15, panels f and g). The alternating arrangement of SNFs and HAPs layers can be observed in all cases.

Figure 16:
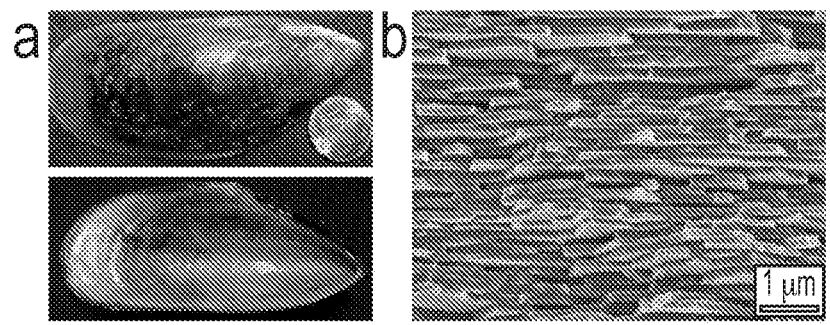
FIG. 16, panel a, shows photographs of a mussel shell. Panel b shows a cross-sectional SEM image of a mussel shell.
Figure 17:
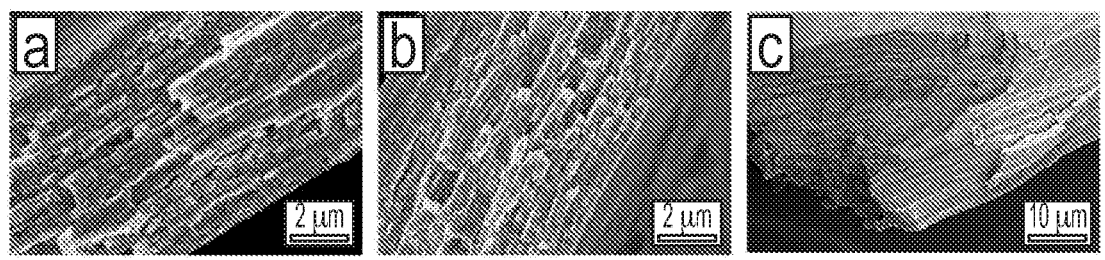
FIG. 17, panel a, shows a SEM image of a SNF/HAP membrane prepared from 7 mL, SNF/HAP dispersion (~0.2 wt %). Panel b shows an SEM image of a SNF/HAP membrane prepared from 10 mL SNF/HAP dispersion (~0.2 wt %). Panel c shows an SEM image of a SNF/HAP membrane prepared from 20 mL SNF/HAP dispersion (~0.2 wt %).
Figure 18:
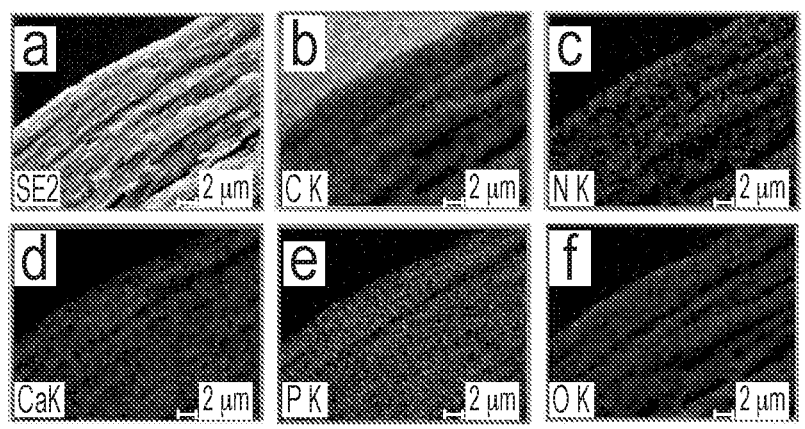
FIG. 18, panel a, shows an SEM image of a sample section of an example membrane. Panel b shows an elemental map for carbon of a sample section of an example membrane. Panel c shows an elemental map for nitrogen of a sample section of an example membrane. Panel d shows an elemental map for calcium of a sample section of an example membrane. Panel e shows an elemental map for phosphorus of a sample section of an example membrane. Panel f shows an elemental map for oxygen of a sample section of an example membrane.

Example SNF/HAP membranes may have highly ordered multilayer structures and show nacre-like brick-and-mortar structure. FIG. 16 shows the multilayer structure of nacre. FIG. 16, panel a shows photographs of a mussel shell. FIG. 16, panel b shows a cross-sectional SEM image of a mussel shell. The clear multilayer brick-and-mortar structure can be found, the thickness of each layer is about 200-400 nm. The numbers of the layers can increased with more volume of SNF/HAP solution to prepare the membranes. FIG. 17 shows SEM images of SNF/HAP membranes prepared from (a) 7 mL, (b) 10 mL and (c) 20 mL SNF/HAP dispersion (~0.2 wt %) using a filtration mold with inner diameter of 3.5 cm. FIG. 18 shows results of an elemental analysis of cross-sections of example SNF/HAP membranes. FIG. 18, panel a shows an SEM image of a sample section of an example membrane. Elemental maps are shown for carbon (FIG. 18, panel b), nitrogen (FIG. 18, panel c), calcium (FIG. 18, panel d) phosphorus (FIG. 18, panel e), and oxygen (FIG. 18, panel f). Example membranes show a brick-and-mortar-like structure with alternating SNF and HAP layers (FIG. 17), suggesting by both geometric feature and heterogeneous element distributions (FIG. 18).

EXAMPLES

An example multilayer nanoporous membrane production and application is described herein.

Silk nanofibril (SNF) solution can be prepared using an example process as described herein. *Bombyx mori* (*B. mori*) silkworm cocoon silk fibers are degummed by boiling in two 30 min changes of 0.5% (w/w) $NaHCO_3$ solution. The degummed silk fibers are washed with distilled water and allowed to air dry at room temperature. Next, a 10% (w/v) solution of degummed silk fibroin (SF) in aqueous 9.3 mol $L^{-1}$ LiBr solution is prepared by heating to 60° C. for 1 h. This solution is dialyzed with deionized water at room temperature to yield SF solution with a protein concentration ~5 wt %. In order to grow SNFs, this solution is further adjusted to 0.1 wt % SF in aqueous solutions and is incubated without any perturbation at 60° C. over 7 days. The structural details of SNFs can be characterized by Atomic Force Microscopy (AFM).

Hydroxyapatite (HAP) nanocrystals can be prepared via a biomineralization approach using an example process as described herein. For example, 6 mL 0.2 M $CaCl_2$ is added to 100 mL SNF solution (0.1 wt %) under continuous stirring or agitation. Five minutes later, 6 mL 0.2 M $Na_2HPO_4$ is introduced, and the mixture is incubated at 37° C. for one week to grow the HAP nanocrystals. The synthetic HAP nanocrystals can be confirmed by X-ray diffraction (XRD) measurements. Their structural features can be disclosed by Ultra 55 field emission scanning electron microscopy (SEM).

Example SNF/HAP membranes can be fabricated by vacuum-filtration of the dispersions through a vacuum filtration assembly and polycarbonate filtration membranes (pore size, 200 nm; diameter 47 mm).

The technologies described herein may include methods for forming multilayered protein and/or mineral membranes. Membranes, e.g., SNF/HAP membranes, may be generated and/or deposited using one or more rapid and diversified formation processes.

Figure 19:
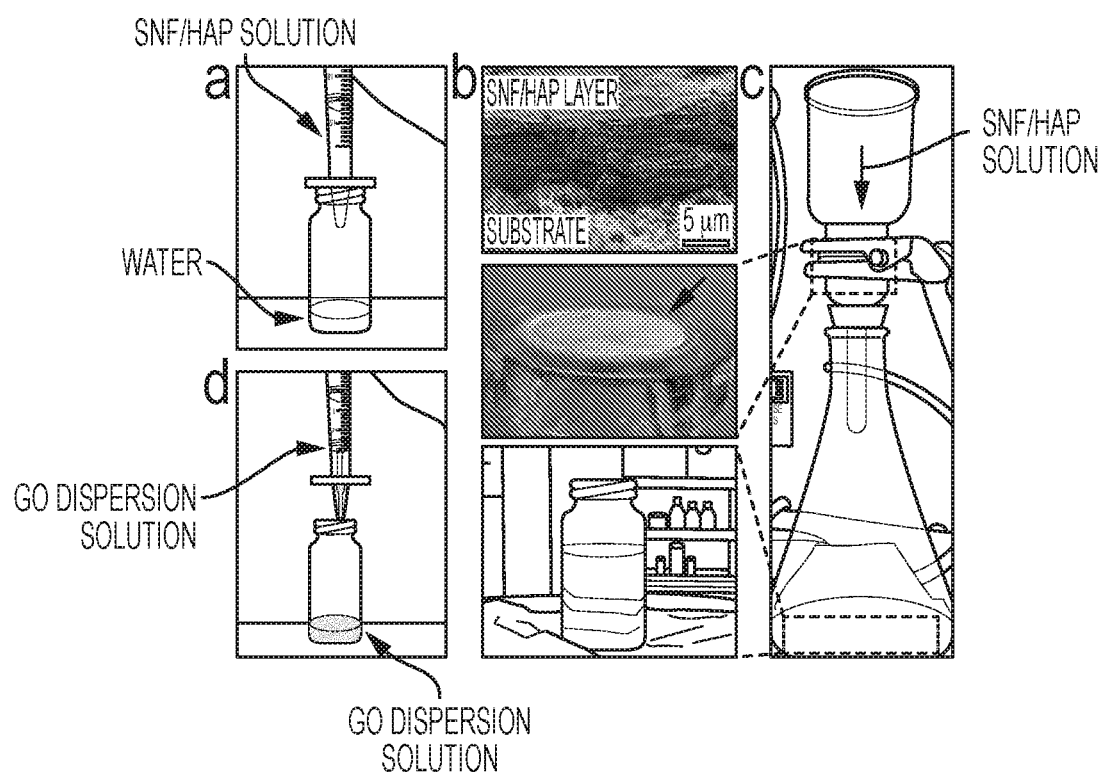
FIG. 19, panel a, shows a photograph of an example SNF/HAP membrane on a 5 µm thick PVDF marcofilter membrane. Panel b shows an SEM image of an example SNF/HAP membrane on a 5 µm thick PVDF marcofilter membrane. Panel c shows a photograph of an example SNF/HAP membrane formed on a straight-wall, glass funnel, with two expanded photos sowing components thereof. Panel d shows a photograph of an example SNF/HAP membrane on a 5 µm thick PVDF marcofilter membrane illustrating that graphene oxide (1 mg/mL) can pass through a syringe filter with a pore size of 5 µm.

In an example, SNF/HAP multilayer membranes are be formed through extrusion, e.g., cylinder extrusion, and vacuum filtration. SNF/HAP composites can even stand on a substrate with pore size much larger (e.g., more than 100 times) than pore size of SNF and HAP. The top-down SNF dispersion can prepared using various methods, In an example implementation, degummed *Bombyx mori* silk fibres are immersed in hexafluoroisopropanol (HFIP) solution with weight ratio of 1:30 and were mixed by vortexing. The sealed silk fibre/HFIP mixture is incubated at 60° C. to partially dissolve the silk fibres to silk microfibrils (SMFs). After 24 hours, the resultant SMF pulp blend is dried to evaporate the HFIP. After complete drying, the SMFs are placed in water with weight ratio of 1:200 with continuous stirring or shaking, followed by removal of undissolved silk. The SMFs/water mixture is sonicated at 120 μm amplitude and 20 KHz frequency, at intervals of 10 sec. After 1 h, the exfoliated SNFs dispersion can be harvested by centrifugation at 10,000 rpm for 20 min. In some implementations, membranes also can be formed directly on a commercial syringe filter, for example by hand-operated extrusion. Substrates include a 5 μm syringe macrofilter and 40-50 μm glass filters. FIG. 19 shows example SNF/HAP multilayer membranes generated using the example methods described herein. FIG. 19, panel a shows a photograph of an example SNF/HAP membrane on a 5 μm thick PVDF marcofilter membrane. Water can easily pass through this combined membrane. FIG. 19, panel b shows an SEM image of an example SNF/HAP membrane on a 5 μm thick PVDF marcofilter membrane formed through syringe extrusion. Pseudo-color applied to distinguish the SNF/HAP and syringe filter membranes. The cross-section of the SNF/HAP membrane indicates that the brick-and-mortar like structure even formed during simple hand-extrusion. FIG. 19, panel c shows a photograph of an example SNF/HAP membrane formed on a straight-wall, glass funnel with pore size of 40-50 μm after filtration of 20 mL~0.2 wt % SNF/HAP solution. The solution in the bottle is penetrant and transparent, indicating that the SNF/HAP composite is completely held by the glass funnel during filtration processing. FIG. 19, panel d shows a photograph of an example SNF/HAP membrane on a 5 μm thick PVDF marcofilter membrane illustrating that graphene oxide (1 mg/mL) can pass through a syringe filter with a pore size of 5 μm. The size of graphene oxide (~2 μm width) is smaller than pore size of syringe filter, and graphene oxide nanosheets do not form continuous network structure.

Figure 20:
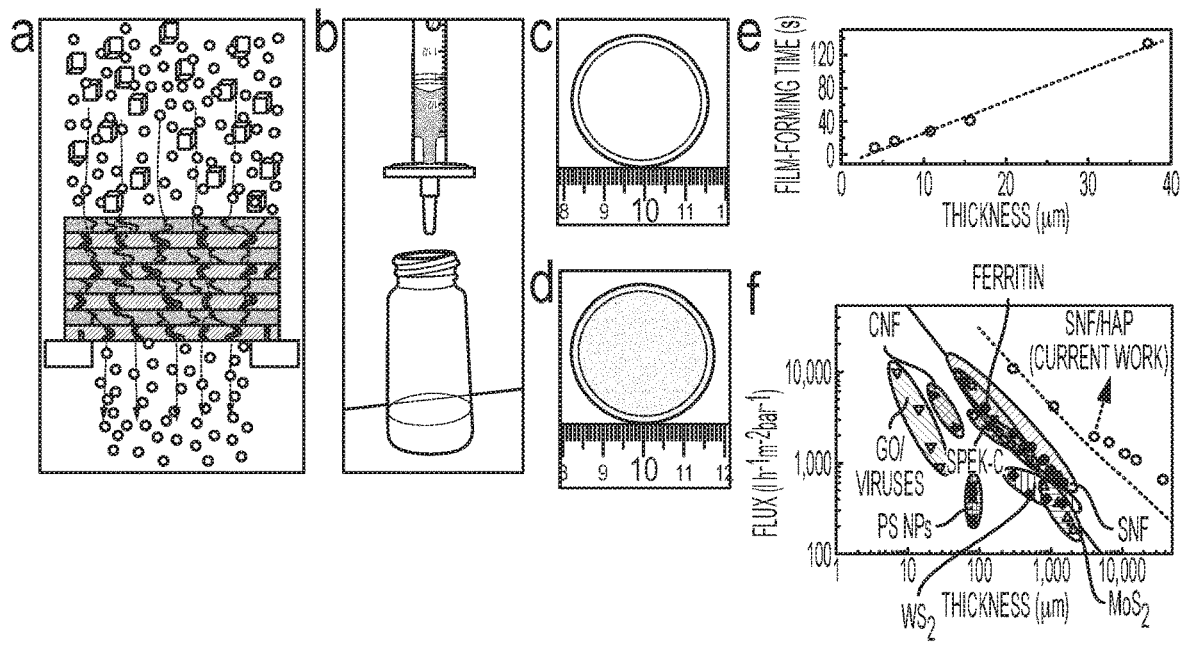
FIG. 20, panel a, shows a graphical cross-sectional representation of a multilayer SNF/HAP membrane for filtering various compounds. Panel b shows a photograph of a SNF/HAP based syringe nanofilter. Panel c shows a photograph showing a SNF/HAP nanofiltration membrane before filtration with 20 mL 5 mM Rhodamine B solution. Panel d shows photographs showing a SNF/HAP nanofiltration membrane after filtration with 20 mL 5 mM Rhodamine B solution. Panel e shows a graph illustrating the linear relationship between film thickness and film-formation process time. Panel f shows a graph illustrating thickness-dependent changes in permeability to pure water for the SNF/HAP membranes compared with membranes reported in the literature. Panel g shows a table illustrating separation performance of 4 µm thick SNF/HAP membranes for dyes, proteins and colloids. Panel h shows a graph illustrating Cyt. c separation performance of SNF/HAP membranes compared to performance of other filtration membrane materials.
Figure 20:
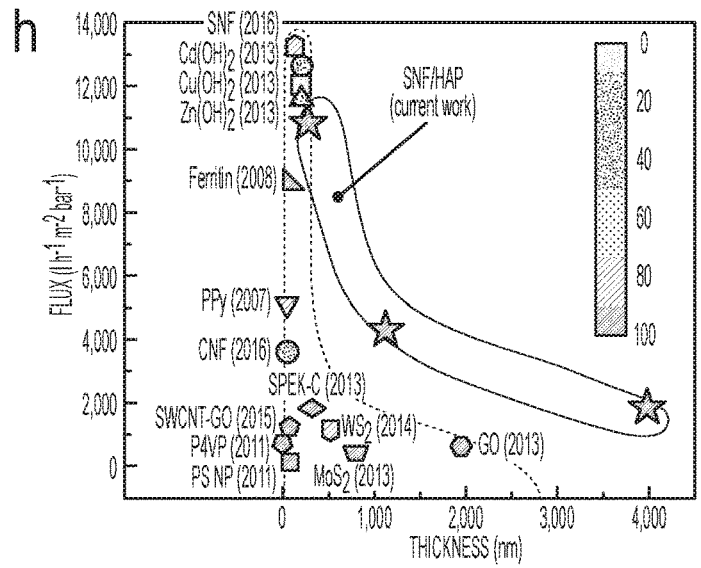

FIG. 20 shows separation performance of example SNF/HAP membranes. FIG. 20, panel a shows a graphical cross-sectional representation of a multilayer SNF/HAP membrane for filtering various compounds. FIG. 20, panel b shows a photograph of a SNF/HAP based syringe nanofilter, which can successfully reject Alcian Blue 8GX with a rejection of 98%. The detailed structures of SNF/HAP membranes formed on microfilters can be found in FIG. 19, panel b. FIG. 20, panels c and d show photographs of a SNF/HAP nanofiltration membrane before (FIG. 20, panel c) and after (FIG. 20, panel d) filtration with 20 mL 5 mM Rhodamine B solution. FIG. 20, panel e shows a graph illustrating the linear relationship between film thickness and film-formation process time. An example 4 μm thick membrane may only require 9 seconds under vacuum fabrication at 80 kPa to form on a substrate. FIG. 20, panel f shows a graph illustrating thickness-dependent changes in permeability to pure water for the SNF/HAP membranes compared with membranes reported in the literature. The blue dash dot line is a fitted curve using the Hagen-Poiseuille equation with uniform structure. The red solid line is a fitted curve using Eq. (1) for multilayer membrane. FIG. 20, panel g shows a table illustrating separation performance of 4 μm thick SNF/HAP membranes for dyes, proteins and colloids. Molecular sizes of dyes are calculated using Materials studio 7.0, the sizes of proteins are calculated from their PDB files. The flux listed in the Table is calculated from a filtration of model compound solutions. The flux of dye solution is comparable to the flux of pure water, except for Brilliant Blue G and Direct Red 81. These two solutions have a lower flux, likely due to their large molecular size, which would be responsible for blocking the pores of membranes. FIG. 20, panel h shows a graph illustrating Cyt. c separation performance of SNF/HAP membranes compared to performance of other filtration membrane materials. The rejection is represented by the color of the pattern. The blue and red are 0% and 100% rejection, respectively (Abbreviations: $Cd(OH)_2$, $Cu(OH)_2$ and $Zn(OH)_2$ are $Cd(OH)_2$, $Cu(OH)_2$ and $Zn(OH)_2$ nanofibers; SNF, top-down prepared silk nanofibrils; CNF, cellulose nanofibers; PPy, polypyrrole-coated cooper hydroxide nanostrands; SWNCT-GO, single wall carbon nanotubes and graphene oxide sheets composites; GO, graphene oxide sheets; PS NP, polystyrene nanoparticles; P4VP, cross-linked poly(4-vinylpyridine); SPEK-C, sulfonated polyetherketone with cardo groups; $WS_2$, chemically exfoliated tungsten disulfide nanosheets; $MoS_2$, atom-thick molybdenum disulfide sheets).

In some implementations, multilayer nanoporous membranes can enhance fluid flux across a membrane compared to other filtration techniques. In an example implementation, the flux through a 0.3 μm thick SNF/HAP membranes can be up to 10,800 L h−1 m−2 bar−1, more than 1,000 times greater than those of commercial filtration membranes and over 5 times higher than those of the most advanced recently reported ultrathin membranes with similar thickness (FIG. 20, panel f).

Figure 21:
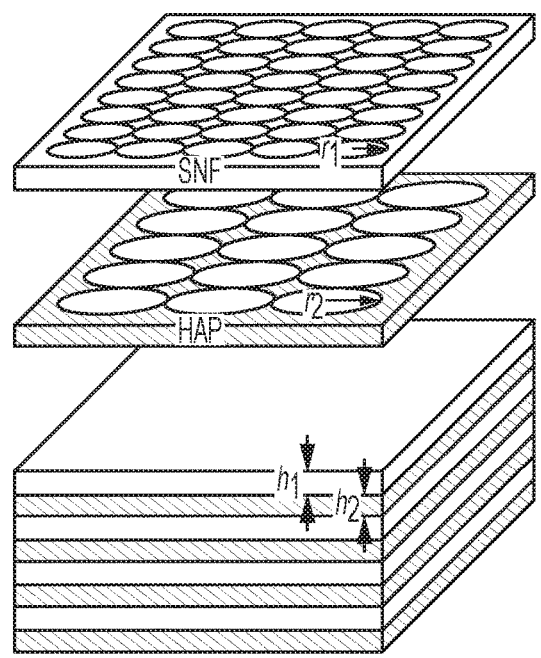
FIG. 21 shows a schematic representation of an exemplary multilayer membrane.

Flux across multilayer nanoporous membranes can be modeled using a computational model. An example filtration model is schematically shown in FIG. 21). The membrane is composed of alternative SNF with thickness $h_1$ and HAP with thickness $h_2$. The radius of the pores is $r_1$ (SNF) and $r_2$ (HAP). The density of pores in the plane was $\alpha_1$ (SNF) and $\alpha_2$ (HAP). The total thickness of the membrane is H.

The Reynolds number of flow in the pores is computed via $$\text{Re} = \frac{\rho v D}{\mu},$$

where $\rho=1\times10^3$ kg·m$^3$ and $j=0.001$ kg·m·s$^{-1}$ are the density and viscosity of water obtained at room temperature, respectively. For filtration with the current membrane, a velocity $v<1$ m·s$^{-1}$ and pore diameter D<30 nm is applied to all the study cases. Thus Re<0.03 is obtained, which is in the laminar flow region. Hence, the Hagen-Poiseuille equation is applicable and the pressure drop for a single pore in the SNF layer is given by $$\Delta P_{SNF} = \frac{8k_1 \mu h_1 Q_1}{\pi r_1^4} \quad (18)$$

Where $Q_1$ is the volume rate through a pore and $k_1$ accounts for the pore shape. The total volume flow rate is $Q=\alpha_1 Q_1 A$, where A is the total cross-section area of the membrane for filtration. Similarly, the pressure drop for a single pore in the HAP layer was given by $$\Delta P_{HAP} = \frac{8k_2 \mu h_2 Q_2}{\pi r_2^4} \quad (19)$$

And the total volume rate is kept constant through layers, thereby:

$$Q_2 = \alpha_1 Q_1 / \alpha_2$$

The total pressure drop of the entire membrane is given by $$\Delta P = \Sigma(\Delta P_{SNF} + \Delta P_{HAP}) = \left(\frac{8h_1}{\beta_1 r_1^4} + \frac{8h_2}{\beta_2 r_2^4}\right) \frac{\mu H Q}{A\pi(h_1 + h_2)} \quad (21)$$

Where $\beta_1 = \alpha_1/k_1$ and $\beta_2 = \alpha_2/k_2$. The flux of the water flow was therefore given by $$f_{flux} = \frac{Q}{A\Delta P} = \frac{\pi(h_1 + h_2)}{8\mu H \left(\frac{h_1}{\beta_1 r_1^4} + \frac{h_2}{\beta_2 r_2^4}\right)} \quad (22)$$

Figure 22:
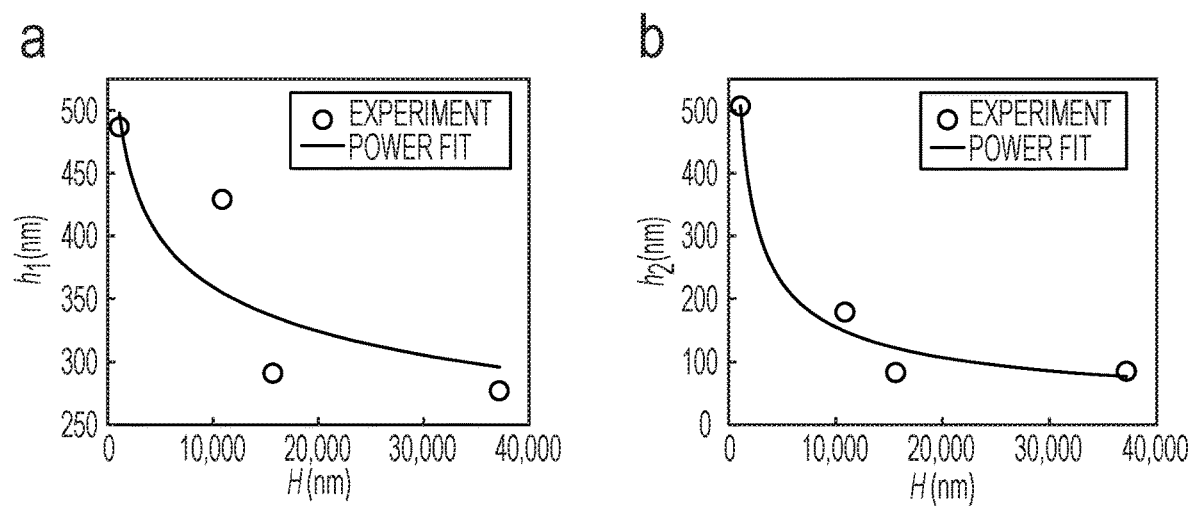
FIG. 22, panel a, shows a graph illustrating parameter $h_1$ for SNF thickness and $h_2$ fitted by power law according to experimental measurements. Panel b shows a graph illustrating parameter $h_2$ for HAP thickness fitted by power law according to experimental measurements.

Parameters $h_1$ and $h_2$ are fitted by power law according to experimental measurements, as shown in FIG. 22, for SNF thickness (FIG. 22, panel a) and HAP thickness (FIG. 22, panel b).

$$h_1 = 1405.9 H^{-0.15} \quad (23)$$

$$h_2 = 22072.6 H^{-0.54} \quad (24)$$

Example values for a membrane are shown in Table 3

TABLE 3

| Geometric symbol | Experimental measurement value |
|---|---|
| Thickness of SNF $h_1$ (nm) | 1405.9 H$^{-0.15}$ |
| Thickness of HAP $h_2$ (nm) | 22072.6 H$^{-0.54}$ |
| Radius of the pores in SNF $r_1$ ± sd (nm) | 4 ± 1 |
| Radius of the pores in HAP $r_2$ ± sd (nm) | 14 ± 2.5 |

Figure 23:
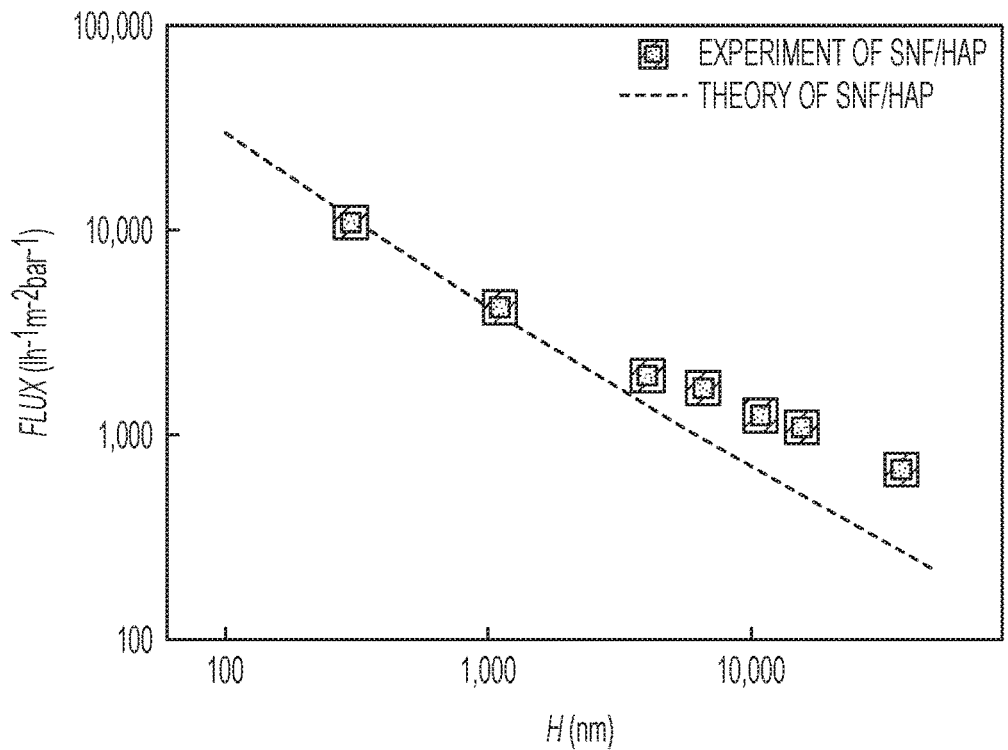
FIG. 23 shows a graph comparing theoretical fluxes through example SNF/HAP membranes with experimental results.

Putting (23) and (24) into (22) allowed to find the numerical value of $\beta_1$ and $\beta_2$ by fitting according to the data points and $\beta_1=4\times10^{-18}$ m$^{-2}$ and $\beta_2=4\times10^{-14}$ m$^{-2}$ shows a good fit with experiments. FIG. 23 shows a graph comparing theoretical fluxes through example SNF/HAP membranes with experimental results. Without wishing to be bound by theory, one reason $\beta_1 \gg \beta_2$ is that the $r_1 < r_2$ leads to $\alpha_1 > \alpha_2$. Another reason may be that the irregular geometry of the pores in HAP make its drag force much larger than idealized round channel and thus $k_2 \gg k_1$.

For homogeneous membrane with uniform channels, Eq. (18) could be simply reduced to the classical Hagen-Poiseuille equation.

$$f_{flux} = \frac{Q}{A\Delta P} = \frac{\pi \beta r^4}{8\mu H} \quad (25)$$

This indicates that $f_{flux} \sim H^{-1}$, and that having two layers in the SNF-HAP composite help to maintain the flux once the membrane is thicker than the membrane made of pure SNF or HAP. It is noted that $\beta$ relates to the membrane porosity and pore shape, and its numerical value can be determined by fitting according to the flux-H relationship. Therefore, for pure SNF or HAP membranes their $\beta$ and r values can be different from those of the SNF or HAP layers within the multilayer assembly. It may be that the interaction between SNF and HAP makes the combination membrane more water permeable, as the pure SNF membrane may exhibit weaker water permeability than the SNF/HAP membrane of the same thickness.

These results indicate that the multilayer structures in the membrane can enhance the flux of water through the membranes with a similar diameter and thickness.

In some implementations, multilayer nanoporous membranes can enhance separation and/or adsorption performance compared to other filtration techniques, for example of biological or medical materials.

In an example process, separation is performed on a vacuum filtration device (e.g., a glass vacuum filtration assembly device, membrane diameter of 47 mm, inner diameter of funnel top 35 mm). Water (10 mL) is filtered across the membrane to measure the pure water flux (J, L m$^{-2}$ h$^{-1}$ bar$^{-1}$), which can be calculated by J=V/(Atp), where V is the volume of the water filtered (L), A is the effective membrane filtration area (m$^2$), t is the filtration time (h), and p is the suction pressure across the membrane (bar). The filtration area of the example filter holder is 9.62 cm$^2$ and the porosity of the PC membrane is 10%. The effective surface area is 0.962 cm$^2$. Permeation is characterized by UV-vis spectrophotometer and inductively coupled plasma atomic emission spectrometry. The rejection (R, %) can be calculated by $$R = \left(1 - \frac{C_p}{C_f}\right) \times 100\%$$

Where $C_f$ and $C_p$ are the concentrations of compounds in the feed and permeate, respectively.

Figure 24:
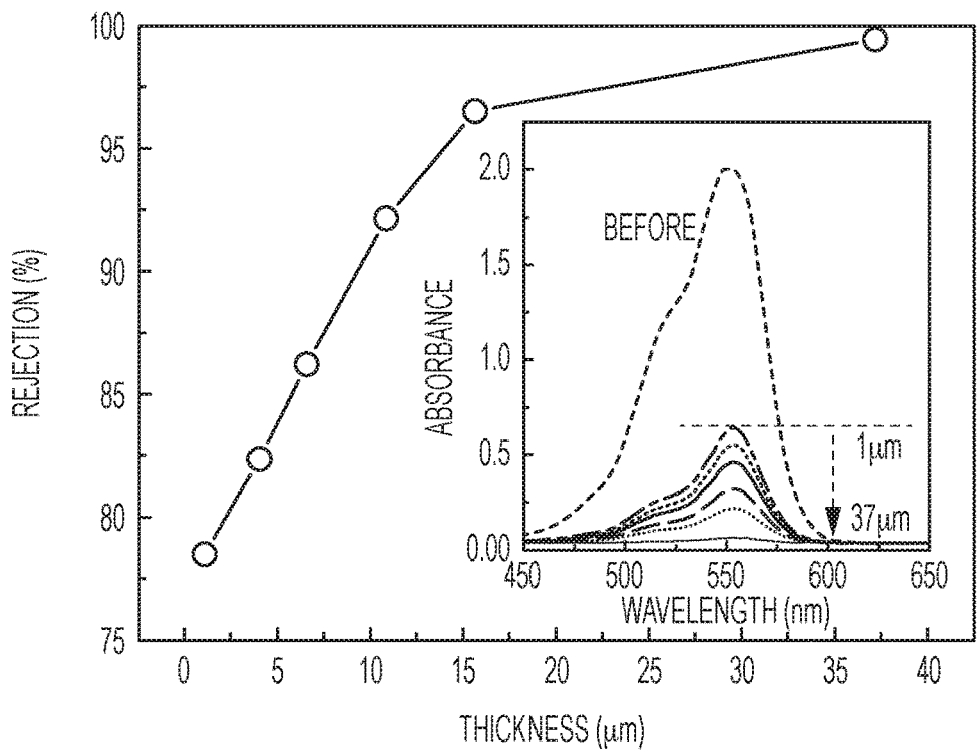
FIG. 24 shows a graph illustrating the rejection of 10 mL 5 µM Rhodamine B aqueous solution by example SNF/HAP membranes with different thicknesses.

Dye separation efficiency is usually unsatisfactory for most ultrathin filtration membranes. However, both the SNF and HAP components in the SNF/HAP membranes may have the capability to capture different dyes and may thus be suitable for separating dyes from water. Separation performance of the 4-μm-thick SNF/HAP membranes through pressure-driven filtration is assessed as shown in FIG. 4. The membranes exhibit efficient separation for most dyes, for example Orange G, with at least a 50±3% rejection. A 10 mL 5 μM Rhodamine B aqueous solution can be used to study the influence of membrane thickness on separation performance FIG. 24 shows a graph illustrating the rejection of 10 mL 5 μM Rhodamine B aqueous solution by example SNF/HAP membranes with different thicknesses. The insert plot shows UV-vis absorption changes of an aqueous solution of rhodamine B after filtration with SNF/HAP membranes with different thicknesses. The UV-vis spectra with an absorption at 554 nm drop gradually with increasing membrane thickness from 1 to 37 μm. The calculation demonstrate that rejection reached equilibrium (rejection: 96%) at an example membrane with thickness of 16 μm.

Figure 25:
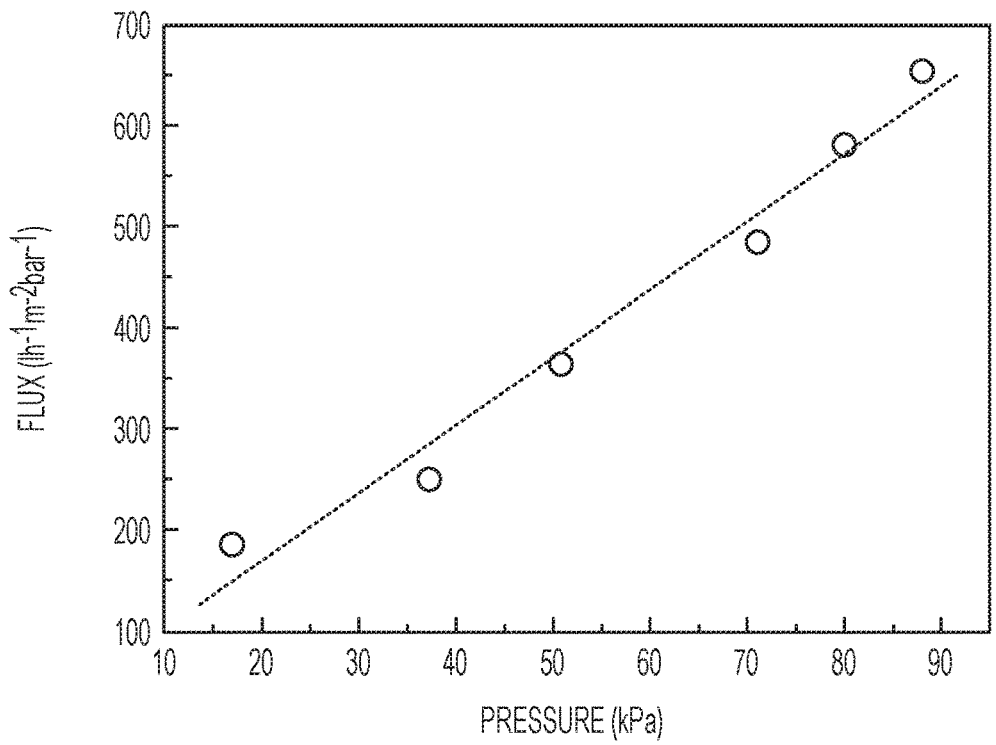
FIG. 25 shows a graph illustrating the relationship between pressure and pure water flux of ejection in an example 37-µm-thick SNF/HAP membrane.
Figure 26:
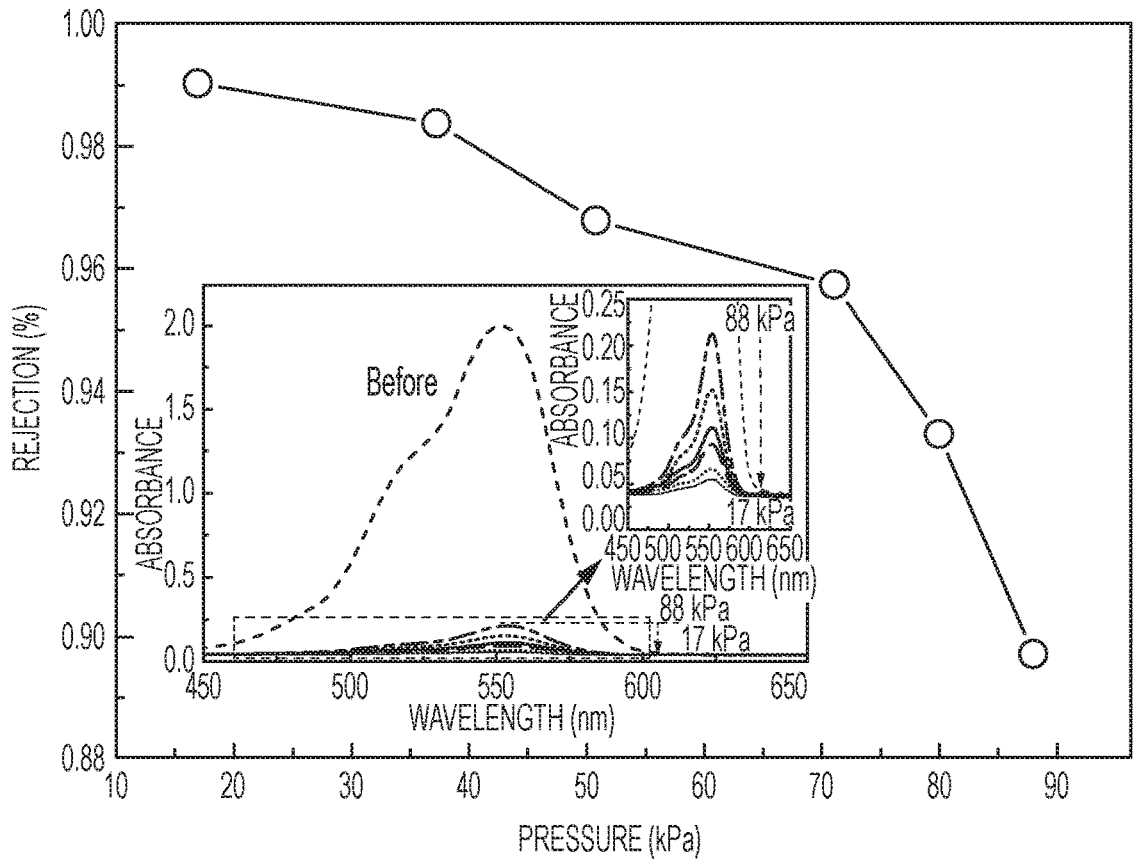
FIG. 26 shows a graph illustrating the rejection of 10 mL 5 µM Rhodamine B aqueous solution by an example 37 µm thick SNF/HAP membrane under several different applied pressures.

The effect of applied pressure on pure water flux and the separation performance of SNF/HAP membranes can be estimated by using 37-μm-thick SNF/HAP membranes. FIG. 25 shows a graph illustrating the relationship between pressure and pure water flux of ejection in an example 37-μm-thick SNF/HAP membrane. A linear relationship between pressure and pure water flux can be observed. FIG. 26 shows a graph illustrating the rejection of 10 mL 5 μM Rhodamine B aqueous solution by an example 37 μm thick SNF/HAP membrane under several different applied pressures. The insert plot shows UV-vis absorption changes of an aqueous solution of rhodamine B after filtration with 37 μm thick SNF/HAP membranes under several different applied pressures. As shown in FIG. 26, the rejection of Rhodamine B declines continually with increased pressure in the range of 17-88 kPa. This tendency is different from that in more traditional polymer-based membranes, because the rejection rate usually increases with pressure due to compression and/or densification of the porous structures. In addition, the contact/interaction time of dye and membrane components may also play important roles in the pressure response of membranes, in particular, for SNF/HAP membranes. The separation performance of SNF/HAP membranes may not only influenced by their pore size but also by their adsorption feature. The adsorption capability of membranes may be positively related to contact/interaction time between dyes and membranes. Thus this contact time between dyes and membranes may be shortened by increasing the pressure as a result that less dye would be removed.

Figure 27:
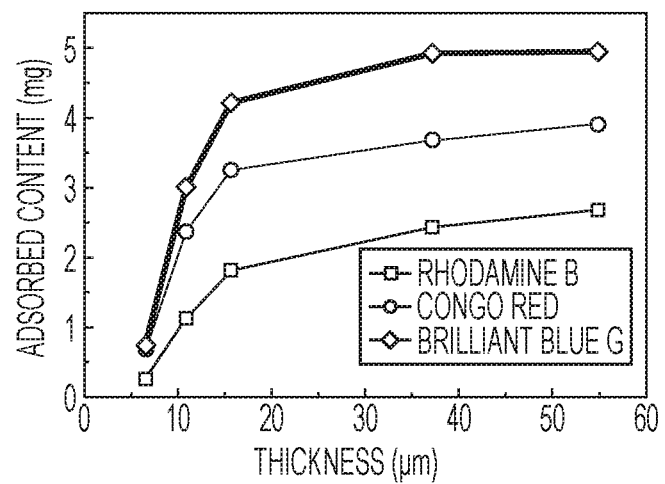
FIG. 27 shows a graph illustrating the relationship between example membrane thickness and adsorbed dye content.

To evaluate dye adsorption capability of SNF/HAP membranes, the relationship of membrane thickness and dye adsorption capability and the related adsorption equilibrium isotherms can be assessed for example membranes of different thickness, from 1 to 37 μm. FIG. 27 shows a graph illustrating the relationship between example membrane thickness and adsorbed dye content. Rhodamine B, Congo Red and Brilliant Blue G dyes have different molecular sizes, charge and structural features (FIG. 20, panel g). The initial concentration and volume of dye in aqueous solutions are set at 150 μM and 40 mL, respectively. In this example, freshly prepared SNF/HAP membranes are directly transferred to dye aqueous solutions and allowed to stand at room temperature for 48 hours to reach adsorption equilibrium. In this example, the dye adsorption sharply increases when the thickness of membranes was lower than 20 μm and reach equilibrium with increasing thickness. Specifically, a 37-μm-thick membrane adsorbs 2.43 mg Rhodamine B, and theoretically would have capability to remove 1 L 5 μM Rhodamine B aqueous solution (the concentration used for filtration in this example) even without considering the size-exclusion of membranes.

In order to quantitatively evaluate the adsorption capacity of the SNF/HAP membranes, equilibrium data can be fitted by Langmuir and Freundlich isotherm models.

These pseudo-second (PS) order models have can be exploited to analyze the experimental data. The pseudo-second order equation based on adsorption equilibrium capacity assumes that the rate of occupation of desorption sites is proportional to the square of the number of unoccupied sites. A linear form of pseudo second-order kinetic model is express by eq.

$$\frac{t}{q} = \frac{1}{k_2 q_e^2} + \frac{t}{q_e} \tag{1}$$

where $k_2$ is the rate constant (g mg$^{-1}$ min$^{-1}$) of pseudo second-order kinetic model for adsorption, and $q_e$ is the adsorption capacity calculated by the pseudo-second order model (mg g$^{-1}$).

To investigate the efficacy of adsorption, Langmuir and Freundlich models can be used to fit experimental data. The Langmuir model assumes that a monomolecular layer is formed when adsorption takes place without any interaction between adsorbed molecules. The form of the Langmuir isotherm can be represented by the following equation:

$$q_e = q_m \frac{K_L C}{1 + K_L C} \tag{2}$$

where $q_e$ is the amount of metal ions adsorbed per gram of adsorbent (mg g$^{-1}$), C denotes the equilibrium concentration of metal ions in solution (mg L$^{-1}$); $k_L$ represents the Langmuir constant (L mg$^{-1}$) that relates to the affinity of binding sites and $q_m$ is a theoretical limit of adsorption capacity when the monolayer surface is fully covered with metal ions to assist in comparison of adsorption performance (mg g$^{-1}$). The Freundlich model assumes a heterogeneous adsorption surface and active sites with different energy. The Freundlich model is given as:

$$q_e = K_F C^{1/n} \tag{3}$$

where $q_e$ is the amount of metal ions adsorbed per gram of adsorbent (mg g$^{-1}$); C is the equilibrium metal ion concentration in solution (mg L$^{-1}$); $K_F$ and n are the Freundlich constants, which represent the adsorption capacity and the adsorption strength, respectively. The magnitude of 1/n quantifies the favorability of adsorption and the degree of heterogeneity of the adsorbent surface.

The amount of adsorbed metal ions on the adsorbents (q, mg g$^{-1}$) can be calculated as follows:

$$q_t = (C_0 - C_t) \times \frac{V}{m} \quad (4)$$

where $C_0$ and $C_t$ are the metal ion concentrations (mg L$^{-1}$) at the beginning of the experiment and after a period of time t; V is the initial volume of the solution (L); and m is the adsorbent weight (g).

Figure 28:
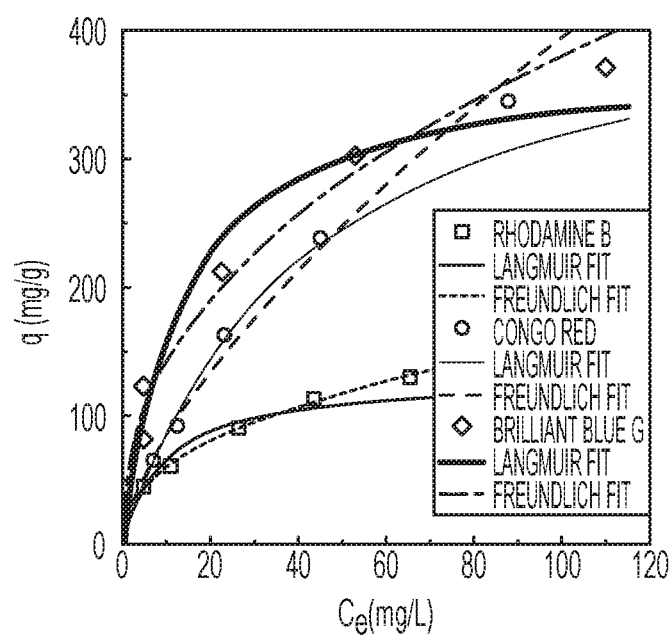
FIG. 28 shows a graph illustrating equilibrium adsorption isotherms of dyes adsorption on example SNF/HAP membranes.

FIG. 28 shows a graph illustrating equilibrium adsorption isotherms of dyes adsorption on example SNF/HAP membranes. Langmuir and Freundlich isotherm parameters of dyes adsorption on SNF/HAP nanocomposites are shown in Table 4).

TABLE 4

| Adsorbate | Langmuir model | | | Freundlich model | | |
|---|---|---|---|---|---|---|
| | $q_m$ (mg g$^{-1}$) | $K_L$ (L mg$^{-1}$) | $R_2$ | $K_F$ | 1/n | $R_2$ |
| RB | 129.4 | 0.107 | 0.94 | 23.04 | 0.42 | 0.99 |
| CR | 452.5 | 0.024 | 0.98 | 18.07 | 0.67 | 0.99 |
| BBG | 380.2 | 0.074 | 0.90 | 52.75 | 0.53 | 0.94 |

Comparison of the regression coefficients (R2) of both models show that the Freundlich isotherm model provide a better fit with the adsorption data. The Freundlich constant, n, in all cases is larger than 1, indicating favorable conditions for adsorption. The maximum adsorption capacity of example SNF/HAP membranes for Rhodamine B, Congo Red and Brilliant Blue G are shown in Table 4, indicating that the SNF/HAP membranes have excellent adsorption for dyes. Both the SNF and HAP components are negatively charged at neutral pH and are thus more likely to capture positively charged dyes. The theoretical maximum adsorption capacity of positively charged Rhodamine B is lower than the negatively charged Congo Red. This difference suggests that other molecular interactions (such as dye-membrane hydrophobic interactions and chemical interaction of dyes) also affect the adsorption equilibrium isotherms.

Figure 29:
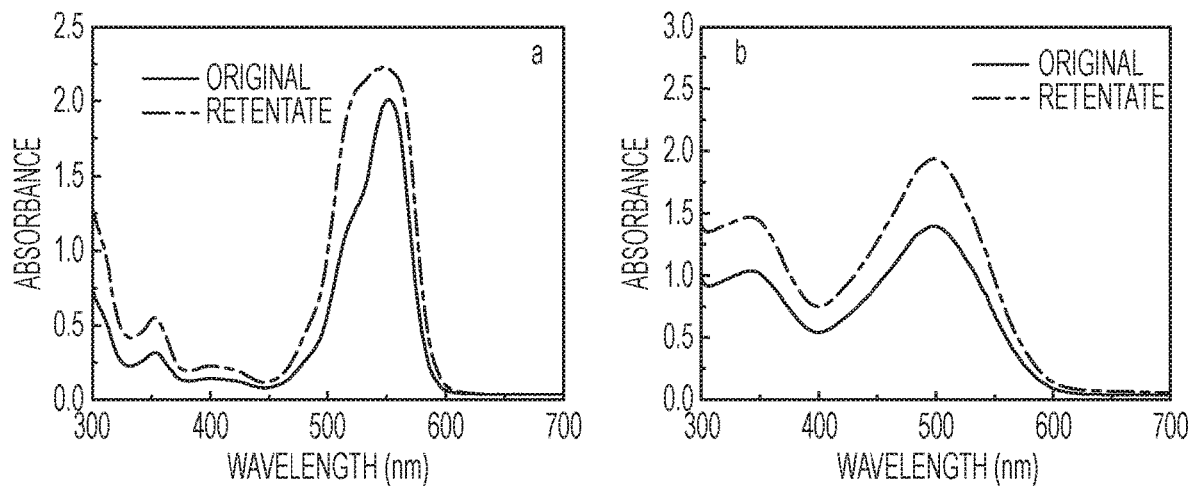
FIG. 29, panel a, shows a graph illustrating the UV-vis spectra of starting and retentate solution of Rhodamine B after 12 h filtration. Panel b shows a graph illustrating the UV-vis spectra of starting and retentate solution of Congo Red after 12 h filtration.
Figure 30:
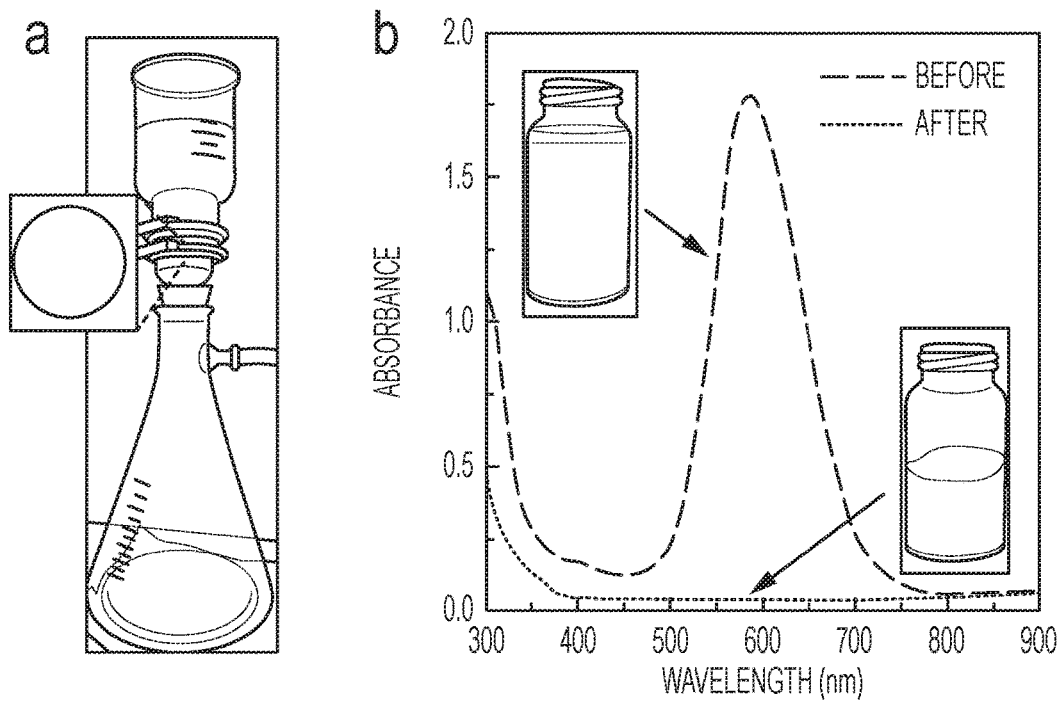
FIG. 30, panel a, shows a photograph of an example SNF/HAP membrane setup used for large volume permeate filtration. Panel b shows a graph illustrating UV-vis spectra of Brilliant Blue G aqueous solution collected from before and after filtration using an example membrane.

Maximum adsorption capacity tendency in equilibrium adsorption isotherms is Congo Red>Brilliant Blue G>Rhodamine B, which is different from separation performance recorded by filtration experiments, which shows sequence of Brilliant Blue G>Rhodamine B>Congo Red. This may imply that the size-exclusion affection also contributes to the final separation performance. The UV-vis absorbance of starting and retentate solution of dyes (Rhodamine B and Congo Red) agree with the results from adsorption isotherms experiments. FIG. 29 shows a graph illustrating the UV-vis spectra of starting and retentate solution of Rhodamine B (FIG. 29, panel a) and Congo Red (FIG. 29, panel b). The concentration of Rhodamine B and Congo Red are 5 μM and 17 μM, respectively. The starting volume of dye solutions are 100 mL. The retentate solutions are collected after 4 h filtration. As shown in FIG. 29, the retentate solution of both dyes indeed have higher absorbance than the starting solution. Moreover, in large volume permeate filtration example a comparatively large amount of Brilliant Blue G aqueous solution (250 mL 398 μM) is used for filtration and separation. In this example, the solution is allowed to pass through the membrane in 12 h. The SNF/HAP membranes reject all of the dye even using this large volume permeate. The membrane after filtration remains intact and can be easily moved from the filtration device. FIG. 30 shows an example SNF/HAP membrane used for large volume permeate filtration. FIG. 30, panel a shows a photograph of an example SNF/HAP membrane setup used for large volume permeate filtration. This example SNF/HAP membrane setup successfully rejects Brilliant Blue 8GX. FIG. 30, panel b shows a graph illustrating UV-vis spectra of Brilliant Blue G aqueous solution collected from before and after filtration. The content of Brilliant Blue G in such a solution is higher than the adsorption capability of an example 37-μm-thick membrane, but the rejection remains at 100%. This result further indicates the size exclusion effect of the membranes for filtration experiments. In addition, charge and pore size of dyes also contribute to separation performance of membranes under high vacuum pressure conditions. Therefore, example membranes show higher rejection for positively charged dyes (e.g., Rhodamine B, rejection of 84±1%) than negative charged dyes (e.g., Congo Red, rejection of 67±4%) with similar molecular sizes. In addition, small dyes (e.g., Eosin B, size of 1.1×1.0 nm; Orange G, size of 1.3×0.8 nm) can pass through membranes more easily, with rejection rates of 60±2% and 50±3%, respectively. In contrast, larger dyes (e.g., Alcian Blue 8GX, size of 2.5×2.3 nm; Brilliant Blue G, size of 2.3×1.8 nm) are nearly completely rejected during example filtration processes, with rejection rates of 94±3% and 92±1%, respectively.

The separation performance of membranes for small molecules (1-tryptophan), large proteins (cytochrome c, Cyt. c; bovine serum albumin, BSA) and colloids (gold nanoparticles) confirms size selectivity. In an example separation process, small L-tryptophan molecules (rejection: 19±4%) passed freely through the channels (FIG. 20, panel g). In contrast, Cyt.c, BSA and gold nanoparticles, which are all larger size, are almost completely rejected (rejection larger than 96±2%). Additionally, the rejection of all dyes (FIG. 20, panel g) is larger than 50%, which is superior to that found in other polymer-based membranes and similar to other types of protein based ultrafiltration membranes, such as ferritin and SNF membranes. A comparison of separation efficiencies of SNF/HAP membranes for Cyt. c with other water purification membranes reported in the literature is shown in FIG. 20, panel h. The example SNF/HAP membranes extend the "instep" pattern of the reported thickness versus flux relationship and exhibit a more effective integration of thickness, flux and separation performance.

Figure 31:
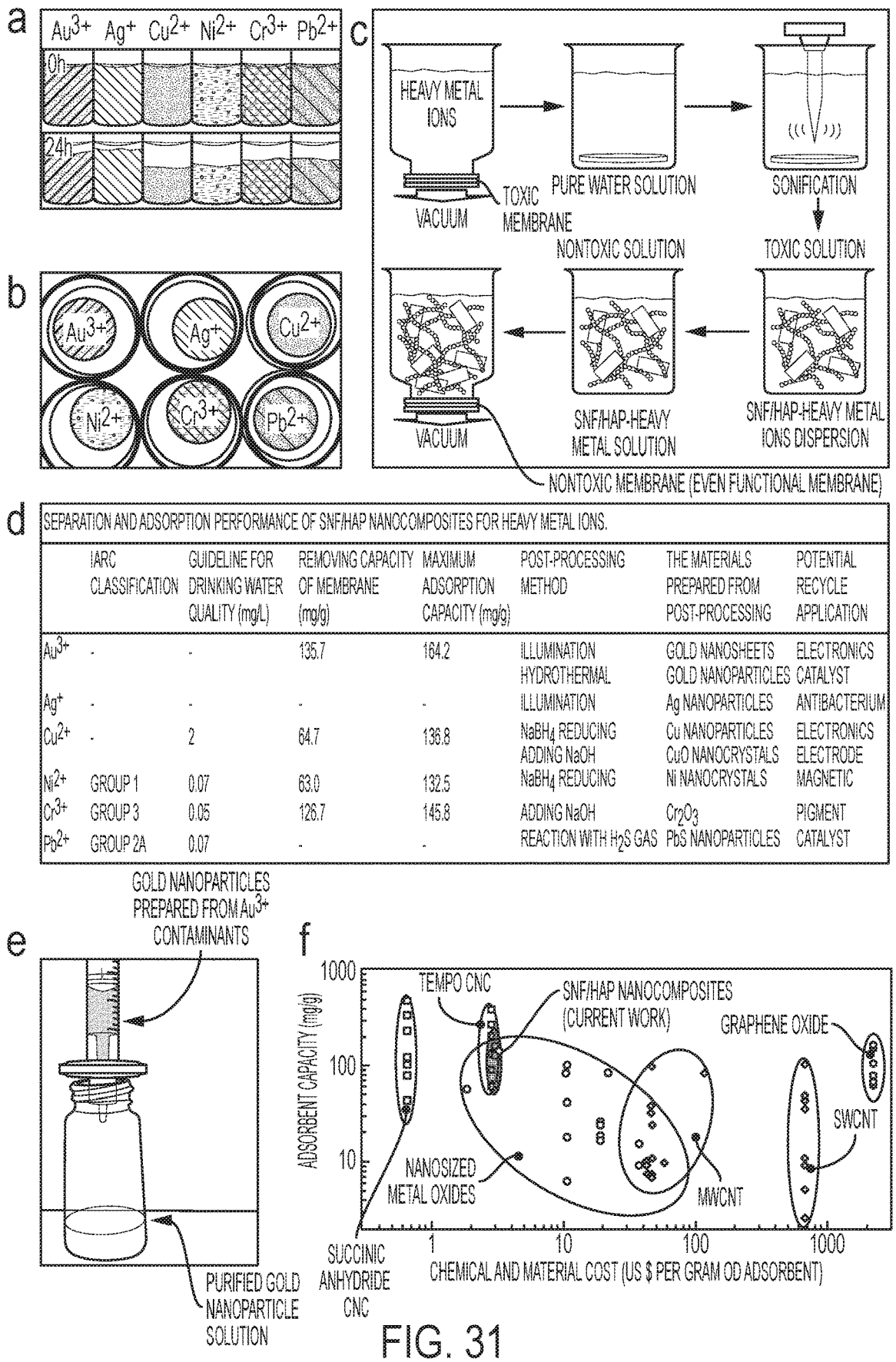
FIG. 31, panel a, shows a photograph of example SNF/HAP dispersions-adsorbed metal ions at 0 (top) and 24 h (bottom). Panel b shows a photograph of a SNF/HAP membrane after metal ions were adsorbed through flux controllable filtration. Panel c shows a schematic of an example route for recycling metal ion contaminants by re-dispersion of a saturated SNF/HAP membrane. Panel d is a table describing separation and adsorption performance of SNF/HAP nanocomposites for heavy metal ions. Panel e shows a photograph of an example membrane filtration set-up illustrating that gold contaminants can be reused after facile and green post-processing. Panel f is a table of cost and adsorption capacity estimates for the most-studied nanomaterials.

In some implementations, multilayer nanoporous membranes can enhance adsorption performance compared to other filtration techniques, for example absorption of heavy metal ions. FIG. 31 show aspects of removal and recycle of heavy metal ions by SNF/HAP membranes. FIG. 31, panel a shows a photograph of example SNF/HAP dispersions-adsorbed metal ions at 0 (top) and 24 h (bottom). FIG. 31, panel b shows a photograph of a SNF/HAP membrane after metal ions were adsorbed through flux controllable filtration. FIG. 31, panel c shows a schematic of an example route for recycling metal ion contaminants by re-dispersion of a saturated SNF/HAP membrane. FIG. 31, panel d is a table describing separation and adsorption performance of SNF/HAP nanocomposites for heavy metal ions. The adsorbent capacity of Ag+ and Pb2+ are not listed quantitatively because Ag+ and Pb2+ interacted with Cl− to yield a precipitate. The maximum adsorption capabilities of SNF/HAP composite for metal ions are calculated from equilibrium adsorption isotherms data. FIG. 31, panel e shows a photograph of an example membrane filtration set-up illustrating that gold contaminants can be reused after facile and green post-processing. FIG. 31, panel f is a table of cost and adsorption capacity estimates for the most-studied nanomaterials.

In an example embodiment, both SNF and HAP components can exhibit excellent adsorption of heavy metal ions (see FIG. 31, panels a and b). Removing metal ions is a formidable yet critical task for water purification because heavy metal ions tend to accumulate in living organisms and are toxic and cancerogenic, such as Ni2+, Cr3+ and Pb2+ (FIG. 5d). Therefore, the concentration of metal ions is strictly restricted to trace levels in drinking water. According to the WHO guidelines for drinking water quality, the concentration of Cu2+, Ni2+, Cr3+ and Pb2+ should be lower than 2, 0.07, 0.05 and 0.07 mg/L, respectively (FIG. 31, panel d). Although conventional membrane-based technologies have advantages for heavy metal removal, such as ease of operation and space savings, their removal efficiencies are often poor because the pore sizes of the membranes are larger than those of the dissolved metal ions. Without wishing to be bound by theory, the mechanism by which multilayer nanoporous membranes, e.g., SNF/HAP membranes, can remove metal ions is derived from evidence that both the SNF and HAP components can interact with metal ions through chelation and ion-exchange, respectively.

Described herein adsorption capacity of example SNF/HAP multilayer membranes for a series of heavy metal ions ($Au^{3+}$, Ag+, $Cu^{2+}$, $Ni^{2+}$, $Pb^{2+}$ and $Cr^{3+}$) via a flux-controllable filtration process. In an example process, 20 mL 0.2 wt % SNF/HAP solution was used for making membranes. A 0.01 M metal ion solution was allowed to slowly pass through the SNF/HAP membranes after standing for approximately 4 h. The adsorption capacities of SNF/HAP membranes in this condition for $Au^{3+}$, $Cu^{2+}$, $Ni^{2+}$ and $Cr^{3+}$ ions are 135.7, 64.7, 63.0, 126.7 mg $g^{-1}$, respectively. The adsorption capacities of $Ag^+$ and $Pb^{2+}$ are not listed quantitatively because Ag+ and $Pb^{2+}$ interacted with $Cl^-$ to yield a precipitate.

Another example process shows adsorption performance of $Au^{3+}$, $Cu^{2+}$, $Ni^{2+}$ and $Cr^{3+}$ ions on the SNF/HAP adsorbents. A 0.2 wt % SNF/HAP solution is concentrated by vacuum filtration to remove most water in solution. The resultant slurry is then processed by freeze-drying to obtain SNF/HAP adsorbents. All the sorption tests are conducted in capped 600 mL flasks containing 150 mL metal ion aqueous solutions, which were prepared with deionized water. The initial metal ion concentration of the adsorption isotherms and kinetic experiments are set as 100 mg $L^{-1}$ and 10 mg $L^{-1}$, respectively. The dosage of SNF/HAP adsorbents is increased gradually from 50 to 350 mg. After adsorption, the adsorbent is filtered using a 0.2 μm membrane. The residual metal ion concentrations in the solutions is determined by using inductively coupled plasma atomic emission spectrometry (ICP-AES).

Figure 32:
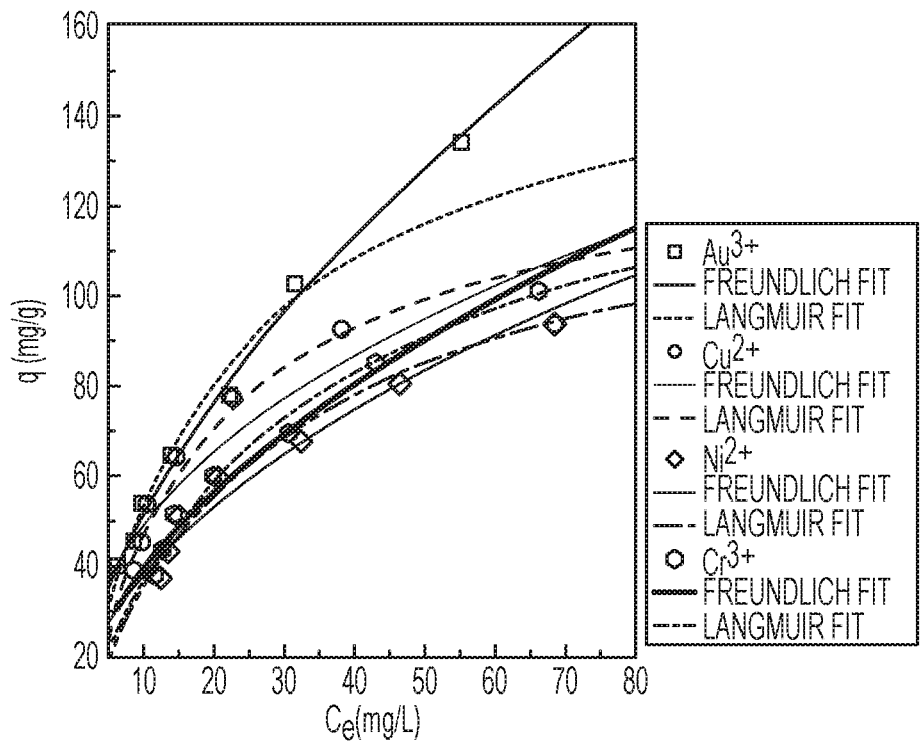
FIG. 32 shows a graph illustrating equilibrium adsorption isotherms of adsorption of various metals on SNF/HAP nanocomposites.

FIG. 32 shows a graph illustrating equilibrium adsorption isotherms of $Au^{3+}$ (a), $Cu^{2+}$ (b), $Ni^{2+}$ (c) and $Cr^{3+}$ (d) adsorption on SNF/HAP nanocomposites. The experimental data are simulated with the Langmuir and Freundlich models see above, respectively. The relative parameters calculated from the two models are listed in Table 5.

TABLE 5

| Adsorbate | Langmuir model | | | Freundlich model | | |
|---|---|---|---|---|---|---|
| | $q_m$ (mg $g^{-1}$) | KL (L $mg^{-1}$) | $R_2$ | $K_F$ | 1/n | $R_2$ |
| $Au^{3+}$ | 164.2 | 0.048 | 0.98 | 14.22 | 0.56 | 0.99 |
| $Cu^{2+}$ | 136.8 | 0.053 | 0.93 | 19.30 | 0.41 | 0.85 |

TABLE 5-continued

| Adsorbate | Langmuir model | | | Freundlich model | | |
|---|---|---|---|---|---|---|
| | $q_m$ (mg $g^{-1}$) | KL (L $mg^{-1}$) | $R_2$ | $K_F$ | 1/n | $R_2$ |
| $Ni^{2+}$ | 132.5 | 0.036 | 0.95 | 12.70 | 0.48 | 0.94 |
| $Cr^{3+}$ | 145.8 | 0.033 | 0.96 | 11.92 | 0.52 | 0.96 |

It can be seen from Table 5 that both models show good agreement with the experimental data except for $Cu^{2+}$ ion, where the Langmuir model is a better fit than the Freundlich model. The maximum adsorption capacity show the same tendency with initial evaluation by using SNF/HAP membranes, that is, $Au^{3+}>Cr^{3+}>Cu^{2+}\approx Ni^{2+}$. Moreover, the Freundlich constant n for all ions is larger than 1, which indicates favorable conditions for adsorption.

Figure 33:
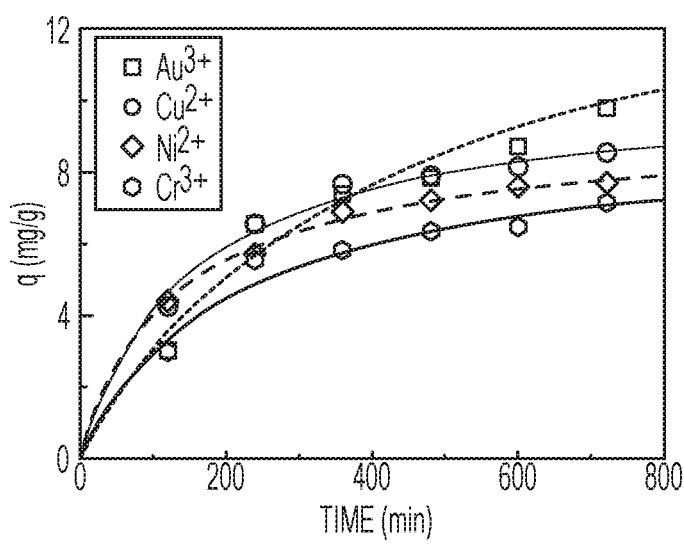
FIG. 33 shows a graph illustrating kinetic curves of example SNF/HAP nanocomposites for removing metal ions.

FIG. 33 shows a graph illustrating kinetic curves of example SNF/HAP nanocomposites for removing metal ions. The solid lines are fitting results according to second-order adsorption kinetic models. Table 6 shows kinetic parameters of second-order adsorption kinetic models for metal ions on example SNF/HAP nanocomposites. (Initial metal ions concentration=10 mg L−1).

TABLE 6

| Adsorbate | $q_e$ (mg $g^{-1}$) | k2 ($min^{-1}$) | $R^2$ |
|---|---|---|---|
| $Au^{3+}$ | 15.8 | 1.5 × $10^4$ | 0.92 |
| $Cu^{2+}$ | 10.3 | 6.5 × $10^4$ | 0.99 |
| $Ni^{2+}$ | 9.2 | 8.2 × $10^4$ | 0.99 |
| $Cr^{3+}$ | 9.1 | 5.3 × $10^4$ | 0.97 |

The removal rate of metal ion adsorption on SNF/HAP is rapid initially, during the first ~300 min, and then decelerates with the increase of contact time from ~300 to ~700 min, and nearly reaches a plateau. The time required for $Au^{3+}$ ion to reach equilibrium is a longer than that of the other metal ions, which may be attributed to the factor that silk protein can reduce the $Au^{3+}$ ions to Au nanoparticles even under ambient conditions. Analyzing the example data by using pseudo-second-order (PS) kinetic models show $R_2$ values of the PS kinetic model with least value of 0.92, indicating that the adsorption of metal ions onto SNF/HAP composites follows PS kinetics.

The technologies described herein may include methods for recycling material adsorbed by a multilayer nanoporous membrane.

Figure 34:
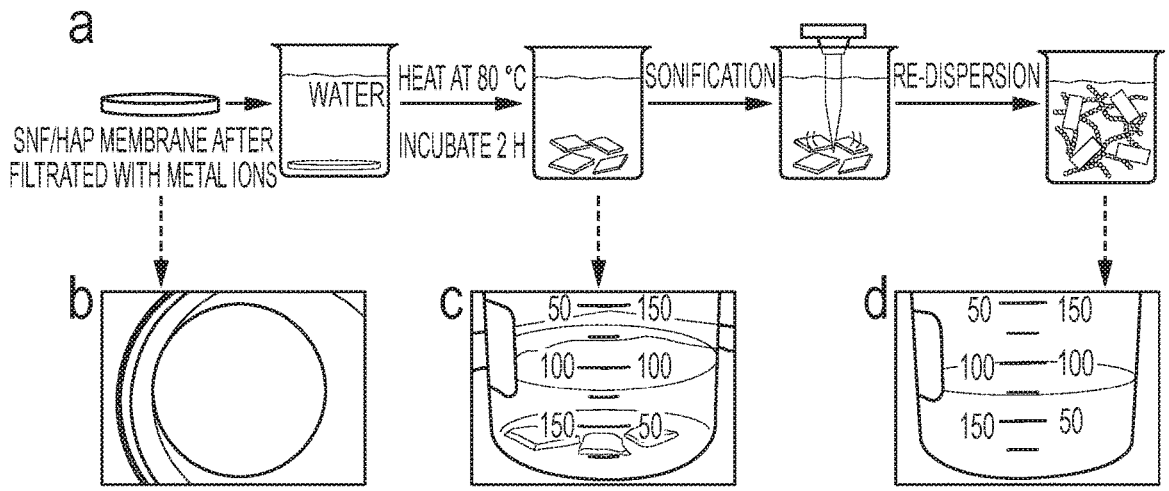
FIG. 34, panel a, shows a schematic representation of a dispersion approach using sonification. Panel b shows a photograph of an example SNF/HAP membrane after filtering with 0.1 M Au3+ ion solution. Panel c shows a photograph of an example Au3+ ion saturated SNF/HAP membrane. Panel d shows a photograph of a SNF/HAP dispersion prepared from solution in panel c after sonification at 120 µm amplitude and 20 kHz frequency, with intervals of 10 sec for 1 h.

Example SNF/HAP membranes described herein provide a new approach to reuse these metal ion contaminants. $Au^{3+}$ ions, for example, can be recycled and reused through redispersion of SNF/HAP composites. FIG. 34 illustrates re-dispersion of SNF/HAP membranes after filtration with Au3+ ions. FIG. 34, panel a shows a schematic representation of a dispersion approach using sonification. In an example process, as shown in FIG. 34, panel a, an SNF/HAP membrane having filtered metal ions is transferred to a water bath, and then heated at 80° C. for 2 or 4 h. The SNF/HAP membrane is broken up into pieces. Next, sonication (120 μm amplitude and 20 KHz frequency, with intervals of 10 sec) is applied to the broken SNF/HAP membrane to obtain SNF/HAP dispersions. FIG. 34, panels b-d show photographs illustrating a re-dispersion process of SNF/HAP membrane after filtration with Au3+ ion solution. FIG. 34, panel b shows a photograph of an example SNF/HAP membrane after filtering with 0.1 M Au3+ ion solution. FIG. 34, panel c shows a photograph of an example Au3+ ion saturated SNF/HAP membrane after incubation in 80 mL water at 80° C. for 4 h. FIG. 34, panel d shows a photograph of a SNF/HAP dispersion prepared from solution in FIG. 34, panel c after sonification at 120 μm amplitude and 20 kHz frequency, with intervals of 10 sec for 1 h.

Figure 35:
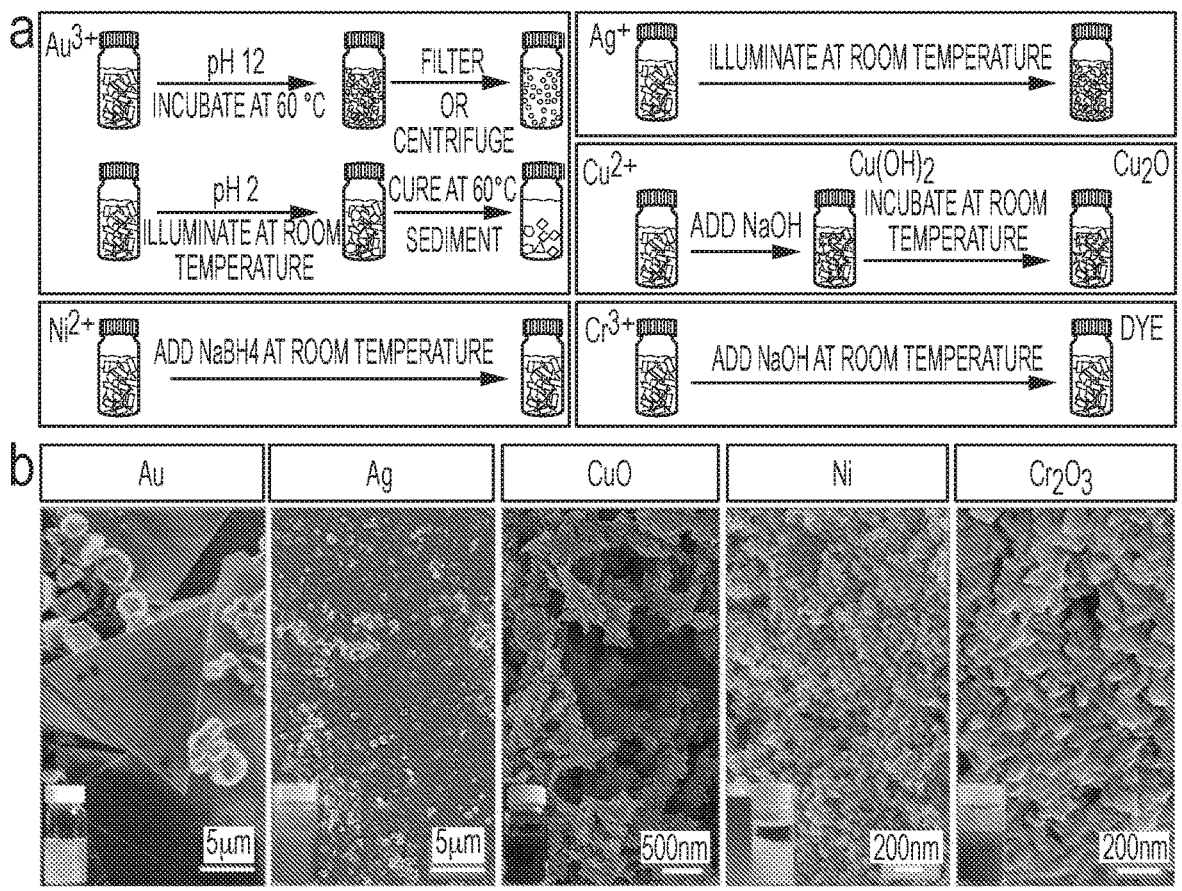
FIG. 35, panel a, shows a schematic representation of example post-processing methods for specific metal ion contaminants. Panel b shows SEM images of metal nanomaterials synthesized from metal ion contaminants by using example post-processing approaches.

An example recycling process of metal ion contaminants for the SNF/HAP filtration membranes is summarized in FIG. 35. FIG. 35, panel a shows a schematic representation of example post-processing methods for specific metal ion contaminants. The useful metal nanomaterials can directly synthesized from ions/SNF/HAP dispersions (first column images) that were prepared from ultrasonic dispersion of adsorbed-saturated ion SNF/HAP membranes. The limiting adsorption ability of SNF/HAP composites are larger than SNF/HAP membranes. Thus, to achieve maximum reduction of metal ions, 1 mL 0.1 M metal ions can be added into 10 g re-dispersed SNF/HAP dispersion to adsorb more metal ions followed by reduction with specific methods. FIG. 35, panel b shows SEM images of metal nanomaterials synthesized from metal ion contaminants by using example post-processing approaches. For $Au^{3+}$ ions, gold nanosheets are shown, which were reduced by SNFs under sunlight at pH 2. The reduced gold nanoparticles are shown in FIG. 31, panel e. For $Au^{3+}$ ions, the $Au^{3+}$ contaminate is used as the source of gold, and SNFs serves as reductant. No other chemical reagents are needed. The synthesis can be carried out under illumination with sunlight at room temperature or mild heating (~60° C.) (21). The $Au^{3+}$ ions are reduced to gold nanoparticles and nanosheets under basic (pH 12) and acidic pH (pH 2) conditions, respectively. The synthetic gold nanoparticles and nanosheets could be collected through syringe filtration or by sedimentation, due to the density difference between gold nanomaterials and the SNF/HAP composites. These gold nanomaterials can be useful for bio-imaging, catalysts and electronics. $Ag^+$ ions, similar to $Au^{3+}$ ions, can be directly reduced to Ag nanoparticles under illumination by sunlight at room temperature without chemical reagents. However, before the filtration to adsorb $Ag^+$ ions, the membranes are washed by DI water several times to remove $Cl^-$ ions because they can react with $Ag^+$ and generate AgCl particles. The reduced Ag nanoparticles combined with SNF/HAP composites can be assembled to antibacterial membranes. For $Cu^{2+}$ ions, there are at least two example post-processing methods for reuse: Example method 1: reduce $Cu^{2+}$ ions to Cu nanoparticles by adding $NaBH_4$ solution. Example Method 2: synthesize CuO nanoparticles by adding NaOH solution. Example method 2 is more facile and green. CuO nanoparticles resulting from example method 2 can be used as electrode materials after calcination. $Ni^{2+}$ ions are reduced to Ni nanoparticles by adding $NaBH_4$ solution. The resultant Ni nanoparticles show magnetism and can be used in magnetic nanomaterials. $Cr^{3+}$ ions can be synthesized to $Cr_2O_3$ nanoparticles by adding NaOH solution. The $Cr_2O_3$ nanoparticles are useful dyes in industry. $Pb^{2+}$ ions are more complex to recycle, with a possible approach to prepare PbS nanoparticles by reaction with $H_2S$ gas. The resultant PbS nanoparticles could be used as catalysts. Additional options for green recovery also include enzymatic digestion of the silk via proteases to release the metals, or pH related controls for similar goals (e.g., use of low pH aqueous solutions to dissolve certain embodiments).

In some implementations, saturated membranes can be re-dispersed in water by ultrasonication. Post-processing can then be applied to synthesize nontoxic nanomaterials or reusable functional nanomaterials, followed by assembling these nontoxic nanomaterial dispersions into bulk materials to avoid producing potentially toxic nanomaterials (FIG. 31, panel e). In an example process, at least of 92±4% ($Au^{3+}$) ion contaminants can be removed and do not yield any secondary pollutants.

The broad acceptance of novel water purification nanotechnologies depends on their performance and affordability. FIG. 31, panel f and Tables 7 and 8 summarize the cost estimation versus adsorbent capacity of the most studied nanomaterials. Table 7 shows estimated total cost for preparing one gram of nano-adsorbents. Table 8 shows maximum sorption capacities of metal ions with different nanomaterials. The SNF/HAP composites show optimum performance in terms of both price and adsorbent capacity. The cost of an example SNF/HAP membrane is approximately $3.36 per gram, which is comparable with the costs of CNC materials ($0.65-2.80). In terms of adsorbent capacity, SNF/HAP membranes appear better than other inorganic nanomaterials and similar to the CNC hydrogels, but considering the additional size-exclusion affection of SNF/HAP membrane for dyes or other molecular contaminants, the SNF/HAP membrane may exhibit greater capability for water treatment than CNC hydrogels.

TABLE 7

| Adsorbent | Used materials and chemicals | Amount used | Unit cost US $ | Cost US$ | Total chemical and material cost (US $ per gram of adsorbent | Other costs increasing factors or remarks |
|---|---|---|---|---|---|---|
| Hematite ($\alpha$-$Fe_2O_3$) | $FeCl_3$ | 2.7 g | 6.52 | 17.60 | 21.75 | Heating at 90° C. for 2 days |
| | DI water | 500 mL | 0.0226 | 11.3 | | |
| | HCl | 0.05 mL | 0.549 | 0.03 | | |
| $\gamma$-$Fe_2O_3$ | DI water | 200 mL | 0.0226 | 4.52 | 19.01 | Nitrogen gas, rinsed ultrapure water, freeze-drying |
| | $FeCl_3$ | 5.2 g | 6.52 | 33.90 | | |
| | $FeCl_2$ | 2.0 g | 3.18 | 6.36 | | |
| | $NH_4OH$ | 1.5M | 0.0826 | 2.90 | | |
| | Tetramethylammonium hydroxide | 1mL 25% | 0.2264 | 0.23 | | |
| | 99% Octyl ether | N/A | N/A | | | |
| $\alpha$-$MnO_2$(OMS-2) | $NaSO_4$ | 250 mL 0.15M | 0.1042 | 0.56 | 10.35 | Heating and boiling for 24 h, ion-exchanged water |
| | DI water | 250 mL | 0.0226 | 5.65 | | |
| | 65% $HNO_3$ | 11.5 mL | 0.41 | 2.46 | | |
| | $KMnO_4$ | 2.1 g | 1.592 | 3.34 | | |
| $\alpha$-$MnO_2$(OMS-1) | $MnSO_4$ | 400 mL $C_{Mn2+}$ = 0.6M | 0.273 | 11.07 | 1.84 | Nitrogen gas, oxygen, DI water for washing |
| | NaOH | 400 mL 5M | 0.1886 | 15.09 | | |
| | $MgCl_2$ | 1M | 0.537 | 12.24 | | |

TABLE 7-continued

| Adsorbent | Used materials and chemicals | Amount used | Unit cost US $ | Cost US$ | Total chemical and material cost (US $ per gram of adsorbent) | Other costs increasing factors or remarks |
|---|---|---|---|---|---|---|
| γ-MPTMS modified γ-$Al_2O_3$ | $Al_2O_3$ | 5 g | 9.175 | 45.88 | 21.00 | DI water and ethanol for washing, vacuum drying |
| | Benzene | 100 mL | 0.595 | 59.50 | | |
| | R-MPTMS | 1% (m/v) | 1.224 | 1.22 | | |
| DNPH modified γ-$Al_2O_3$ | Alumina nanopartcles | 2.0 g | 9.175 | 18.35 | 10.53 | |
| | DI water | 50 mL | 0.0226 | 1.13 | | |
| | SDS | 0.1 g | 1.62 | 0.16 | | |
| | 2,4-dinitrophenylhydrazine (0.90 g DNPH in HCl + acetonitrile) | 0.9 | 1.572 | 1.41 | | |
| ZnO | $Zn(CH_3COO)_2 \cdot 2H_2O$ | 0.66 g | 12.88 | 8.50 | 83.12 | Heating at 160° C. for 12 h, DI water and ethanol for washing |
| | Urea | 0.54 g | 0.1542 | 0.08 | | |
| | Ethylene glycol | 25 mL | 0.432 | 10.80 | | |
| | DI water | 25 mL | 0.0226 | 0.57 | | |
| $CeO_2$ | $Ce(NO_3)_3 \cdot 6H_2O$ | 100 mL 1mM | 9.66 | 4.19 | 37.60 | Autoclave, heating at 500° C. for 2 h |
| | Urea | 1.5 mmol | 0.1542 | 0.01 | | |
| | DI water | 100 mL | 0.0226 | 2.26 | | |
| TEMPO oxided CNC | CNC | 1g | 0.3 | 0.30 | 2.80 | Dialyzing cellulose dialysis membrane for 1 week |
| | TEMPO-reagent | 0.059 g | 0.57 | 0.33 | | |
| | NaBr | 0.325 g | 0.112 | 0.04 | | |
| | NaClO | 7.1 mL | 0.190 | 1.35 | | |
| | Methanol | 11 mL | 0.063 | 0.70 | | |
| | NaOH | N/A mL | 0.008 | N/A | | |
| | HCl | N/A mL | 0.01 | N/A | | |
| Succinic anhydride/CNC | CNC powder | 1 g | 0.17 | 0.17 | 0.65 | Drying in vacuum at 383 K. for 24 h |
| | N,N-dimethylacetamide | 5 mL | 0.063 | 0.32 | | |
| | Succinic anhydride | 0.6 g | 0.26 | 0.16 | | |
| | Sodium hydrogencarbonate | N/A g | 0.018 | N/A | | |
| MWCNT | / | / | / | / | 42.35 | |
| SWCNT | / | / | / | / | 676 | |
| MWCNT, carboxylic acid functionalized | / | / | / | / | 116.5 | |
| Graphene oxide | / | / | / | / | 2215 | |
| SNF/HAP | Cocoons | 1 g | 0.015 | 0.02 | 3.36 | Degumming and dialysis |
| | LiBr | 8.077 g | 0.120 | 0.97 | | |
| | DI water | 100 mL | 0.023 | 2.26 | | |
| | $CaCl_2$ | 0.133 g | 0.343 | 0.05 | | |
| | $Na_2HPO_4$ | 0.17 g | 0.39 | 0.07 | | |

The prices of chemical reagents, carbon nanotubes and graphene oxide were obtained from Sigma-Aldrich website (https://www.sigmaaldrich.com/united-states.html). The price of cocoons was obtained from Alibaba website (www.1688.com/). The price of cocoons has some differences, depending on the place of purchase and the type of cocoons. Here a chose a median price to calculation. The cost of SNF/HAP can be further reduced if using industrial waste silk as raw materials. Abbreviations: DI water, deionized water; OMS, octahedral molecular sieves; γ-MPTMS, γ-mercaptopropyltrimethoxysilane; DNPH, 2,4-Dinitrophenylhydrazine; SDS, sodium dodecyl sulfate; CNC, cellulose nanocrystals; TEMPO, 2,2,6,6-tetramethylpiperidinyl-1-oxyl radical; CNT, carbon nanotube; MCNT, multi-wall carbon nanotube; SWCNT, single-wall carbon nanotube; SNF, silk nanofibrils; HAP, hydroxyapatite.

TABLE 8

| Adsorbent | Preparation | Conditions | Target metals | Maximum sorption capacity (mg/g) |
|---|---|---|---|---|
| Hematite (α-$Fe_2O_3$) | Coprecipitation | pH = 5.2 ± 0.1 | $Cu^{2+}$ | 84.46 |
| γ-$Fe_2O_3$ | Sol-gel method | pH = 2-3 | $Cr^{4+}$ | 19.2 |
| | | pH = 2.5 | $Cr^{4+}$ | 17.0 |
| | | pH = 6.5 | $Cu^{2+}$ | 26.8 |
| | | pH = 8.5 | $Ni^{2+}$ | 23.6 |
| α-$MnO_2$ (OMS-2) | Precipitation method | | $Cu^{2+}$ | 83.2 |
| α-$MnO_2$ (OMS-1) | Precipitation method | | $Cu^{2+}$ | 57.6 |
| γ-MPTMS modified γ-$Al_2O_3$ | Mixture | | $Cu^{2+}$ | Removal 100% |
| | | | $Hg^{2+}$ | Removal 97.8-99% |
| | | | $Pd^{2+}$ | Removal 97-100% |
| DNPH modified γ-$Al_2O_3$ | Chemically immobilization | | $Pb^{2+}$ | 100 |
| | | | $Cd^{2+}$ | 83.33 |
| | | | $Cr^{4+}$ | 100 |
| | | | $Co^{2+}$ | 41.66 |
| | | | $Ni^{2+}$ | 18.18 |
| | | | $Mn^{2+}$ | 6.289 |
| ZnO | Hydrothermal | | $Pb^{2+}$ | 6.7 |
| $CeO_2$ | Precipitation | | $Cr^{4+}$ | 15.4 |
| | | | $Pb^{2+}$ | 9.2 |
| CNC | Succinic anhydride (Carboxyl) | pH = 5.6 | $Pb^{2+}$ | 465.75 |
| | | pH = 6 | $Cd^{2+}$ | 343.84 |
| | | | $Zn^{2+}$ | 104 |

TABLE 8-continued

| Adsorbent | Preparation | Conditions | Target metals | Maximum sorption capacity (mg/g) |
|---|---|---|---|---|
|  |  |  | $Ni^{2+}$ | 43.66 |
|  |  |  | $Cu^{2+}$ | 121.6 |
|  |  |  | $Co^{2+}$ | 79.08 |
|  |  |  | $Cd^{2+}$ | 231.5 |
| CNC | TEMPO-oxidized |  | $Cu^{2+}$ | 268.2 |
|  |  |  | $Cs^+$ | 133.8 |
|  |  |  | $Zn^{2+}$ | ~195 |
|  |  |  | $Cd^{2+}$ | ~118 |
|  |  |  | $Fe^{2+}$ | ~95 |
|  |  |  | $Ca^{2+}$ | ~64 |
|  |  |  | $Cu^{2+}$ | ~90 |
|  |  |  | $Ag^+$ | ~202 |
|  |  |  | $Pb^{2+}$ | ~387 |
| CNT |  | pH = 7.0 | $Pb^{2+}$ | 1.0 |
|  |  | pH = 5.0 | $Pb^{2+}$ | 102.04 |
|  |  |  | $Cd^{2+}$ | 1.1 |
| CNT | $HNO_3$ treatment |  | $Pb^{2+}$ | 49.95 |
|  |  |  | $Cd^{2+}$ | 5.1 |
|  |  | pH = 5.0 | $Pb^{2+}$ | 35.6 |
| CNT | $H_2O_2$ treatment | pH = 5.5 | $Cd^{2+}$ | 2.6 |
| CNT | $KMnO_4$ treatment | pH = 5.5 | $Cd^{2+}$ | 11.0 |
| MCNT | $HNO_3$ treatment |  | $Cd^{2+}$ | 7.42 |
|  |  |  | $Ni^{2+}$ | 6.89 |
|  |  | pH = 5.0 | $Cd^{2+}$ | 10.86 |
|  |  | pH = 5.0 | $Cu^{2+}$ | 24.49 |
|  |  | pH = 5.0 | $Pb^{2+}$ | 97.08 |
|  |  | pH = 6.55 | $Ni^{2+}$ | 9.8 |
| SWCNT |  | pH = 7.0 | $Ni^{2+}$ | 9.22 |
|  |  |  | $Zn^{2+}$ | 11.23 |
| SWCNT | NaOCl treatment |  | $Ni^{2+}$ | 47.85 |
|  |  |  | $Zn^{2+}$ | 43.66 |
| MWCNT |  |  | $Ni^{2+}$ | 7.53 |
|  |  |  | $Zn^{2+}$ | 10.21 |
| MWCNT | NaOCl treatment |  | $Ni^{2+}$ | 38.46 |
|  |  |  | $Zn^{2+}$ | 32.68 |
| MWCNT | Iron oxide |  | $Ni^{2+}$ | 9.18 |
| Acidified MWCNT |  |  | $Pb^{2+}$ | 85 |
| Graphene oxide | Modified Hummers method | pH = 6.0; T = 303 K | $Cd^{2+}$ | 106.6 |
|  |  | pH = 6.0; T = 313 K | $Cd^{2+}$ | 153.6 |
|  |  | pH = 6.0; T = 333 K | $Cd^{2+}$ | 167.5 |
|  |  | pH = 6.0; T = 303 K | $Co^{2+}$ | 68.2 |
|  |  | pH = 6.0; T = 313 K | $Co^{2+}$ | 69.4 |
|  |  | pH = 6.0; T = 333 K | $Co^{2+}$ | 79.8 |
|  |  | pH = 4.68 | $Cu^{2+}$ | 62.73 |

On the basis of the simulation findings, different protein-based fibrils (e.g., amyloid, collagen fibril) and their corresponding biomineral systems (e.g., calcification, silicification, etc.) may be evaluated and selected for building multilayer structures in a similar fashion as demonstrated here for the SNF and HAP. In addition, engineered peptides and proteins, such as silk-, silk-elastin-, silaffin-, apatite-binding-peptide-based-peptides or proteins, may also be useful starting materials. The interaction between these peptides/proteins with minerals can be evaluated and predicted by computational simulation. This interaction between simulation and experiment not only allows larger design space for the materials, but can also improve efficiency in the design of new materials with definable structures and properties.

EQUIVALENTS AND SCOPE

While the present invention has been described herein in conjunction with various embodiments and examples, it is not intended that the scope be limited to such embodiments or examples. On the contrary, the present invention encompasses various alternatives, modifications, and equivalents, as will be appreciated by those of skill in the art. Accordingly, the descriptions, methods and diagrams of should not be read as limited to the described order of elements unless stated to that effect.

The invention claimed is:

1. A filtration membrane comprising at least two filtration membrane layer structures, each of the at least two filtration membrane layer structures comprising:
    at least one pliable membrane layer comprising a plurality of silk fibroin nanofibrils; and
    at least one rigid membrane layer comprising a plurality of mineral crystals, wherein each rigid layer is associated with at least one pliable layer.

2. The filtration membrane of claim 1, wherein at least one pliable layer is porous.

3. The filtration membrane of claim 2, wherein the pores of the at least one pliable layer have an average diameter between 1-20 nm.

4. The filtration membrane of claim 1, wherein the at least one pliable layer comprises two or more of silk, silk fibroin, silk-elastin, amyloid, collagen, nanochitin, nanocellulose, and silaffin.

5. The filtration membrane of claim 1, wherein the at least one rigid layer is porous.

6. The filtration membrane of claim 5, wherein the pores of the at least one rigid layer have an average diameter between 5-100 nm.

7. The filtration membrane of claim 1, wherein the silk fibroin nanofibrils have an average aspect ratio of between 1:10 and 1:1,000.

8. The filtration membrane of claim 1, wherein the at least one pliable layer has a thickness between 10 nm and 1,000 μm.

9. The filtration membrane of claim 1, wherein the at least one rigid layer has a thickness between 10 nm and 1,000 um.

10. The filtration membrane of claim 1, wherein the mineral crystals are calcium-containing nanocrystals, titanium-containing nanocrystals, gold-containing nanocrystals, silver-containing nanocrystals, graphene-containing nanocrystals, graphene oxide-containing nanocrystals, or silica-containing nanoparticles.

11. The filtration membrane of claim 10, wherein the calcium-containing nanocrystals are hydroxyapatite crystals or calcium carbonate crystals.

12. The filtration membrane of claim 1, wherein at least one layer of the filtration membrane is formed via one or more of vacuum filtration, injection, spin coating, deposition, cylinder extrusion, and compression.

13. The filtration membrane of claim 1, wherein the filtration membrane comprises at least three pliable layers.

14. The filtration membrane of claim 1, wherein the filtration membrane comprises at least three rigid layers.

15. The filtration membrane of claim 1, wherein the filtration membrane is substantially insoluble.

16. The filtration membrane of claim 1, wherein the filtration membrane has a removal capacity for gold ($Au^{3+}$) of at least 130 mg/g of membrane.

17. The filtration membrane of claim 1, wherein the filtration membrane has a removal capacity for copper ($Cu^{2+}$) of at least 60 mg/g of membrane.

18. The filtration membrane of claim 1, wherein the filtration membrane has a removal capacity for nickel ($Ni^{2+}$) of at least 60 mg/g of membrane.

19. The filtration membrane of claim 1, wherein the filtration membrane has a removal capacity for chromium ($Cr^{3+}$) of at least 120 mg/g of membrane.

20. A method comprising
(a) growing a plurality of mineral crystals on at least one pliable membrane layer comprising a plurality of silk fibroin nanofibrils such that the crystals form at least one rigid membrane layer associated with the at least one pliable membrane layer, thereby producing a first filtration membrane layer structure;
(b) repeating step (a), thereby producing a second filtration membrane layer structure; and
(c) forming a filtration membrane comprising the first and second filtration membrane layer structures.

* * * * *